US011744734B2

(12) United States Patent
Schieber et al.

(10) Patent No.: US 11,744,734 B2
(45) Date of Patent: Sep. 5, 2023

(54) METHOD OF IMPLANTING AN OCULAR IMPLANT

(71) Applicant: Alcon Inc., Fribourg (CH)

(72) Inventors: Andrew T. Schieber, St. Louis Park, MN (US); Charles L. Euteneuer, St. Michael, MN (US)

(73) Assignee: Alcon Inc., Fribourg (CH)

(*) Notice: Subject to any disclaimer, the term of this patent is extended or adjusted under 35 U.S.C. 154(b) by 963 days.

(21) Appl. No.: 16/552,211

(22) Filed: Aug. 27, 2019

(65) Prior Publication Data

US 2019/0380874 A1 Dec. 19, 2019

Related U.S. Application Data

(63) Continuation of application No. 15/012,544, filed on Feb. 1, 2016, now abandoned, which is a continuation-in-part of application No. 14/691,267, filed on Apr. 20, 2015, now Pat. No. 9,610,196, which is a continuation of application No. 14/246,363, filed on Apr. 7, 2014, now Pat. No. 9,039,650, which is a continuation of application No. 12/236,225, filed on Sep. 23, 2008, now Pat. No. 8,734,377, which is a continuation-in-part of application No. 11/860,318, filed on Sep. 24, 2007, now Pat. No. 7,740,604, said application No. 15/012,544 is a continuation-in-part of application No. 14/932,658, filed on Nov. 4, 2015, now Pat. No. 10,406,025, which is a continuation of application No. 13/865,770, filed on Apr. 18, 2013, now Pat. No. 9,211,213, which is a continuation of application No. 12/833,863, filed on Jul. 9, 2010, now Pat. No. 8,425,449.

(60) Provisional application No. 62/110,293, filed on Jan. 30, 2015, provisional application No. 61/224,158, filed on Jul. 9, 2009.

(51) Int. Cl.
*A61F 9/007* (2006.01)

(52) U.S. Cl.
CPC ................................ *A61F 9/00781* (2013.01)

(58) Field of Classification Search
CPC ........................ A61M 127/002; A61F 9/00781
USPC ................................. 604/8, 9; 606/107, 108
See application file for complete search history.

(56) References Cited

U.S. PATENT DOCUMENTS

| | | | |
|---|---|---|---|
| 703,296 | A | 6/1902 | Arnold |
| 1,601,709 | A | 10/1926 | Windom |

(Continued)

FOREIGN PATENT DOCUMENTS

| | | | |
|---|---|---|---|
| AU | 1998/76197 | B2 | 2/1999 |
| CN | 1950091 | | 4/2007 |

(Continued)

OTHER PUBLICATIONS

Wardle et al.; U.S. Appl. No. 16/668,458 entitled "Single operator device for delivering an ocular implant," filed Oct. 30, 2019.

(Continued)

*Primary Examiner* — Leslie R Deak
(74) *Attorney, Agent, or Firm* — Levine Bagade Han LLP

(57) ABSTRACT

A method of inserting an ocular implant into Schlemm's canal, the method comprising: moving the ocular implant into Schlemm's canal; and injecting a visco-elastic medium in front of the implant.

11 Claims, 50 Drawing Sheets

(56) References Cited

U.S. PATENT DOCUMENTS

| | | | |
|---|---|---|---|
| 2,716,983 | A | 9/1955 | George et al. |
| 3,071,135 | A | 1/1963 | Baldwin et al. |
| 3,788,327 | A | 1/1974 | Donowitz et al. |
| 3,811,442 | A | 5/1974 | Maroth |
| 3,858,577 | A | 1/1975 | Bass et al. |
| 3,884,236 | A | 5/1975 | Krasnov |
| 3,948,271 | A | 4/1976 | Akiyama |
| 3,982,541 | A | 9/1976 | L'Esperance |
| 4,037,604 | A | 7/1977 | Newkirk |
| 4,134,405 | A | 1/1979 | Smit |
| 4,273,109 | A | 6/1981 | Enderby |
| 4,391,275 | A | 7/1983 | Fankhauser et al. |
| 4,428,746 | A | 1/1984 | Mendez |
| 4,457,757 | A | 7/1984 | Molteno |
| 4,461,294 | A | 7/1984 | Baron |
| 4,470,407 | A | 9/1984 | Hussein |
| 4,497,319 | A | 2/1985 | Sekine et al. |
| 4,501,274 | A | 2/1985 | Skjaerpe |
| 4,517,973 | A | 5/1985 | Sunago et al. |
| 4,538,608 | A | 9/1985 | L'Esperance |
| 4,548,205 | A | 10/1985 | Armeniades et al. |
| 4,551,129 | A | 11/1985 | Coleman et al. |
| 4,558,698 | A | 12/1985 | O'Dell |
| 4,559,942 | A | 12/1985 | Eisenberg |
| 4,566,438 | A | 1/1986 | Liese et al. |
| 4,580,559 | A | 4/1986 | L'Esperance |
| 4,583,539 | A | 4/1986 | Karlin et al. |
| 4,601,713 | A | 7/1986 | Fuquo |
| 4,604,087 | A | 8/1986 | Joseph |
| 4,633,866 | A | 1/1987 | Peyman et al. |
| 4,658,816 | A | 4/1987 | Ector |
| 4,660,546 | A | 4/1987 | Herrick et al. |
| 4,671,273 | A | 6/1987 | Lindsey |
| 4,689,040 | A | 8/1987 | Thompson |
| 4,699,140 | A | 10/1987 | Holmes et al. |
| 4,706,669 | A | 11/1987 | Schlegel |
| 4,722,350 | A | 2/1988 | Armeniades et al. |
| 4,722,724 | A | 2/1988 | Schocket |
| 4,729,373 | A | 3/1988 | Peyman |
| 4,733,665 | A | 3/1988 | Palmaz |
| 4,750,901 | A | 6/1988 | Molteno |
| 4,770,654 | A | 9/1988 | Rogers et al. |
| 4,791,927 | A | 12/1988 | Menger |
| 4,826,478 | A | 5/1989 | Schocket |
| 4,846,172 | A | 7/1989 | Berlin |
| 4,861,341 | A | 8/1989 | Woodburn |
| 4,876,250 | A | 10/1989 | Clark |
| 4,880,000 | A | 11/1989 | Holmes et al. |
| 4,886,488 | A | 12/1989 | White |
| 4,919,130 | A | 4/1990 | Stoy et al. |
| 4,925,299 | A | 5/1990 | Meisberger et al. |
| 4,934,363 | A | 6/1990 | Smith et al. |
| 4,934,809 | A | 6/1990 | Volk |
| 4,936,825 | A | 6/1990 | Ungerleider |
| 4,946,436 | A | 8/1990 | Smith |
| 4,968,296 | A | 11/1990 | Ritch et al. |
| 4,994,060 | A | 2/1991 | Rink et al. |
| 5,034,010 | A | 7/1991 | Kittrell et al. |
| 5,092,837 | A | 3/1992 | Ritch et al. |
| 5,123,902 | A | 6/1992 | Muller et al. |
| 5,127,901 | A | 7/1992 | Odrich |
| 5,129,895 | A | 7/1992 | Vassiliadis et al. |
| 5,178,604 | A | 1/1993 | Baerveldt et al. |
| 5,180,362 | A | 1/1993 | Worst |
| 5,190,552 | A | 3/1993 | Kelman |
| 5,213,569 | A | 5/1993 | Davis |
| 5,246,452 | A | 9/1993 | Sinnott |
| 5,254,112 | A | 10/1993 | Sinofsky et al. |
| 5,273,056 | A | 12/1993 | McLaughlin et al. |
| 5,290,267 | A | 3/1994 | Zimmermann |
| 5,300,020 | A | 4/1994 | L'Esperance |
| 5,359,685 | A | 10/1994 | Waynant et al. |
| 5,360,399 | A | 11/1994 | Stegmann |
| 5,371,078 | A | 12/1994 | Clark et al. |
| 5,372,577 | A | 12/1994 | Ungerleider |
| 5,445,637 | A | 8/1995 | Bretton |
| 5,454,796 | A | 10/1995 | Krupin |
| 5,458,615 | A | 10/1995 | Klemm et al. |
| 5,501,274 | A | 3/1996 | Nguyen et al. |
| 5,536,259 | A | 7/1996 | Utterberg |
| 5,575,780 | A | 11/1996 | Saito |
| 5,591,223 | A | 1/1997 | Lock et al. |
| 5,607,966 | A | 3/1997 | Hellberg et al. |
| 5,613,972 | A | 3/1997 | Lee et al. |
| 5,626,558 | A | 5/1997 | Suson |
| 5,643,250 | A | 7/1997 | O'Donnell |
| 5,653,753 | A | 8/1997 | Brady et al. |
| 5,657,760 | A | 8/1997 | Ying et al. |
| 5,676,669 | A | 10/1997 | Colvard |
| 5,704,907 | A | 1/1998 | Nordquist et al. |
| 5,713,844 | A | 2/1998 | Peyman |
| 5,722,970 | A | 3/1998 | Colvard et al. |
| 5,736,491 | A | 4/1998 | Patel et al. |
| 5,738,676 | A | 4/1998 | Hammer et al. |
| 5,738,677 | A | 4/1998 | Colvard et al. |
| 5,785,658 | A | 7/1998 | Benaron et al. |
| 5,792,099 | A | 8/1998 | DeCamp et al. |
| 5,792,103 | A | 8/1998 | Schwartz et al. |
| 5,807,302 | A | 9/1998 | Wandel |
| 5,811,453 | A | 9/1998 | Yanni et al. |
| 5,865,831 | A | 2/1999 | Cozean et al. |
| 5,868,697 | A | 2/1999 | Richter et al. |
| 5,879,319 | A | 3/1999 | Pynson et al. |
| 5,885,279 | A | 3/1999 | Bretton |
| 5,893,837 | A | 4/1999 | Eagles et al. |
| 5,895,831 | A | 4/1999 | Brasier et al. |
| 5,919,171 | A | 7/1999 | Kira et al. |
| 5,948,427 | A | 9/1999 | Yamamoto et al. |
| 5,968,058 | A | 10/1999 | Richter et al. |
| 5,984,963 | A | 11/1999 | Ryan et al. |
| 5,990,099 | A | 11/1999 | Clark |
| 5,993,438 | A | 11/1999 | Juhasz et al. |
| 5,997,531 | A | 12/1999 | Loeb et al. |
| 6,002,480 | A | 12/1999 | Izatt et al. |
| 6,007,511 | A | 12/1999 | Prywes |
| 6,050,970 | A | 4/2000 | Baerveldt |
| 6,083,193 | A | 7/2000 | Kadziauskas et al. |
| 6,099,521 | A | 8/2000 | Shadduck |
| 6,102,045 | A | 8/2000 | Nordquist et al. |
| 6,142,990 | A | 11/2000 | Burk |
| 6,146,375 | A | 11/2000 | Juhasz et al. |
| 6,177,544 | B1 | 1/2001 | Kanai et al. |
| 6,186,974 | B1 | 2/2001 | Allan et al. |
| 6,217,584 | B1 | 4/2001 | Nun |
| 6,221,078 | B1 | 4/2001 | Bylsma |
| 6,238,409 | B1 | 5/2001 | Hojeibane |
| 6,241,721 | B1 | 6/2001 | Cozean et al. |
| D444,874 | S | 7/2001 | Haffner et al. |
| 6,297,228 | B1 | 10/2001 | Clark |
| 6,319,274 | B1 | 11/2001 | Shadduck |
| 6,328,747 | B1 | 12/2001 | Nun |
| 6,375,642 | B1 | 4/2002 | Grieshaber et al. |
| 6,398,809 | B1 | 6/2002 | Hoffmann et al. |
| 6,409,752 | B1 | 6/2002 | Boatman et al. |
| 6,450,984 | B1 | 9/2002 | Lynch et al. |
| 6,464,724 | B1 | 10/2002 | Lynch et al. |
| 6,471,666 | B1 | 10/2002 | Odrich |
| 6,494,857 | B1 | 12/2002 | Neuhann |
| 6,508,779 | B1 | 1/2003 | Suson |
| 6,517,523 | B1 | 2/2003 | Kaneko et al. |
| 6,524,275 | B1 | 2/2003 | Lynch et al. |
| 6,533,764 | B1 | 3/2003 | Haffner et al. |
| 6,533,768 | B1 | 3/2003 | Hill |
| 6,544,208 | B2 | 4/2003 | Ethier et al. |
| 6,544,249 | B1 | 4/2003 | Yu et al. |
| 6,551,289 | B1 | 4/2003 | Higuchi et al. |
| 6,626,858 | B2 | 9/2003 | Lynch et al. |
| 6,638,239 | B1 | 10/2003 | Bergheim et al. |
| 6,666,841 | B2 | 12/2003 | Gharib et al. |
| 6,699,210 | B2 | 3/2004 | Williams et al. |
| 6,699,211 | B2 | 3/2004 | Savage |
| 6,702,790 | B1 | 3/2004 | Ross |
| 6,726,676 | B2 | 4/2004 | Stegmann et al. |
| D490,152 | S | 5/2004 | Myall et al. |

(56) References Cited

U.S. PATENT DOCUMENTS 6,730,056 B1 5/2004 Ghaem et al.
6,736,791 B1 5/2004 Tu et al.
6,780,164 B2 8/2004 Bergheim et al.
6,783,544 B2 8/2004 Lynch et al.
6,827,699 B2 12/2004 Lynch et al.
6,827,700 B2 12/2004 Lynch et al.
6,881,198 B2 4/2005 Brown
6,899,717 B2 5/2005 Weber et al.
6,939,298 B2 9/2005 Brown et al.
6,955,656 B2 10/2005 Bergheim et al.
6,962,573 B1 11/2005 Wilcox
6,981,958 B1 1/2006 Gharib et al.
6,989,007 B2 1/2006 Shadduck
7,018,376 B2 3/2006 Webb et al.
7,094,225 B2 8/2006 Tu et al.
7,125,119 B2 10/2006 Farberov
7,133,137 B2 11/2006 Shimmick
7,135,009 B2 11/2006 Tu et al.
7,147,650 B2 12/2006 Lee
7,163,543 B2 1/2007 Smedley et al.
7,186,232 B1 3/2007 Smedley et al.
7,192,412 B1 3/2007 Zhou et al.
7,207,965 B2 4/2007 Simon
7,207,980 B2 4/2007 Christian et al.
7,220,238 B2 5/2007 Lynch et al.
7,273,475 B2 9/2007 Tu et al.
7,297,130 B2 11/2007 Bergheim et al.
7,331,984 B2 2/2008 Tu et al.
7,488,303 B1 2/2009 Haffner et al.
7,699,882 B2 4/2010 Stamper et al.
7,740,604 B2 6/2010 Schieber et al.
7,931,596 B2 4/2011 Rachlin et al.
7,967,772 B2 6/2011 McKenzie et al.
8,012,115 B2 9/2011 Karageozian
8,034,105 B2 10/2011 Stegmann et al.
8,123,729 B2 2/2012 Yamamoto et al.
8,172,899 B2 5/2012 Silvestrini et al.
8,267,882 B2 9/2012 Euteneuer et al.
8,282,592 B2 10/2012 Schieber et al.
8,308,701 B2 11/2012 Horvath et al.
8,337,509 B2 12/2012 Schieber et al.
8,372,026 B2 2/2013 Schieber et al.
8,414,518 B2 4/2013 Schieber et al.
8,425,449 B2 4/2013 Wardle et al.
8,475,374 B2 7/2013 Irazoqui et al.
8,512,404 B2 8/2013 Frion et al.
8,529,494 B2 9/2013 Euteneuer et al.
8,540,659 B2 9/2013 Berlin
8,551,166 B2 10/2013 Schieber et al.
8,629,161 B2 1/2014 Mizuno et al.
8,636,647 B2 1/2014 Silvestrini et al.
8,647,659 B2 2/2014 Robinson et al.
8,657,776 B2 2/2014 Wardle et al.
8,663,150 B2 3/2014 Wardle et al.
8,663,303 B2 3/2014 Horvath et al.
8,734,377 B2 5/2014 Schieber et al.
8,808,222 B2 8/2014 Schieber et al.
8,939,906 B2 1/2015 Huang et al.
8,939,948 B2 1/2015 De Juan, Jr. et al.
8,945,038 B2 2/2015 Yablonski
8,951,221 B2 2/2015 Stegmann et al.
8,961,447 B2 2/2015 Schieber et al.
8,974,511 B2 3/2015 Horvath et al.
9,039,650 B2 5/2015 Schieber et al.
9,050,169 B2 6/2015 Schieber et al.
9,066,750 B2 6/2015 Wardle et al.
9,066,783 B2 6/2015 Euteneuer et al.
9,155,655 B2 10/2015 Wardle et al.
9,211,213 B2 12/2015 Wardle et al.
9,226,852 B2 1/2016 Schieber et al.
9,301,875 B2 4/2016 Tu et al.
9,351,874 B2 5/2016 Schieber et al.
9,358,156 B2 6/2016 Wardle et al.
9,402,767 B2 8/2016 Schieber et al.
9,510,973 B2 12/2016 Wardle
9,579,234 B2 2/2017 Wardle et al.
9,603,741 B2 3/2017 Berlin
9,610,196 B2 4/2017 Schieber et al.
9,636,254 B2 5/2017 Yu et al.
9,642,746 B2 5/2017 Berlin
9,693,899 B2 7/2017 Wardle et al.
9,693,901 B2 7/2017 Horvath et al.
9,693,902 B2 7/2017 Euteneuer et al.
9,730,638 B2 8/2017 Haffner et al.
9,757,276 B2 9/2017 Penhasi
9,775,729 B2 10/2017 McClain et al.
9,782,293 B2 10/2017 Doci
9,788,999 B2 10/2017 Schaller
9,795,503 B2 10/2017 Perez Grossmann
9,808,373 B2 11/2017 Horvath et al.
9,820,883 B2 11/2017 Berlin
9,833,357 B2 12/2017 Berlin
9,931,243 B2 4/2018 Wardle et al.
10,159,601 B2 12/2018 Berlin
10,335,314 B2 7/2019 Berlin
10,363,168 B2 7/2019 Schieber et al.
10,390,993 B1 8/2019 Berlin
10,406,025 B2 9/2019 Wardle et al.
11,135,088 B2 10/2021 Wardle et al.
2001/0002438 A1 5/2001 Sepetka et al.
2001/0021835 A1 9/2001 Mitchell et al.
2002/0003546 A1 1/2002 Mochimaru et al.
2002/0013546 A1 1/2002 Grieshaber et al.
2002/0013572 A1 1/2002 Berlin
2002/0052653 A1 5/2002 Durgin
2002/0072673 A1 6/2002 Yamamoto et al.
2002/0082591 A1 6/2002 Haefliger
2002/0133168 A1 9/2002 Smedley et al.
2002/0143284 A1 10/2002 Tu et al.
2002/0165504 A1 11/2002 Sharp et al.
2002/0165522 A1 11/2002 Holmen
2002/0193805 A1 12/2002 Ott et al.
2003/0004457 A1 1/2003 Andersson
2003/0014092 A1 1/2003 Neuhann
2003/0040754 A1 2/2003 Mitchell et al.
2003/0055372 A1 3/2003 Lynch et al.
2003/0060748 A1 3/2003 Baikoff
2003/0060752 A1 3/2003 Bergheim et al.
2003/0060784 A1 3/2003 Hilgers et al.
2003/0093084 A1 5/2003 Nissan et al.
2003/0097151 A1 5/2003 Smedley et al.
2003/0105456 A1 6/2003 Lin
2003/0125351 A1 7/2003 Azuma et al.
2003/0175324 A1 9/2003 Robinson et al.
2003/0181848 A1 9/2003 Bergheim et al.
2003/0187384 A1 10/2003 Bergheim et al.
2003/0212387 A1 11/2003 Kurtz et al.
2003/0229303 A1 12/2003 Haffner et al.
2003/0236483 A1 12/2003 Ren
2003/0236484 A1 12/2003 Lynch et al.
2004/0024345 A1 2/2004 Gharib et al.
2004/0024453 A1 2/2004 Castillejos
2004/0030302 A1 2/2004 Kamata et al.
2004/0070761 A1 4/2004 Horvath et al.
2004/0082939 A1 4/2004 Berlin
2004/0088048 A1 5/2004 Richter et al.
2004/0092856 A1 5/2004 Dahan
2004/0098124 A1 5/2004 Freeman et al.
2004/0102729 A1 5/2004 Haffner et al.
2004/0106975 A1 6/2004 Solovay et al.
2004/0111050 A1 6/2004 Smedley et al.
2004/0116909 A1 6/2004 Neuberger et al.
2004/0122380 A1 6/2004 Utterberg
2004/0127843 A1 7/2004 Tu et al.
2004/0147870 A1 7/2004 Burns et al.
2004/0193095 A1 9/2004 Shadduck
2004/0193262 A1 9/2004 Shadduck
2004/0199149 A1 10/2004 Myers et al.
2004/0199171 A1 10/2004 Akahoshi
2004/0210181 A1 10/2004 Vass et al.
2004/0210185 A1 10/2004 Tu et al.
2004/0216749 A1 11/2004 Tu
2004/0225357 A1 11/2004 Worst et al.
2004/0228013 A1 11/2004 Goldstein et al.

(56) References Cited

U.S. PATENT DOCUMENTS

2004/0249333 A1 12/2004 Bergheim et al.
2004/0254517 A1 12/2004 Quiroz-Mercado et al.
2004/0254519 A1 12/2004 Tu et al.
2004/0254520 A1 12/2004 Porteous et al.
2004/0260228 A1 12/2004 Lynch et al.
2005/0038334 A1 2/2005 Lynch et al.
2005/0041200 A1 2/2005 Rich
2005/0043722 A1 2/2005 Lin
2005/0049578 A1 3/2005 Tu et al.
2005/0090806 A1 4/2005 Lynch et al.
2005/0090807 A1 4/2005 Lynch et al.
2005/0101967 A1 5/2005 Weber et al.
2005/0107734 A1 5/2005 Coroneo
2005/0119601 A9 6/2005 Lynch et al.
2005/0119636 A1 6/2005 Haffner et al.
2005/0125003 A1 6/2005 Pinchuk et al.
2005/0131514 A1 6/2005 Hijlkema et al.
2005/0149114 A1 7/2005 Cartledge et al.
2005/0154443 A1 7/2005 Linder et al.
2005/0165385 A1 7/2005 Simon
2005/0192527 A1 9/2005 Gharib et al.
2005/0197667 A1 9/2005 Chan et al.
2005/0203542 A1 9/2005 Weber et al.
2005/0209549 A1 9/2005 Bergheim et al.
2005/0209550 A1 9/2005 Bergheim et al.
2005/0240168 A1 10/2005 Neuberger et al.
2005/0244464 A1 11/2005 Hughes
2005/0245916 A1 11/2005 Connor
2005/0250788 A1 11/2005 Tu et al.
2005/0260186 A1 11/2005 Bookbinder et al.
2005/0266047 A1 12/2005 Tu et al.
2005/0271704 A1 12/2005 Tu et al.
2005/0273033 A1 12/2005 Grahn et al.
2005/0277864 A1 12/2005 Haffner et al.
2005/0279369 A1 12/2005 Lin
2005/0288619 A1 12/2005 Gharib et al.
2005/0288745 A1 12/2005 Andersen et al.
2006/0020247 A1 1/2006 Kagan et al.
2006/0021623 A1 2/2006 Miller et al.
2006/0032507 A1 2/2006 Tu
2006/0052879 A1 3/2006 Kolb
2006/0069340 A1 3/2006 Simon
2006/0074375 A1 4/2006 Bergheim et al.
2006/0079828 A1 4/2006 Brown
2006/0084907 A1 4/2006 Bergheim et al.
2006/0084954 A1 4/2006 Zadoyan et al.
2006/0106370 A1 5/2006 Baerveldt et al.
2006/0110428 A1 5/2006 deJuan et al.
2006/0116626 A1 6/2006 Smedley et al.
2006/0129141 A1 6/2006 Lin
2006/0149194 A1 7/2006 Conston et al.
2006/0154981 A1 7/2006 Klimko et al.
2006/0155238 A1 7/2006 Shields
2006/0155265 A1 7/2006 Juhasz et al.
2006/0155300 A1 7/2006 Stamper et al.
2006/0167421 A1 7/2006 Quinn
2006/0167466 A1 7/2006 Dusek
2006/0173397 A1 8/2006 Tu et al.
2006/0173399 A1 8/2006 Rodgers et al.
2006/0178674 A1 8/2006 McIntyre
2006/0189915 A1 8/2006 Camras et al.
2006/0189916 A1 8/2006 Bas et al.
2006/0189917 A1 8/2006 Mayr et al.
2006/0195055 A1 8/2006 Bergheim et al.
2006/0195056 A1 8/2006 Bergheim et al.
2006/0195187 A1* 8/2006 Stegmann ........... A61F 9/00781 623/4.1
2006/0200113 A1* 9/2006 Haffner ............... A61F 9/00781 606/6
2006/0224146 A1 10/2006 Lin
2006/0241749 A1 10/2006 Tu et al.
2006/0259021 A1 11/2006 Lin
2006/0264971 A1 11/2006 Akahoshi
2006/0276759 A1 12/2006 Kinast et al.
2007/0010827 A1 1/2007 Tu et al.
2007/0021725 A1 1/2007 Villette
2007/0027452 A1 2/2007 Varner et al.
2007/0073275 A1 3/2007 Conston et al.
2007/0088432 A1 4/2007 Solovay et al.
2007/0093794 A1 4/2007 Wang et al.
2007/0093796 A1 4/2007 Raksi et al.
2007/0106200 A1 5/2007 Levy
2007/0106236 A1 5/2007 Coroneo
2007/0112292 A1 5/2007 Tu et al.
2007/0118147 A1 5/2007 Smedley et al.
2007/0121120 A1 5/2007 Schachar
2007/0135681 A1 6/2007 Chin et al.
2007/0173791 A1 7/2007 Raksi
2007/0179520 A1 8/2007 West
2007/0191863 A1 8/2007 De Juan, Jr. et al.
2007/0202186 A1 8/2007 Yamamoto et al.
2007/0208325 A1 9/2007 Kurtz
2007/0219509 A1 9/2007 Tashiro et al.
2007/0219541 A1 9/2007 Kurtz
2007/0235543 A1 10/2007 Zadoyan et al.
2007/0236771 A1 10/2007 Zadoyan et al.
2007/0265582 A1 11/2007 Kaplan et al.
2007/0270945 A1 11/2007 Kobayashi et al.
2007/0276315 A1 11/2007 Haffner et al.
2007/0276316 A1 11/2007 Haffner et al.
2007/0282244 A1 12/2007 Tu et al.
2007/0282245 A1 12/2007 Tu et al.
2007/0293807 A1 12/2007 Lynch et al.
2007/0293872 A1 12/2007 Peyman
2007/0298068 A1 12/2007 Badawi et al.
2008/0015488 A1 1/2008 Tu et al.
2008/0027519 A1 1/2008 Guerrero
2008/0045878 A1 2/2008 Bergheim et al.
2008/0058704 A1 3/2008 Hee et al.
2008/0058777 A1 3/2008 Kurtz et al.
2008/0082088 A1 4/2008 Kurtz et al.
2008/0091224 A1 4/2008 Griffis et al.
2008/0119827 A1 5/2008 Kurtz et al.
2008/0228127 A1 9/2008 Burns et al.
2008/0278687 A1 11/2008 Somani
2008/0288082 A1 11/2008 Deal
2008/0312661 A1 12/2008 Downer et al.
2009/0005852 A1 1/2009 Gittings et al.
2009/0028953 A1 1/2009 Yamamoto et al.
2009/0030363 A1 1/2009 Gellman
2009/0030381 A1 1/2009 Lind et al.
2009/0036843 A1 2/2009 Erskine
2009/0043321 A1 2/2009 Conston et al.
2009/0054723 A1 2/2009 Khairkhahan et al.
2009/0069786 A1 3/2009 Vesely et al.
2009/0082860 A1 3/2009 Schieber et al.
2009/0082862 A1 3/2009 Schieber et al.
2009/0082863 A1 3/2009 Schieber et al.
2009/0104248 A1 4/2009 Rapacki et al.
2009/0118716 A1 5/2009 Brownell
2009/0118717 A1 5/2009 Brownell et al.
2009/0118718 A1 5/2009 Raksi et al.
2009/0131921 A1 5/2009 Kurtz et al.
2009/0132040 A1 5/2009 Frion et al.
2009/0137988 A1 5/2009 Kurtz
2009/0138081 A1 5/2009 Bergheim et al.
2009/0157062 A1 6/2009 Hauger et al.
2009/0171327 A1 7/2009 Kurtz et al.
2009/0182421 A1 7/2009 Silvestrini et al.
2009/0198248 A1 8/2009 Yeung et al.
2009/0204053 A1 8/2009 Nissan et al.
2009/0227934 A1 9/2009 Euteneuer et al.
2009/0247955 A1 10/2009 Yamamoto et al.
2009/0259126 A1 10/2009 Saal et al.
2009/0281520 A1 11/2009 Highley et al.
2009/0281530 A1 11/2009 Korn
2009/0291423 A1 11/2009 Hara
2010/0004580 A1 1/2010 Lynch et al.
2010/0036488 A1 2/2010 de Juan et al.
2010/0057072 A1 3/2010 Roman et al.
2010/0114309 A1 5/2010 de Juan et al.
2010/0121342 A1 5/2010 Schieber et al.
2010/0137981 A1 6/2010 Silvestrini et al.
2010/0173866 A1 7/2010 Hee et al.

(56) References Cited

U.S. PATENT DOCUMENTS

| | | | |
|---|---|---|---|
| 2010/0191176 | A1 | 7/2010 | Ho et al. |
| 2010/0191177 | A1 | 7/2010 | Chang et al. |
| 2010/0222733 | A1 | 9/2010 | Schieber et al. |
| 2010/0234726 | A1 | 9/2010 | Sirimanne et al. |
| 2010/0234790 | A1 | 9/2010 | Tu et al. |
| 2010/0262174 | A1 | 10/2010 | Sretavan et al. |
| 2010/0324543 | A1 | 12/2010 | Kurtz et al. |
| 2010/0331858 | A1 | 12/2010 | Simaan et al. |
| 2011/0009874 | A1 | 1/2011 | Wardle et al. |
| 2011/0009958 | A1 | 1/2011 | Wardle et al. |
| 2011/0028948 | A1 | 2/2011 | Raksi et al. |
| 2011/0028949 | A1 | 2/2011 | Raksi et al. |
| 2011/0028950 | A1 | 2/2011 | Raksi et al. |
| 2011/0028951 | A1 | 2/2011 | Raksi et al. |
| 2011/0028952 | A1 | 2/2011 | Raksi et al. |
| 2011/0028953 | A1 | 2/2011 | Raksi et al. |
| 2011/0028954 | A1 | 2/2011 | Raksi et al. |
| 2011/0028955 | A1 | 2/2011 | Raksi |
| 2011/0028957 | A1 | 2/2011 | Raksi et al. |
| 2011/0028958 | A1 | 2/2011 | Raksi et al. |
| 2011/0098809 | A1 | 4/2011 | Wardle et al. |
| 2011/0196487 | A1 | 8/2011 | Badawi et al. |
| 2011/0218523 | A1 | 9/2011 | Robl |
| 2011/0224597 | A1 | 9/2011 | Stegmann et al. |
| 2011/0319806 | A1 | 12/2011 | Wardle |
| 2012/0010702 | A1 | 1/2012 | Stegmann et al. |
| 2012/0021397 | A1 | 1/2012 | Van Dalen et al. |
| 2012/0022424 | A1 | 1/2012 | Yamamoto et al. |
| 2012/0035524 | A1 | 2/2012 | Silvestrini |
| 2012/0136439 | A1 | 5/2012 | Schieber et al. |
| 2012/0179087 | A1 | 7/2012 | Schieber et al. |
| 2012/0191064 | A1 | 7/2012 | Conston et al. |
| 2012/0271272 | A1 | 10/2012 | Hammack et al. |
| 2012/0283557 | A1 | 11/2012 | Berlin |
| 2012/0302861 | A1 | 11/2012 | Marshall et al. |
| 2012/0323159 | A1 | 12/2012 | Wardle et al. |
| 2013/0006165 | A1 | 1/2013 | Euteneuer et al. |
| 2013/0023837 | A1 | 1/2013 | Becker |
| 2013/0079701 | A1 | 3/2013 | Schieber et al. |
| 2013/0150959 | A1 | 6/2013 | Schieber et al. |
| 2013/0158462 | A1 | 6/2013 | Wardle et al. |
| 2013/0172804 | A1 | 7/2013 | Schieber et al. |
| 2013/0182223 | A1 | 7/2013 | Wardle et al. |
| 2013/0184631 | A1 | 7/2013 | Pinchuk |
| 2013/0231603 | A1 | 9/2013 | Wardle et al. |
| 2013/0253402 | A1 | 9/2013 | Badawi et al. |
| 2013/0253403 | A1 | 9/2013 | Badawi et al. |
| 2013/0253437 | A1 | 9/2013 | Badawi et al. |
| 2013/0253438 | A1 | 9/2013 | Badawi et al. |
| 2013/0253528 | A1 | 9/2013 | Haffner et al. |
| 2013/0267887 | A1 | 10/2013 | Kahook et al. |
| 2013/0281907 | A1 | 10/2013 | Wardle et al. |
| 2013/0281908 | A1 | 10/2013 | Schaller et al. |
| 2013/0331761 | A1 | 12/2013 | Euteneuer et al. |
| 2013/0338563 | A1 | 12/2013 | Schieber et al. |
| 2014/0018720 | A1 | 1/2014 | Horvath et al. |
| 2014/0066821 | A1 | 3/2014 | Freidland et al. |
| 2014/0066831 | A1 | 3/2014 | Silvestrini et al. |
| 2014/0081195 | A1 | 3/2014 | Clauson et al. |
| 2014/0114229 | A1 | 4/2014 | Wardle et al. |
| 2014/0121584 | A1 | 5/2014 | Wardle et al. |
| 2014/0214161 | A1 | 7/2014 | Schieber et al. |
| 2014/0249463 | A1 | 9/2014 | Wardle et al. |
| 2014/0323944 | A1 | 10/2014 | Schieber et al. |
| 2015/0018746 | A1 | 1/2015 | Hattenbach |
| 2015/0022780 | A1 | 1/2015 | John et al. |
| 2015/0038893 | A1 | 2/2015 | Haffner et al. |
| 2015/0045714 | A1 | 2/2015 | Horvath et al. |
| 2015/0057583 | A1 | 2/2015 | Gunn et al. |
| 2015/0057591 | A1 | 2/2015 | Horvath et al. |
| 2015/0065940 | A1 | 3/2015 | Rangel-Friedman et al. |
| 2015/0119787 | A1 | 4/2015 | Wardle et al. |
| 2015/0148836 | A1 | 5/2015 | Heeren |
| 2015/0223983 | A1 | 8/2015 | Schieber et al. |
| 2015/0223984 | A1 | 8/2015 | Schieber et al. |
| 2015/0223985 | A1 | 8/2015 | Schieber et al. |
| 2015/0250649 | A1 | 9/2015 | Euteneuer et al. |
| 2015/0282982 | A1 | 10/2015 | Schieber et al. |
| 2015/0290033 | A1 | 10/2015 | Wardle et al. |
| 2015/0305939 | A1 | 10/2015 | Vera et al. |
| 2015/0305940 | A1 | 10/2015 | Vera et al. |
| 2015/0313759 | A1 | 11/2015 | Vera et al. |
| 2015/0366710 | A1 | 12/2015 | Schieber et al. |
| 2016/0063898 | A1 | 3/2016 | Bernal |
| 2016/0250072 | A1 | 9/2016 | Wardle et al. |
| 2017/0127941 | A1 | 5/2017 | Ostermeier et al. |
| 2017/0143541 | A1 | 5/2017 | Badawi et al. |
| 2017/0156848 | A1 | 6/2017 | Schieber |
| 2017/0164831 | A1 | 6/2017 | Choo et al. |
| 2017/0172794 | A1 | 6/2017 | Varner et al. |
| 2017/0172795 | A1 | 6/2017 | Lerner |
| 2017/0172797 | A1 | 6/2017 | Horvath et al. |
| 2017/0172798 | A1 | 6/2017 | Horvath et al. |
| 2017/0172799 | A1 | 6/2017 | Horvath |
| 2017/0172800 | A1 | 6/2017 | Romoda et al. |
| 2017/0202708 | A1 | 7/2017 | Berlin |
| 2017/0239272 | A1 | 8/2017 | Ambati et al. |
| 2017/0251921 | A1 | 9/2017 | Phan et al. |
| 2017/0252212 | A1 | 9/2017 | Eutenuer et al. |
| 2017/0281409 | A1 | 10/2017 | Haffner et al. |
| 2017/0290705 | A1 | 10/2017 | Wardle et al. |
| 2017/0360609 | A9 | 12/2017 | Schieber et al. |
| 2018/0369017 | A1 | 12/2018 | Schieber et al. |
| 2019/0076296 | A1 | 3/2019 | Van Meter et al. |
| 2020/0085620 | A1 | 3/2020 | Euteneuer et al. |
| 2020/0197221 | A1 | 6/2020 | Schieber et al. |
| 2020/0261270 | A1 | 8/2020 | Berlin |
| 2021/0330499 | A1 | 10/2021 | Wardle et al. |
| 2021/0361479 | A1 | 11/2021 | Wardle et al. |
| 2022/0054314 | A1 | 2/2022 | Van Meter et al. |
| 2022/0096271 | A1 | 3/2022 | Wardle et al. |

FOREIGN PATENT DOCUMENTS

| | | | |
|---|---|---|---|
| DE | 4226476 | C1 | 8/1993 |
| DE | 19840047 | A1 | 3/2000 |
| DE | 102012221350 | A1 | 5/2014 |
| EP | 0168201 | B1 | 6/1988 |
| EP | 0957949 | A1 | 11/1996 |
| EP | 0766544 | B1 | 5/1998 |
| EP | 1615604 | B1 | 8/2009 |
| EP | 2193821 | A1 | 6/2010 |
| EP | 1715827 | B1 | 12/2010 |
| EP | 2380622 | A1 | 10/2011 |
| EP | 2468327 | A1 | 6/2012 |
| EP | 2471563 | A1 | 7/2012 |
| EP | 1833440 | B1 | 8/2012 |
| EP | 3164061 | A1 | 5/2017 |
| EP | 2996648 | B1 | 6/2017 |
| EP | 1732484 | B1 | 8/2017 |
| EP | 1740153 | B2 | 8/2017 |
| EP | 3076948 | A4 | 8/2017 |
| EP | 3205333 | A1 | 8/2017 |
| EP | 3060180 | A4 | 9/2017 |
| EP | 3082570 | A4 | 9/2017 |
| JP | 10504978 | A | 5/1998 |
| JP | 11123205 | A | 5/1999 |
| JP | 2002541976 | A | 12/2002 |
| JP | 2002541977 | A | 12/2002 |
| JP | 2002542872 | A | 12/2002 |
| JP | 2006517848 | A | 8/2006 |
| JP | 2006289075 | A | 10/2006 |
| JP | 2009523545 | A | 6/2009 |
| JP | 2010509003 | A | 3/2010 |
| JP | 2011502649 | A | 1/2011 |
| JP | 2012527318 | A | 11/2012 |
| JP | 2015517836 | A | 6/2015 |
| JP | 2017517363 | A | 6/2017 |
| WO | WO 1996/006582 | | 3/1996 |
| WO | WO96/20742 | A1 | 7/1996 |
| WO | WO99/01063 | A1 | 1/1999 |
| WO | WO99/45868 | A1 | 9/1999 |
| WO | WO00/07525 | A1 | 2/2000 |
| WO | WO00/13627 | A1 | 3/2000 |

(56) References Cited

FOREIGN PATENT DOCUMENTS

| | | |
|---|---|---|
| WO | WO00/64389 A1 | 11/2000 |
| WO | WO00/64393 A1 | 11/2000 |
| WO | WO00/67687 A1 | 11/2000 |
| WO | WO 2000/066007 | 11/2000 |
| WO | WO01/89437 A2 | 11/2001 |
| WO | WO01/97727 A1 | 12/2001 |
| WO | WO02/36052 A1 | 5/2002 |
| WO | WO02/074052 A2 | 9/2002 |
| WO | WO02/080811 A2 | 10/2002 |
| WO | WO03/015659 A2 | 2/2003 |
| WO | WO03/045290 A1 | 6/2003 |
| WO | WO 2002/080811 | 3/2004 |
| WO | WO2004/054643 A1 | 7/2004 |
| WO | WO 2004/073552 | 9/2004 |
| WO | WO2004/093761 A1 | 11/2004 |
| WO | WO2005/105197 A2 | 11/2005 |
| WO | WO 2005/110424 | 11/2005 |
| WO | WO2006/066103 A2 | 6/2006 |
| WO | WO2007/035356 A2 | 3/2007 |
| WO | WO2007/047744 A2 | 4/2007 |
| WO | WO2007/087061 A2 | 8/2007 |
| WO | WO2008/002377 A1 | 1/2008 |
| WO | WO2008/005873 A2 | 1/2008 |
| WO | WO 2008/061043 | 5/2008 |
| WO | WO 2009/061988 | 5/2009 |
| WO | WO2009/120960 A2 | 10/2009 |
| WO | WO2011/053512 A1 | 5/2011 |
| WO | WO2011/057283 A1 | 5/2011 |
| WO | WO2011/106781 A1 | 9/2011 |
| WO | WO2011/150045 A1 | 12/2011 |
| WO | WO2012/051575 A2 | 4/2012 |
| WO | WO2012/083143 A1 | 6/2012 |
| WO | WO2013/147978 A2 | 10/2013 |
| WO | WO2016/154066 A2 | 9/2016 |
| WO | WO2017/030902 A2 | 2/2017 |
| WO | WO2017/030917 A1 | 2/2017 |
| WO | WO2017/062347 A1 | 4/2017 |
| WO | WO2017/087713 A1 | 5/2017 |
| WO | WO2017/095825 A1 | 6/2017 |
| WO | WO2017/132418 A1 | 8/2017 |
| WO | WO2017/132647 A1 | 8/2017 |

OTHER PUBLICATIONS

Schieber et al.; U.S. Appl. No. 16/828,054 entitled "Methods and devices for increasing aqueous humor outflow," filed Mar. 24, 2020.

Noda et al.; U.S. Appl. No. 17/572,064 entitled "Systems and methods for viscoelastic delivery," filed Jan. 10, 2022.

Bahler, et al.; Trabecular bypass stents decrease intraocular pressure in cultured human anterior segments; Amer. Journal of Ophthalmology; vol. 138, No. 6; pp. 988-994.e2; Dec. 2004.

Cambridge Dictionary; Sensor (definition); 2 pages; retrived from the internet (http://dictionary.cambridge.org/define.asp?dict=CALD &key=71811 >) on Aug. 14, 2018.

Camras et al.; A novel schlemm's canal scaffold increases outflow facility in a human anterior segment perfusion model; Invest. Opthalmol. Vis. Sci. ; 53(10); pp. 6115-6121; Sep. 1, 2012.

D'Ermo, et al.; Our results with the operation of ab externo trabeculotomy; Ophthalmologica; vol. 163; pp. 347-355; Feb. 1971.

Dietlein et al.; Morphological variability of the trabecular meshwork in glaucoma patients: implications for non-perforating glaucoma surgery; British Journal of Ophthalmology; 84(12); pp. 1354-1359; Dec. 2000.

Ellingsen et al.; Trabeculotomy and sinusotomy in enucleated human eyes; Investigative Ophthalmology; vol. 11; pp. 21-28; Jan. 1972.

Grant; Experimental aqueous perfusion in enucleated human eyes; Archives of Ophthalmology; vol. 69; pp. 783-801; Jun. 1963.

Gulati et al; A novel 8-mm schlemm's canal scaffold reduces outflow resistance in a human anterior segment perfusion model; Invest. Ophthalmol. Vis. Sci.; 54(3); pp. 1698-1704; Mar. 5, 2013.

Hays et al.; Improvement in outflow facility by two novel microinvasive glaucoma surgery implants; Invest. Ophthalmol. Vis. Sci.; 55(3); pp. 1893-1900; Mar. 1, 2014.

Huang et al.; Optical coherence tomography; Science; 254(5035); pp. 1178-1181; 12 pages (Author Manuscript); Nov. 1991.

Johnstone et al.; "Microsurgery of Schlemm's Canal and the Human Aqueous Outflow System;" American Journal of Ophthalmology, vol. 76 (6): 906-917; Dec. 1973.

Johnstone et al.; Effects of a schlemm canal scaffold on collector channel ostia in human anterior segments; Exp. Eye. Res.; 119; pp. 70-76; Feb. 2014.

Johnstone; Aqueous humor outflow system overview; Becker-Shaffer's Diagnosis and Therapy of the Glaucomas; Part 2 Aqueous Humor Dynamics; Chapter 3; pp. 25-46; Mosby Elseveir; (year of pub. sufficiently earlier than effective US filing date and any foreign priority date) 2009.

Kirkness et al.; The Use of Silicone Drainage Tubing to Control Post-Keratoplasty Glaucoma; Eye; 2 (pt 5); pp. 583-590; Apr. 1988.

Lee et al.; Aqueous-venous shunt and intraocular pressure. Preliminary report of animal studies; Investigative Ophthalmology; vol. 5; No. 1; pp. 59-64; Feb. 1966.

Lee et al.; Short-pulsed neodymium-YAG laser trabeculotomy. An in vivo morphological study in the human eye; Investigative Ophthalmology and Visual Science; 29(11); pp. 1698-1707; Nov. 1988.

Lynch, Mary G.; U.S. Appl. No. 60/131,030 entitled "Devices and methods for treating glaucoma by enhancing aqueous outflow through schlemm's canal and anterior chamber angle," filed Apr. 26, 1999.

Macmilla Online Dictionary; Detector (definition); Macmilla On Line Dictionary; 2 pages; retrived from the internet (https://www.macmillandictionary.com/dictionary/british/detector) on Aug. 14, 2018.

Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.

Molteno et al.; Long Tube Implants in the Management of Glaucoma; SA Medical Journal; 26; pp. 1062-1066; Jun. 1976.

Molteno; New implant for drainage in glaucoma; Brit. J. Ophthal; 53; pp. 606-615; Sep. 1969.

Moses, Robert; The effect of intraocular pressure on resistance to outflow; Survey of Ophthalmology; vol. 22; No. 2; pp. 88-100; Sep.-Oct. 1977.

Nakamura et al.; Femtosecond laser photodisruption of primate trabecular meshwork: an ex vivo study; Investigative Ophthalmology and Visual Science; 50(3); pp. 1198-1204; Mar. 2009.

Owen; A moving-mirror gonioscope for retinal surgery; British Journal of Ophthalmology; 61(3); pp. 246-247; Mar. 1977.

Oxford Dictionaries; Detector (definition); 1 page; retrieved from the internet (https://en.oxforddictionaries.com/definition/detector) on Aug. 14, 2018.

Oxford Dictionaries; Sensor (definition); 1 page; retrieved from te internet (http://www.askoxford.com/concise_oed/sensor?view=uk>) on Aug. 14, 2018.

Radhakrishnan et al.; Real-time optical coherence tomography of the anterior segment at 1310 nm; Archives of Opthhalmology; 119(8); pp. 1179-1185; Aug. 2001.

Rosenquist et al.; Outflow resistance of enucleated human eyes at two different perfusion pressures and different extents of trabeculotomy; Current Eye Res.; vol. 8; No. 12; pp. 1233-1240; Dec. 1989.

Savage, James; Gonioscopy in the management of glaucoma; Am. Academy of Ophthalmology; Focal Points; vol. XXIV; No. 3; pp. 1-14; Mar. 2006.

Schocket et al.; Anterior Chamber Tube Shunt to an Encircling Band in the Treatment of Neovascular Glaucoma and other Refractory Glaucomas; Ophthalmology; 92; pp. 553-562; Apr. 1985.

Schultz, Jared; Canaloplasty procedure shows promise for open-angle glaucoma in European study; Ocular Surgery News; vol. 34; Mar. 1, 2007.

Smit et al.; Effects of viscoelastic injection into schlemm's canal in primate and human eyes; J. Am. Academy of Ophthalmology; vol. 109; No. 4; pp. 786-792; Apr. 2002.

(56) References Cited

OTHER PUBLICATIONS

Spiegel et al.; Schlemm's canal implant: a new method to lower intraocular pressure in patients with POAG?; Ophthalmic Surgery and Lasers; vol. 30; No. 6; pp. 492-494; Jun. 1999.
Toyran et al.; Femtosecond laser photodisruption of human trabecular meshwork: an in vitro study; Experimental Eye Research; 81(3); pp. 298-305; Sep. 2005.
Wilcox et al.; Hypothesis for Improving Accessory Filtration by Using Geometry; Journal of Glaucoma; 3; pp. 244-247; Fall 1994.
Berlin; U.S. Appl. No. 16/525,267 entitled "Delivery system and method of use for the eye," filed Jul. 29, 2019.
Wardle et al.; U.S. Appl. No. 16/520,139 entitled "Ocular implants and methods for delivering ocular implants into the eye," filed Jul. 23, 2019.
Sugiyama et al.; Micro-Diaphragm Pressure Sensor; 1986 International Electron Devices Meeting; pp. 184-187; Dec. 7, 1986.
Blanda et al.; U.S. Appl. No. 16/967,376 entitled "Occular implant and delivery system," filed Aug. 4, 2020.

* cited by examiner

METHOD OF IMPLANTING AN OCULAR IMPLANT

CROSS REFERENCE TO RELATED APPLICATIONS

This application is a continuation of U.S. application Ser. No. 15/012,544, filed Feb. 1, 2016, which claims the benefit under 35 U.S.C. § 119 of U.S. Application No. 62/110,293, filed Jan. 30, 2015 and is a continuation-in-part of U.S. application Ser. No. 14/691,267, filed Apr. 20, 2015 (now U.S. Pat. No. 9,610,196), which is a continuation of U.S. application Ser. No. 14/246,363, filed Apr. 7, 2014 (now U.S. Pat. No. 9,039,650), which is a continuation of U.S. application Ser. No. 12/236,225, filed Sep. 23, 2008 (now U.S. Pat. No. 8,734,377), which is a continuation-in-part of U.S. application Ser. No. 11/860,318, filed Sep. 24, 2007 (now U.S. Pat. No. 7,740,604).

Said U.S. application Ser. No. 15/012,544 is also a continuation-in-part of U.S. application Ser. No. 14/932,658, filed Nov. 4, 2015 (now U.S. Pat. No. 10,406,025, which is a continuation of U.S. application Ser. No. 13/865,770, filed Apr. 18, 2013 (now U.S. Pat. No. 9,211,213), which is a continuation of U.S. application Ser. No. 12/833,863, filed Jul. 9, 2010 (now U.S. Pat. No. 8,425,449), which claims the benefit under 35 U.S.C. § 119 of U.S. Application No. 61/224,158, filed Jul. 9, 2009. The disclosures of the preceding patent applications are incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to devices that are implanted within the eye. More particularly, the present invention relates to devices that facilitate the transfer of fluid from within one area of the eye to another area of the eye.

BACKGROUND

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," Investigative Ophthalmology (February 1966)). Other early glaucoma treatment implants led from the anterior chamber to a sub-conjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" Ophthalmic Surgery and Lasers (June 1999); U.S. Pat. Nos. 6,450,984; 6,450,984). In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," Investigative Ophthalmology (February 1966)). Other early glaucoma treatment implants led from the anterior chamber to a sub-conjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" Ophthalmic Surgery and Lasers (June 1999); U.S. Pat. Nos. 6,450,984; 6,450,984).

SUMMARY OF THE DISCLOSURE

This disclosure pertains to an ocular implant comprising a longitudinally extending body having an inlet portion and a Schlemm's canal portion distal to the inlet portion, the inlet portion being configured to extend into and be in fluid communication with an anterior chamber of a human eye and the Schlemm's canal portion being configured to be inserted into Schlemm's canal adjacent to collector channels of the eye, a plurality of alternating spines and frames positioned longitudinally along at least a portion of the Schlemm's canal portion wherein the plurality of alternating spines and frames define a central channel extending therethrough, with the central channel being in fluid communication with the inlet portion, each of the spines having edges partially defining an opening across from the central channel and in fluid communication with the central channel, and each of the frames including first and second struts, the first and second struts each having an edge contiguous with an edge of an adjacent spine, the edges defining the opening in fluid communication with the central channel, wherein the ocular implant is configured to provide at least a 121% increase in average outflow facility of aqueous humor from the anterior chamber through the collector channels of the eye.

In some embodiments, the implant comprises at least three openings across from the central channel.

In other embodiments, the average outflow facility comprises 0.438 μl/min/mmHg.

In one embodiment, a peak circumferential flow rate through the ocular implant comprises 3.2 μl/min.

In some embodiments, the implant comprises at least six openings across from the central channel.

In one embodiment, the average outflow facility comprises 0.638 μl/min/mmHg.

In some embodiments, a peak circumferential flow rate through the ocular implant comprises 5.7 μl/min.

In one embodiment, the average outflow facility of the eye prior to implantation of the ocular implant comprises 0.138 μl/min/mmHg.

An ocular implant adapted to reside at least partially in a portion of Schlemm's canal of an eye adjacent to collector channels of the eye is provided, the implant comprising a longitudinally extending curved body including a proximal portion and a distal portion, the distal portion of the curved body defining a longitudinal channel including a channel opening, and the curved body being adapted and configured such that the distal portion of the curved body resides in Schlemm's canal and the proximal portion extends into the anterior space of the eye while the ocular implant assumes an orientation in which the channel opening is adjacent a major side of Schlemm's canal when the ocular implant is implanted, wherein the ocular implant is configured to provide a 121%-222% increase in average outflow facility of aqueous humor from the anterior chamber through the collector channels of the eye.

In some embodiments, the implant comprises at least three openings across from the central channel.

In other embodiments, the average outflow facility comprises 0.438 μl/min/mmHg.

In one embodiment, a peak circumferential flow rate through the ocular implant comprises 3.2 μl/min.

In some embodiments, the implant comprises at least six openings across from the central channel.

In one embodiment, the average outflow facility comprises 0.638 μl/min/mmHg.

In some embodiments, a peak circumferential flow rate through the ocular implant comprises 5.7 μl/min.

In one embodiment, the average outflow facility of the eye prior to implantation of the ocular implant comprises 0.138 μl/min/mmHg.

In one embodiment, the distal portion of the curved body occupies up to 20% of Schlemm's canal but accounts for up to 54.5% of total outflow in the eye.

In another embodiment, the distal portion of the curved body occupies up to 40% of Schlemm's canal but accounts for up to 74.6% of total outflow in the eye.

An ocular implant is provided comprising an inlet portion and a Schlemm's canal portion distal to the inlet portion, the inlet portion being disposed at a proximal end of the implant and sized and configured to be placed within an anterior chamber of a human eye, the inlet portion having an inlet adapted to be in fluid communication with the anterior chamber, the Schlemm's canal portion comprising a central channel in fluid communication with the inlet, the central channel extending longitudinally in the Schlemm's canal portion, a first element disposed along the central channel, a second element disposed along the central channel distal to the first element, a third element disposed along the central channel distal to the first element and proximal to the second, a fourth element disposed along the central channel distal to the second element, the first, second, third and fourth elements each comprising two edges partially defining an elongate opening in fluid communication with the central channel, each of the first, second, third and fourth elements having circumferential extents less than 360 degrees so that the elongate opening extends continuously along the first, second, third and fourth elements, the circumferential extents of the first and second elements being less than the circumferential extents of the third and fourth elements, the Schlemm's canal portion being arranged and configured to be disposed within Schlemm's canal of the eye when the inlet portion is disposed in the anterior chamber, wherein the ocular implant is configured to provide a 121%-222% increase in average outflow facility of aqueous humor from the anterior chamber through the collector channels of the eye.

In some embodiments, the implant comprises at least three openings across from the central channel.

In other embodiments, the average outflow facility comprises 0.438 μl/min/mmHg.

In one embodiment, a peak circumferential flow rate through the ocular implant comprises 3.2 μl/min.

In some embodiments, the implant comprises at least six openings across from the central channel.

In one embodiment, the average outflow facility comprises 0.638 μl/min/mmHg.

In some embodiments, a peak circumferential flow rate through the ocular implant comprises 5.7 μl/min.

In one embodiment, the average outflow facility of the eye prior to implantation of the ocular implant comprises 0.138 μl/min/mmHg.

In one embodiment, the distal portion of the curved body occupies up to 20% of Schlemm's canal but accounts for up to 54.5% of total outflow in the eye.

In another embodiment, the distal portion of the curved body occupies up to 40% of Schlemm's canal but accounts for up to 74.6% of total outflow in the eye.

A method of treating glaucoma is provided, comprising supporting tissue forming Schlemm's canal in an eye with an implant extending at least partially in the canal along an axial length within the canal, contacting with the implant less than 50% of the tissue forming the canal along the axial length, disposing an inlet portion of the implant in an anterior chamber of the eye, and providing fluid communication between the anterior chamber and the canal axially through the inlet into a channel of the implant such that an average outflow facility between the anterior chamber and the canal is increased by 121%-222%, and wherein the implant comprises open areas separated by spine areas along a first longitudinal section, the spine areas partially defining the channel, the supporting step comprising orienting the first longitudinal section openings towards a trabecular mesh portion of the canal.

An ocular implant adapted to reside at least partially in a portion of Schlemm's canal of a human eye is provided, the implant comprising a body configured to extend within Schlemm's canal in a curved volume having a large radius side and a short radius side, the body having a circumferential extent within the curved volume that varies along the length of the body between sections having a lesser circumferential extent and sections having a greater circumferential extent: wherein the body defines a channel extending longitudinally through the body, the channel having a substantially open side disposed on the large radius side at one of the sections of lesser circumferential extent and an adjacent section of greater circumferential extent and a plurality of openings along the length of the body on the short radius side, the openings being in fluid communication with the channel, and an inlet portion configured to be disposed in an anterior chamber of the eye when the body is in Schlemm's canal, the inlet portion disposed on a proximal end of the body in fluid communication with the channel, the inlet portion defining one or more openings in fluid communication with the anterior chamber of the eye, wherein the ocular implant is configured to provide a 121%-222% increase in average outflow facility of aqueous humor from the anterior chamber through the collector channels of the eye.

An ocular implant adapted to reside at least partially in a portion of Schlemm's canal of an eye, the eye having an iris defining a pupil is provided, the implant comprising a longitudinally extending curved body including a proximal portion and a distal portion, the distal portion of the curved body having a central longitudinal axis defined by a radius of curvature and a lateral cross section having a first lateral extent and a second lateral extent, an aspect ratio of the first lateral extent to the second lateral extent being greater than or equal to about two, the distal portion of the curved body defining a longitudinal channel including a channel opening, the channel opening included in defining the first lateral extent, the curved body being adapted and configured such that the distal portion of the curved body resides in Schlemm's canal and the proximal portion extends into the anterior space of the eye while the ocular implant assumes an orientation in which the channel opening is adjacent a major side of Schlemm's canal when the ocular implant is implanted, and wherein the ocular implant is configured to provide a 121%-222% increase in average outflow facility of aqueous humor from the anterior chamber through the collector channels of the eye.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
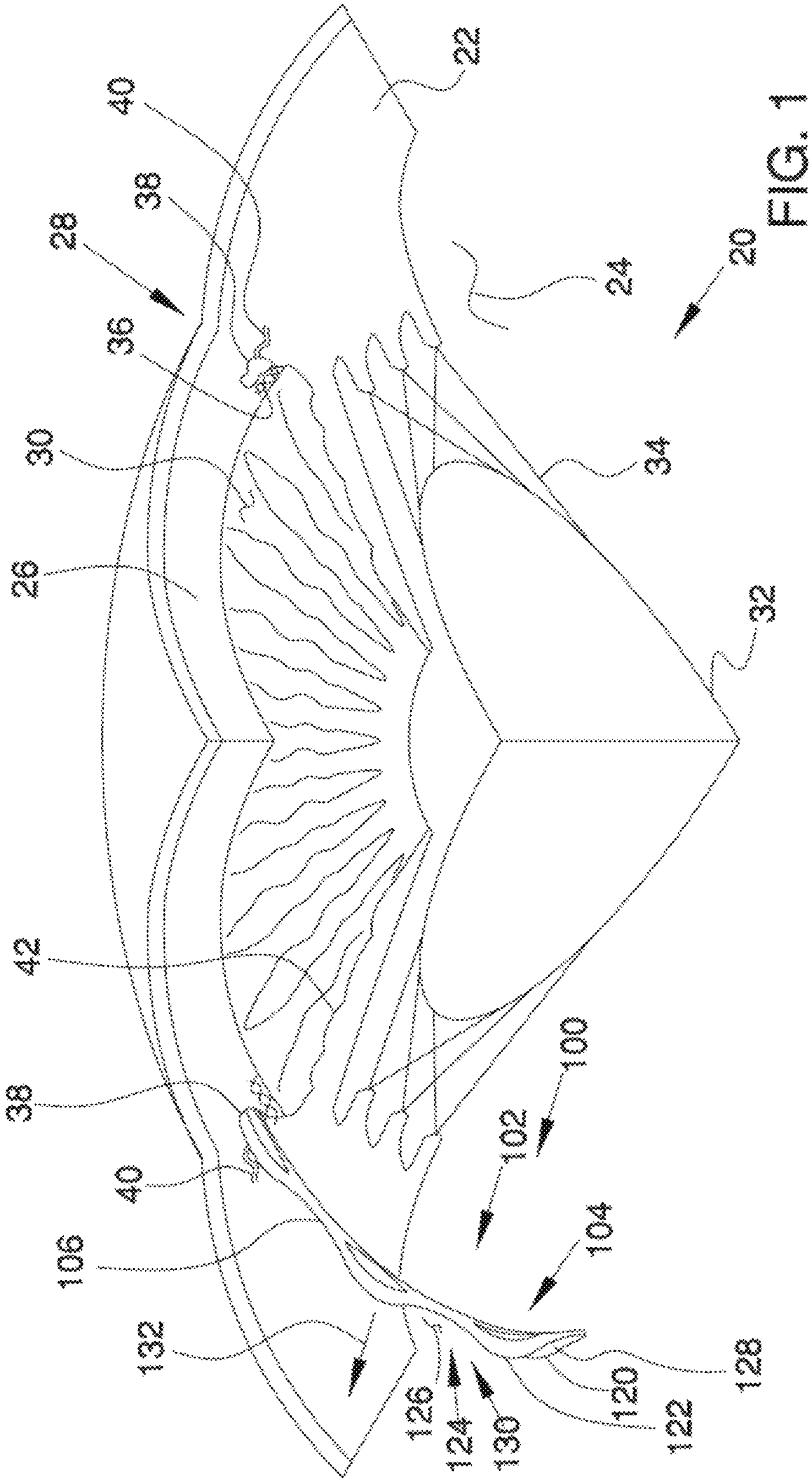
FIG. 1 is a stylized perspective view depicting a portion of a human eye and a portion of an ocular implant disposed in Schlemm's canal.

FIG. 1 is a stylized perspective view depicting a portion of a human eye 20. Eye 20 can be conceptualized as a fluid filled ball having two chambers. Sclera 22 of eye 20 surrounds a posterior chamber 24 filled with a viscous fluid known as vitreous humor. Cornea 26 of eye 20 encloses an anterior chamber 30 that is filled with a fluid know as aqueous humor. The cornea 26 meets the sclera 22 at a limbus 28 of eye 20. A lens 32 of eye 20 is located between anterior chamber 30 and posterior chamber 24. Lens 32 is held in place by a number of ciliary zonules 34.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

In a healthy eye, aqueous humor flows out of the anterior chamber 30 through the trabecular meshwork 36 and into Schlemm's canal 38, located at the outer edge of the iris 42. Aqueous humor exits Schlemm's canal 38 by flowing through a number of outlets 40. After leaving Schlemm's canal 38, aqueous humor is absorbed into the venous blood stream.

In FIG. 1, an ocular implant 100 is disposed in Schlemm's canal 38 of eye 20. Ocular implant 100 has a body 102 including a plurality of tissue supporting frames 104 and a plurality of spines 106. Body 102 also includes a first edge 120 and a second edge 122 that define a first opening 124. First opening 124 is formed as a slot and fluidly communicates with an elongate channel 126 defined by an inner surface 128 of body 102. With reference to FIG. 1, it will be appreciated that first opening 124 is disposed on an outer side 130 of body 102. Accordingly, channel 126 opens in a radially outward direction 132 via first opening 124.

Ocular implant 100 may be inserted into Schlemm's canal of a human eye to facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 100 will support trabecular mesh tissue and Schlemm's canal tissue and will provide for improved communication between the anterior chamber and Schlemm's canal (via the trabecular meshwork) and between pockets or compartments along Schlemm's canal. As shown in FIG. 1, the implant is preferably oriented so that the first opening 124 is disposed radially outwardly within Schlemm's canal.

Figure 2:
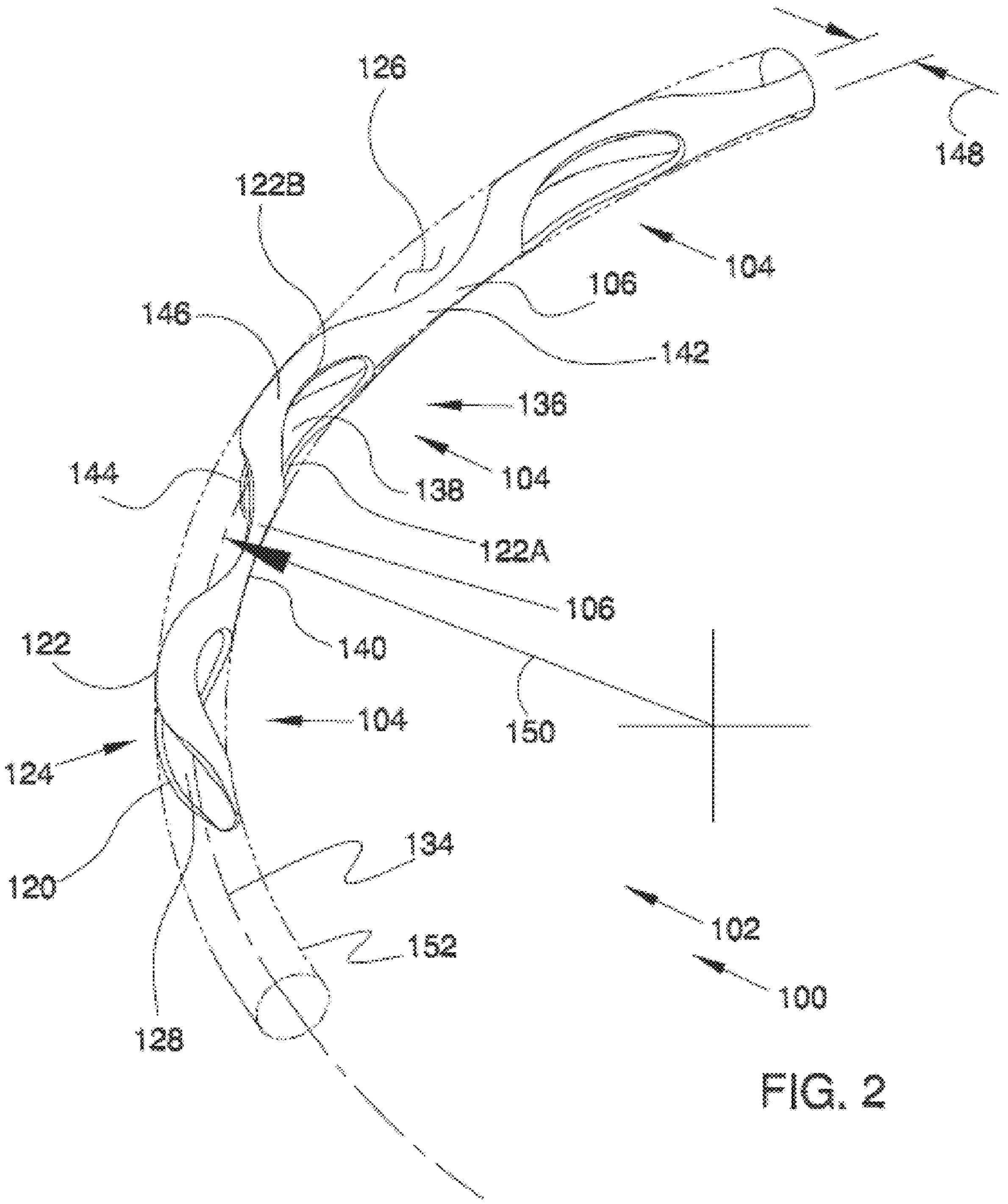
FIG. 2 is an enlarged perspective view showing a portion of the implant of FIG. 1.

FIG. 2 is an enlarged perspective view showing a portion of ocular implant 100 shown in the previous figure. Ocular implant 100 has a body 102 that extends along a generally curved longitudinal axis 134. Body 102 has a plurality of tissue supporting frames 104 and a plurality of spines 106. As shown in FIG. 2, these spines 106 and frames 104 are arranged in a repeating AB pattern in which each A is a tissue supporting frame and each B is a spine. In the embodiment of FIG. 2, one spine extends between each adjacent pair of frames 104

The frames 104 of body 102 include a first frame 136 of ocular implant 100 that is disposed between a first spine 140 and a second spine 142. In the embodiment of FIG. 2, first frame 136 is formed as a first strut 144 that extends between first spine 140 and second spine 142. First frame 136 also includes a second strut 146 extending between first spine 140 and second spine 142. In the exemplary embodiment of FIG. 2, each strut undulates in a circumferential direction as it extends longitudinally between first spine 140 and second spine 142.

In the embodiment of FIG. 2, body 102 has a longitudinal radius 150 and a lateral radius 148. Body 102 of ocular implant 100 includes a first edge 120 and a second edge 122 that define a first opening 124. First opening 124 fluidly communicates with an elongate channel 126 defined by an inner surface 128 of body 102. A second opening 138 is defined by a second edge 122A of a first strut 144 and a second edge 122B of a second strut 146. First opening 124, second opening 138 and additional openings defined by ocular implant 100 allow aqueous humor to flow laterally across and/or laterally through ocular implant 100. The outer surfaces of body 102 define a volume 152.

Figure 3:
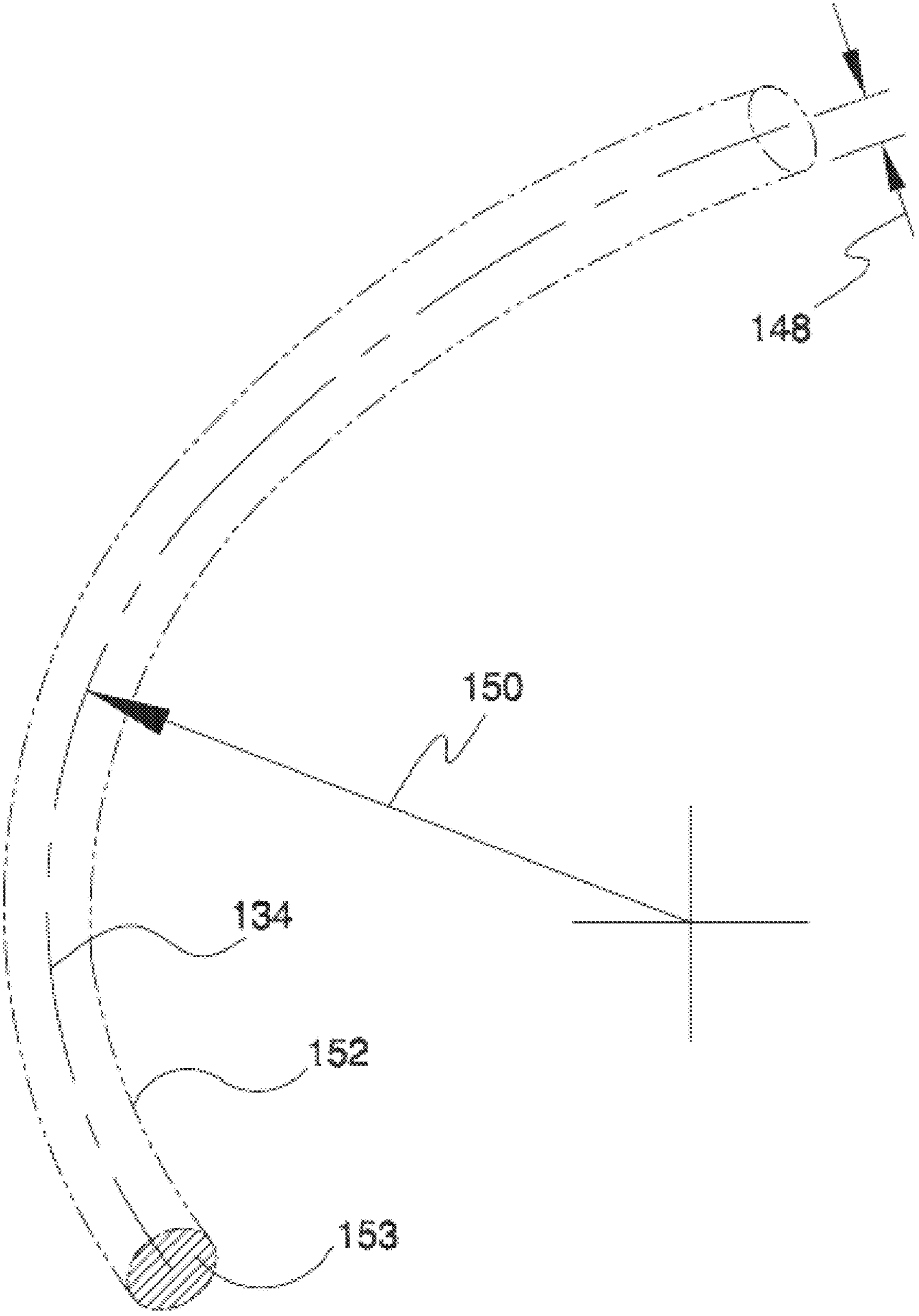
FIG. 3 is a perspective view showing a volume defined by the body of the ocular implant of FIGS. 1 and 2.

FIG. 3 is an additional perspective view showing volume 152 defined by the body of the ocular implant shown in the previous figure. With reference to FIG. 3, it will be appreciated that volume 152 extends along a generally curved longitudinal axis 134. Volume 152 has a longitudinal radius 150, a lateral radius 148, and a generally circular lateral cross section 153.

Figure 4:
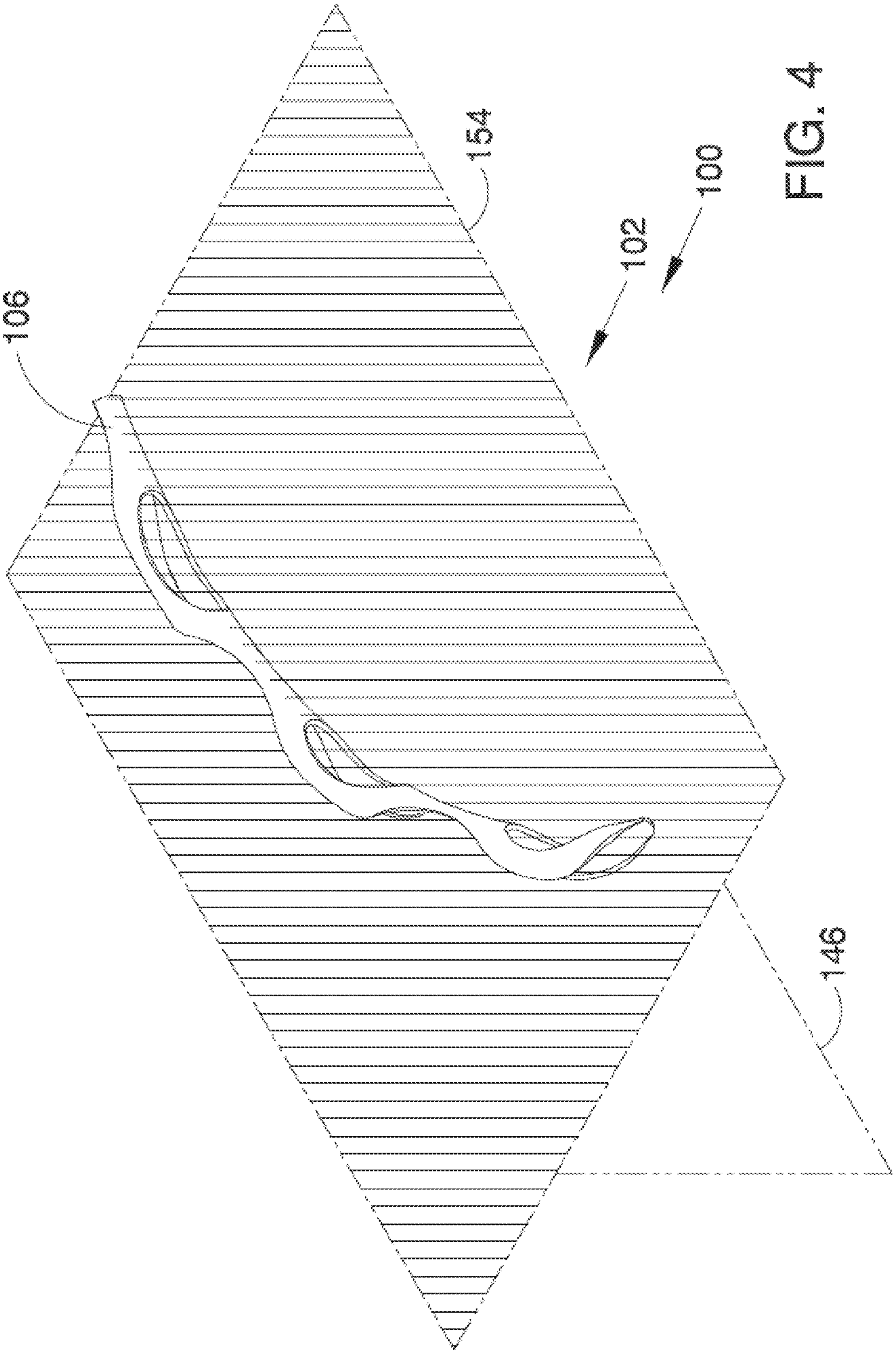
FIG. 4 is a perspective view showing a first plane intersecting the body of an ocular implant.

FIG. 4 is a perspective view showing a first plane 154 and a second plane 155 that both intersect ocular implant 100. In FIG. 4, first plane 154 is delineated with hatch marks. With reference to FIG. 4, it will be appreciated that spines 106 of body 102 are generally aligned with one another and that first plane 154 intersects all spines 106 shown in FIG. 4. In the embodiment of FIG. 4, body 102 of ocular implant 100 is generally symmetric about first plane 154.

In the embodiment of FIG. 4, the flexibility of body 102 is at a maximum when body 102 is bending along first plane 154, and body 102 has less flexibility when bending along a plane other than first plane 154 (e.g., a plane that intersects first plane 154). For example, in the embodiment shown in FIG. 4, body 102 has a second flexibility when bending along second plane 155 that is less than the first flexibility that body 102 has when bending along first plane 154.

Stated another way, in the embodiment of FIG. 4, the bending modulus of body 102 is at a minimum when body 102 is bent along first plane 154. Body 102 has a first bending modulus when bent along first plane 154 and a greater bending modulus when bent along a plane other than first plane 154 (e.g., a plane that intersects first plane 154). For example, in the embodiment shown in FIG. 4, body 102 has a second bending modulus when bent along second plane 155 that is greater than the first bending modulus that body 102 has when bent along first plane 154.

Figure 5:
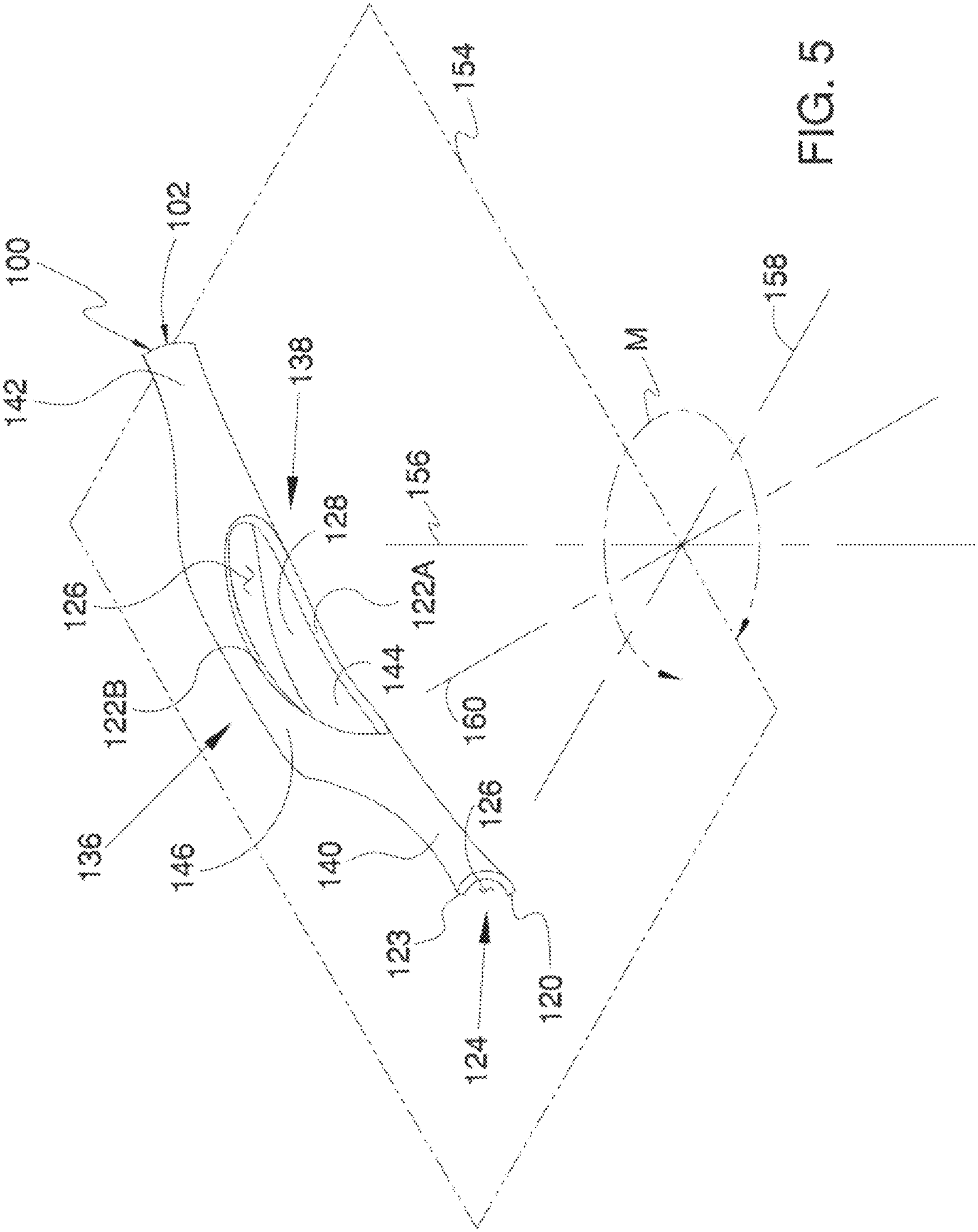
FIG. 5 is a perspective view showing a bending moment being applied to an ocular implant.

FIG. 5 is an enlarged perspective view showing a portion of ocular implant 100 shown in the previous figure. In the exemplary embodiment of FIG. 5, a bending moment M is being applied to body 102 of ocular implant 100. Bending moment M acts about a first axis 156 that is generally orthogonal to first plane 154. A second axis 158 and a third axis 160 are also shown in FIG. 5. Second axis 158 is generally perpendicular to first axis 156. Third axis 160 is skewed relative to first axis 156.

An inner surface 128 of body 102 defines a channel 126. Body 102 of ocular implant 100 includes a first edge 120 and a second edge 123 that define a first opening 124. Channel 126 of ocular implant 100 fluidly communicates with first opening 124. A second opening 138 is defined by a second edge 122A of a first strut 144 and a second edge 122B of a second strut 146. First opening 124, second opening 138 and additional openings defined by ocular implant 100 allow aqueous humor to flow laterally across and/or laterally through ocular implant 100.

As shown in FIG. 5, ocular implant 100 has a first spine 140 and a second spine 142. First strut 144 and a second strut 146 form a first frame 136 of ocular implant 100 that extends between first spine 140 and second spine 142. In the exemplary embodiment of FIG. 5, each strut undulates in a circumferential direction as it extends longitudinally between first spine 140 and second spine 142.

In the embodiment of FIG. 5, the flexibility of body 102 is at a maximum when body 102 is bent by a moment acting about first axis 156, and body 102 has less flexibility when bent by a moment acting about an axis other than first axis 156 (e.g., second axis 158 and third axis 160). Stated another way, the bending modulus of body 102 is at a minimum when body 102 is bent by a moment acting about first axis 156, and body 102 has a greater bending modulus when bent by a moment acting about an axis other than first axis 156 (e.g., second axis 158 and third axis 160).

Figure 6:
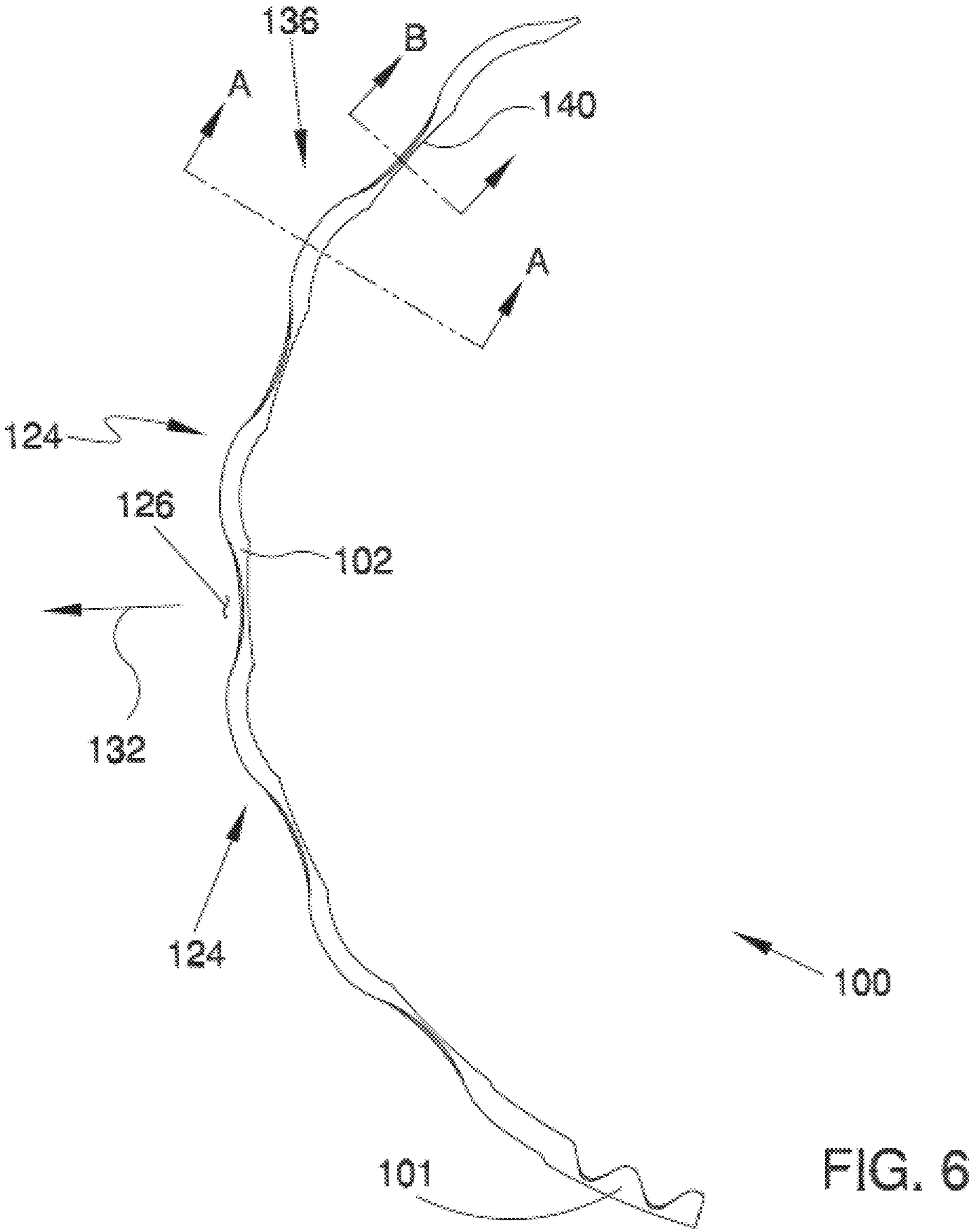
FIG. 6 is a plan view of the implant shown in FIG. 5 but in the absence of any bending moment.

FIG. 6 is a plan view showing ocular implant 100 shown in the previous figure. In the embodiment of FIG. 6, no external forces are acting on body 102 of ocular implant 100, and body 102 is free to assume the generally curved resting shape depicted in FIG. 6. Body 102 defines a first opening 124 that is disposed on an outer side 130 of body 102. A channel 126 is defined by the inner surface of body 102 and opens in a radially outward direction 132 via first opening 124.

Section lines A-A and B-B are visible in FIG. 6. Section line A-A intersects a first frame 136 of ocular implant 100. Section line B-B intersects a first spine 140 of ocular implant 100.

Figure 7A:
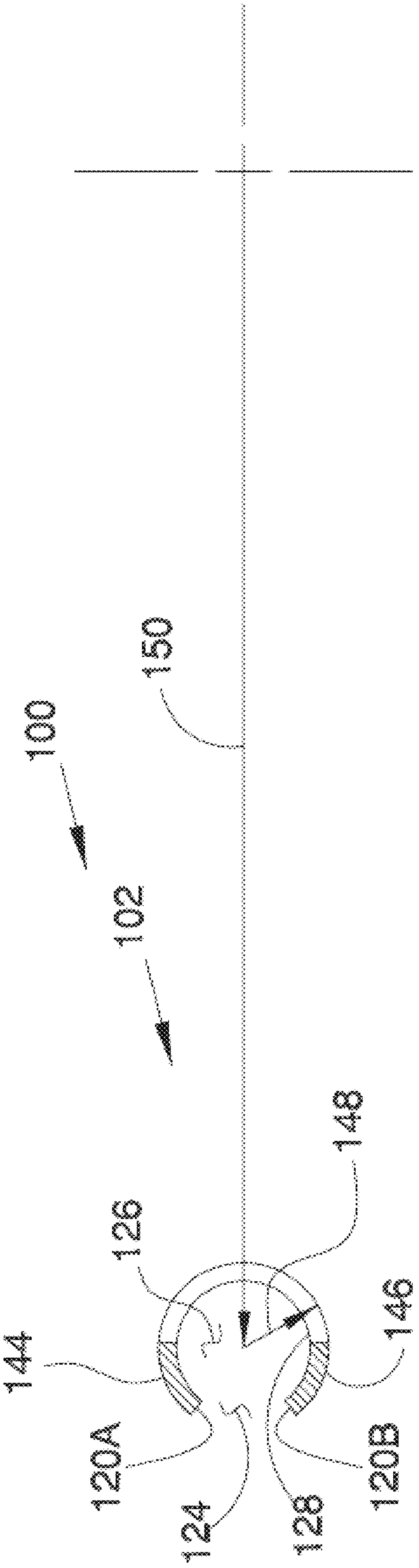
FIG. 7A is a lateral cross-sectional view of the ocular implant of FIG. 6 taken along section line A-A of FIG. 6.

FIG. 7A is a lateral cross-sectional view of ocular implant 100 taken along section line A-A shown in the previous figure. Section line A-A intersects a first strut 144 and a second strut 146 of first frame 136 at the point where the circumferential undulation of these struts is at its maximum. Body 102 of ocular implant 100 has a longitudinal radius 150 and a lateral radius 148. An inner surface 128 of body 102 defines a channel 126. A first opening 124 fluidly communicates with channel 126.

In FIG. 7A, first opening 124 in body 102 can be seen extending between first edge 120A of first strut 144 and a first edge 120B of second strut 146. With reference to FIG. 7A, it will be appreciated that second strut 146 has a shape that is a mirror image of the shape of first strut 144.

Figure 7B:
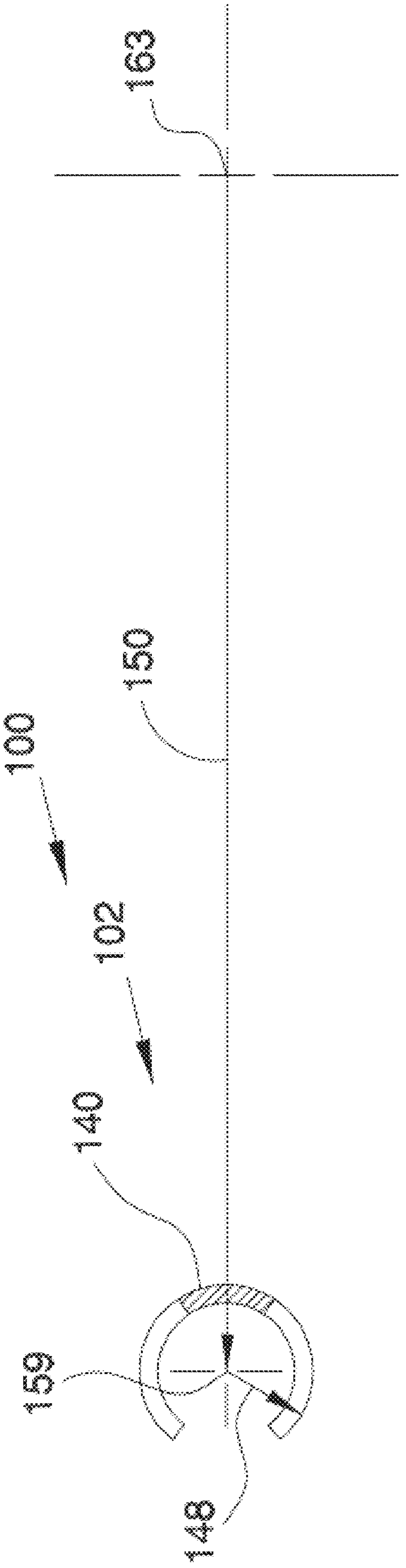
FIG. 7B is a lateral cross-sectional view of the ocular implant of FIG. 6 taken along section line B-B of FIG. 6.

FIG. 7B is a lateral cross-sectional view of ocular implant 100 taken along section line B-B shown in the previous figure. Section line B-B intersects first spine 140 of ocular implant 100. Body 102 has a longitudinal radius 150 and a lateral radius 148. In the embodiment of FIG. 7B, the center 159 of lateral radius 148 and the center 163 of longitudinal radius 150 are disposed on opposite sides of first spine 140. The center 159 of lateral radius 148 is disposed on a first side of first spine 140. The center 163 of longitudinal radius 150 is disposed on a second side of second spine 142.

Figure 8:
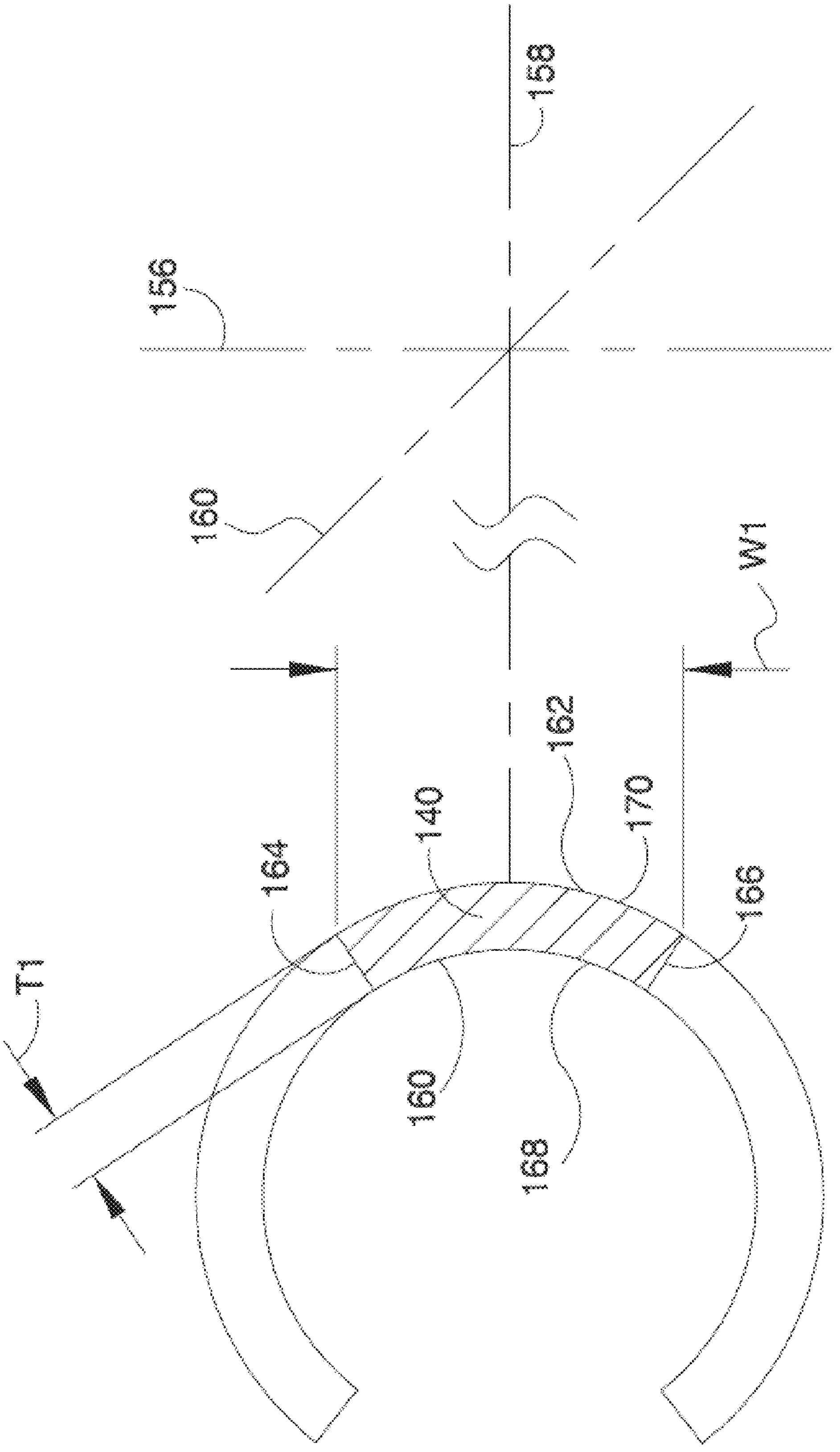
FIG. 8 is an enlarged cross-sectional view of the ocular implant of FIG. 6 taken along section line B-B of FIG. 6.

FIG. 8 is an enlarged cross-sectional view of ocular implant 100 taken along section line B-B of FIG. 6. First spine 140 includes a first major side 160, a second major side 162, a first minor side 164, and second minor side 166. With reference to FIG. 8, it will be appreciated that first major side 160 comprises a concave surface 168. Second major side 162 is opposite first major side 160. In the embodiment of FIG. 8, second major side 162 comprises a convex surface 170.

The geometry of the spine provides the ocular implant with flexibility characteristics that may aid in advancing the ocular implant into Schlemm's canal. In the embodiment of FIG. 8, first spine 140 has a thickness T1 extending between first major side 160 and second major side 162. Also in the embodiment of FIG. 8, first spine 140 has a width W1 extending between first minor side 164 and second minor side 166.

In some useful embodiments, the spine of an ocular implant in accordance with this detailed description has an aspect ratio of width W1 to thickness T1 greater than about 2. In some particularly useful embodiments, the spine of an ocular implant in accordance with this detailed description has an aspect ratio of width W1 to thickness T1 greater than about 4. In one useful embodiment, the ocular implant has a spine with an aspect ratio of width W1 to thickness T1 of about 5.2.

A first axis 156, a second axis 158 and a third axis 160 are shown in FIG. 8. Second axis 158 is generally perpendicular to first axis 156. Third axis 160 is skewed relative to first axis 156.

In the embodiment of FIG. 8, the flexibility of first spine 140 is at a maximum when first spine 140 is bent by a moment acting about first axis 156. First spine 140 has a first flexibility when bent by a moment acting about first axis 156 and less flexibility when bent by a moment acting about an axis other than first axis 156 (e.g., second axis 158 and third axis 160). For example, first spine 140 has a second flexibility when bent by a moment acting about second axis 158 shown in FIG. 8. This second flexibility is less than the first flexibility that first spine 140 has when bent by a moment acting about first axis 156.

In the embodiment of FIG. 8, the bending modulus of first spine 140 is at a minimum when first spine 140 is bent by a moment acting about first axis 156. First spine 140 has a first bending modulus when bent by a moment acting about first axis 156 and a greater bending modulus when bent by a moment acting about an axis other than first axis 156 (e.g., second axis 158 and third axis 160). For example, first spine 140 has a second bending modulus when bent by a moment acting about second axis 158 shown in FIG. 8. This second bending modulus is greater than the first bending modulus that first spine 140 has when bent by a moment acting about first axis 156.

Figure 9:
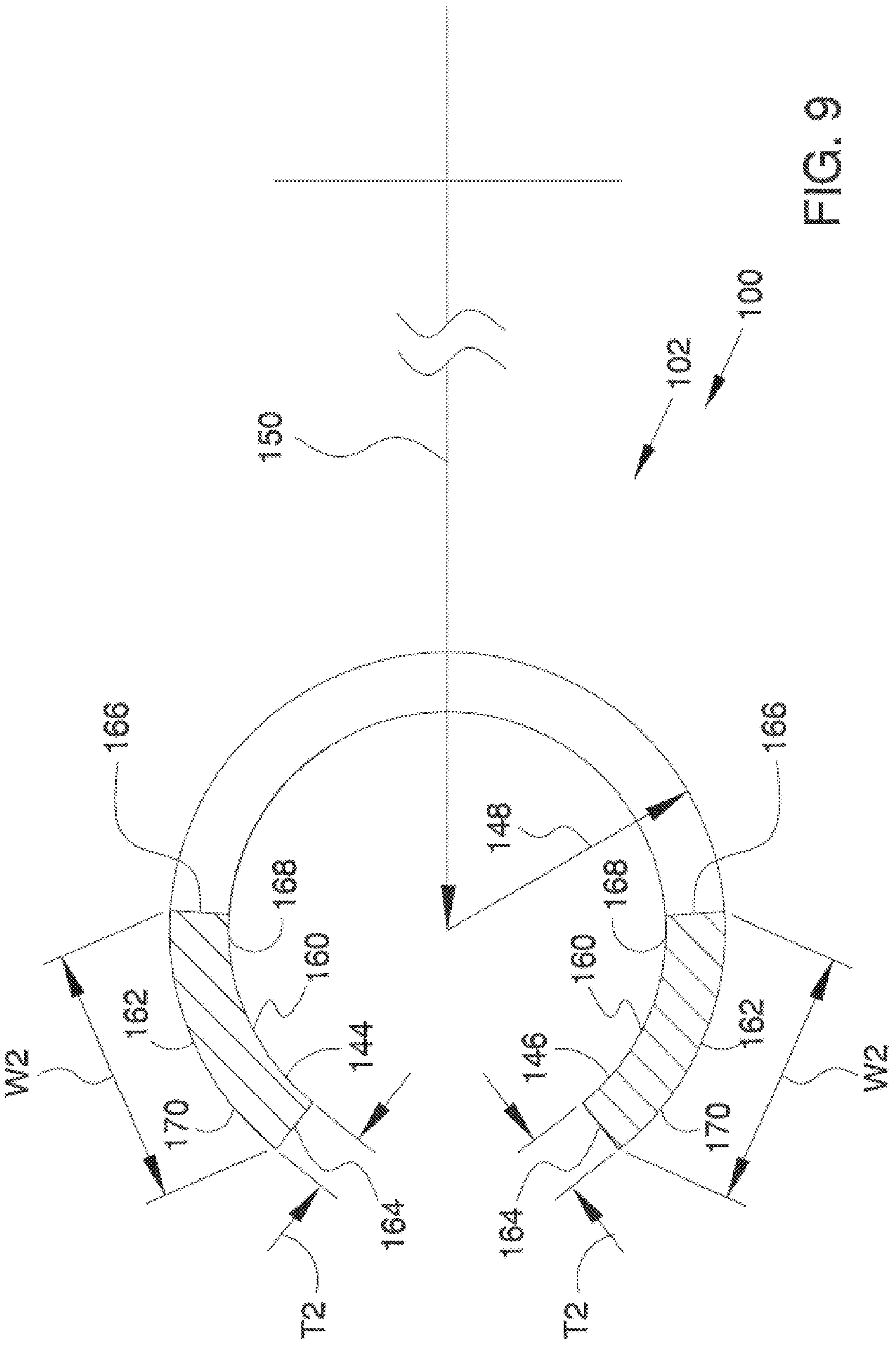
FIG. 9 is an enlarged cross-sectional view of the ocular implant of FIG. 6 taken along section line A-A of FIG. 6.

FIG. 9 is an enlarged cross-sectional view of ocular implant 100 taken along section line A-A of FIG. 6. Section line A-A intersects first strut 144 and second strut 146 at the point where the circumferential undulation of these struts is at its maximum.

Each strut shown in FIG. 9 includes a first major side 160, a second major side 162, a first minor side 164, and second minor side 166. With reference to FIG. 9, it will be appreciated that each first major side 160 comprises a concave surface 168 and each second major side 162 comprises a convex surface 170.

In the embodiment of FIG. 9, each strut has a thickness T2 extending between first major side 160 and second major side 162. Also in the embodiment of FIG. 9, each strut has a width W2 extending between first minor side 164 and second minor side 166. In some useful embodiments, an ocular implant in accordance with this detailed description includes spines having a width W1 that is greater than the width W2 of the struts of the ocular implant.

In some useful embodiments, the struts of an ocular implant in accordance with this detailed description have an aspect ratio of width W2 to thickness T2 greater than about 2. In some particularly useful embodiments, the struts of an ocular implant in accordance with this detailed description have an aspect ratio of width W2 to thickness T2 greater than about 4. One exemplary ocular implant has struts with an aspect ratio of width W2 to thickness T2 of about 4.4.

Body 102 of ocular implant 100 has a longitudinal radius 150 and a lateral radius 148. In some useful embodiments, an ocular implant in accordance with this detailed description is sufficiently flexible to assume a shape matching the longitudinal curvature of Schlemm's canal when the ocular implant advanced into the eye. Also in some useful embodiments, a length of the ocular implant is selected so that the implant will extend across a pre-selected angular span when the implant is positioned in Schlemm's canal. Examples of pre-selected angular spans that may be suitable in some applications include 60°, 90°, 150° and 180°. The diameter of an ocular implant in accordance with this detailed description may be selected so that the ocular implant is dimensioned to lie within and support Schlemm's canal. In some useful embodiments, the diameter of the ocular implant ranges between about 0.005 inches and about 0.04 inches. In some particularly useful embodiments, the diameter of the ocular implant ranges between about 0.005 inches and about 0.02 inches.

Figure 10:
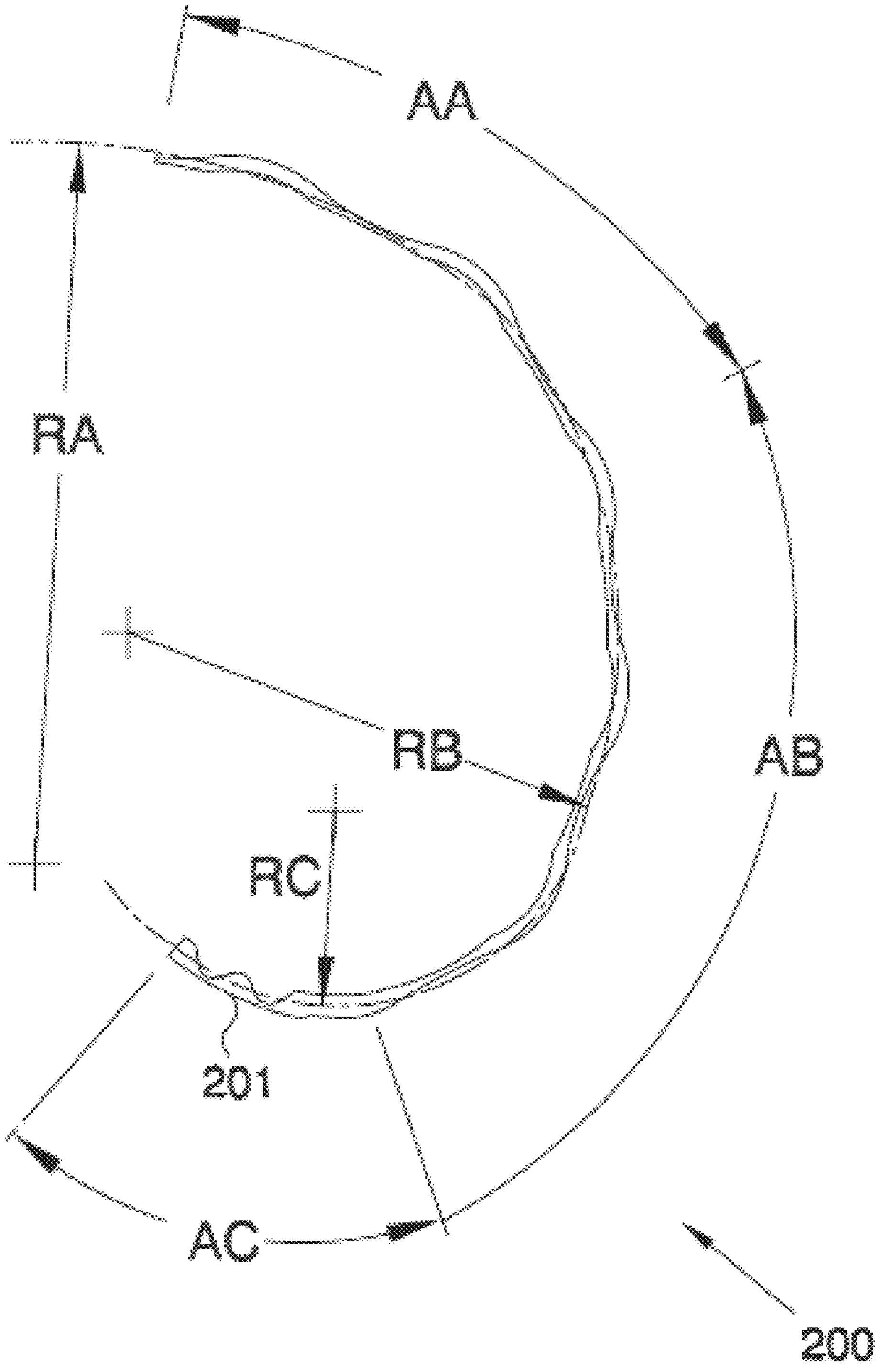
FIG. 10 is a plan view showing an ocular implant according to another embodiment of the invention having a longitudinal radius of curvature that varies along its length.
Figure 11:
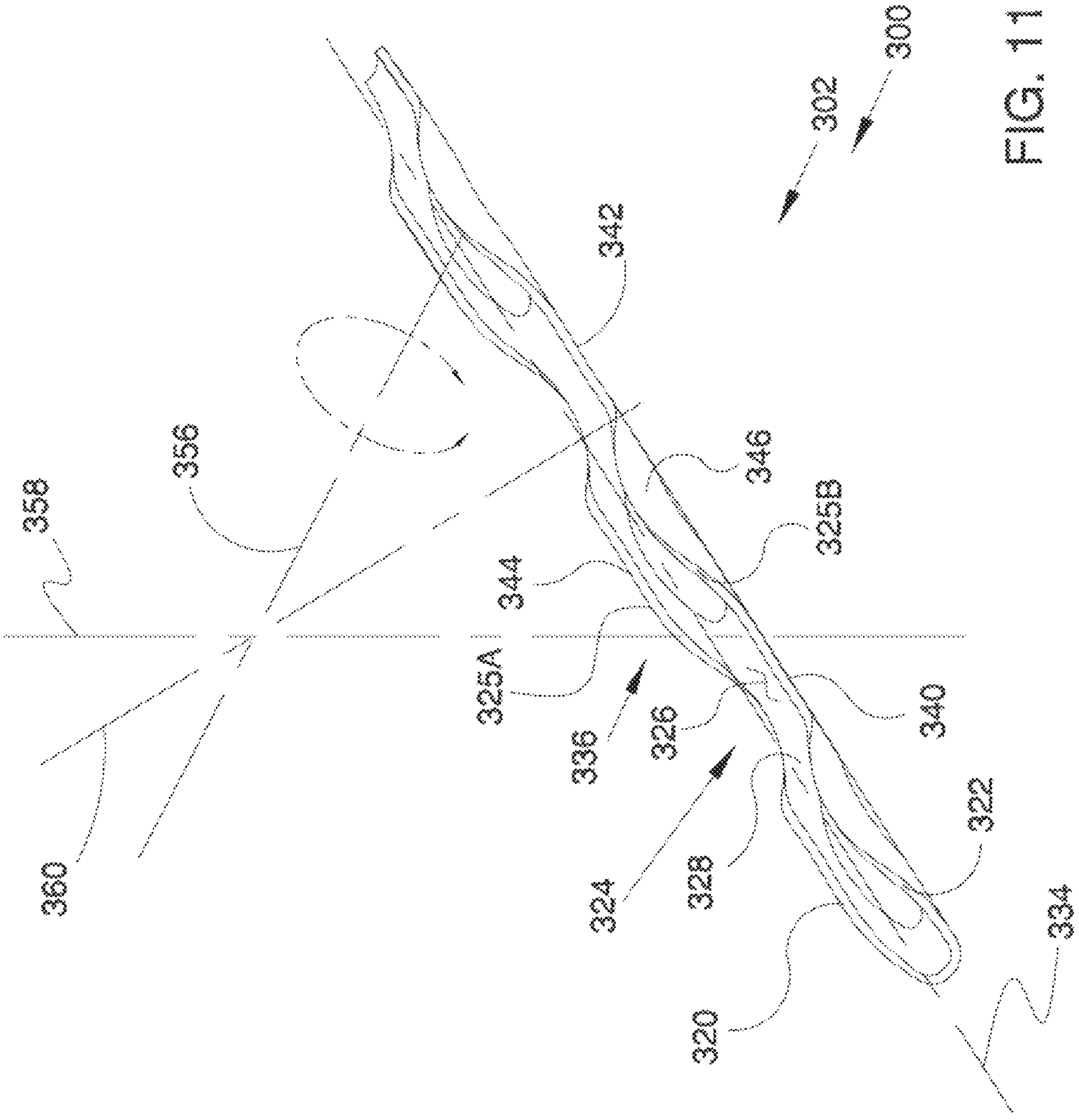
FIG. 11 is a perspective view showing an ocular implant according to yet another embodiment of the invention that has substantially no radius of curvature.

It is to be appreciated that an ocular implant in accordance with the present detailed description may be straight or curved. If the ocular implant is curved, it may have a substantially uniform longitudinal radius throughout its length, or the longitudinal radius of the ocular implant may vary along its length. FIG. 6 shows one example of an ocular implant having a substantially uniform radius of curvature. FIG. 10 shows one example of an ocular implant having a longitudinal radius of curvature that varies along the length of the ocular implant. An example of a substantially straight ocular implant is shown in FIG. 11.

FIG. 10 is a plan view showing an ocular implant 200 having a radius of curvature that varies along its length. In the embodiment of FIG. 10, ocular implant 200 has an at rest shape that is generally curved. This at rest shape can be established, for example, using a heat-setting process. The ocular implant shape shown in FIG. 10 includes a distal radius RA, a proximal radius RC, and an intermediate radius RB. In the embodiment of FIG. 10, distal radius RA is larger than both intermediate radius RB and proximal radius RC. Also in the embodiment of FIG. 10, intermediate radius RB is larger than proximal radius RC and smaller than distal radius RA. In one useful embodiment, distal radius RA is about 0.320 inches, intermediate radius RB is about 0.225 inches and proximal radius RC is about 0.205 inches.

In the embodiment of FIG. 10, a distal portion of the ocular implant follows an arc extending across an angle AA. A proximal portion of the ocular implant follows an arc extending across an angle AC. An intermediate portion of the ocular implant is disposed between the proximal portion and the distal portion. The intermediate portion extends across an angle AB. In one useful embodiment, angle AA is about 55 degrees, angle AB is about 79 degrees and angle AC is about 60 degrees.

Ocular implant 200 may be used in conjunction with a method of treating the eye of a human patient for a disease and/or disorder (e.g., glaucoma). Some such methods may include the step of inserting a core member into a lumen defined by ocular implant 200. The core member may comprise, for example, a wire or tube. The distal end of the ocular implant may be inserted into Schlemm's canal. The ocular implant and the core member may then be advanced into Schlemm's canal until the ocular implant has reached a desired position. In some embodiments, an inlet portion of the implant may be disposed in the anterior chamber of eye while the remainder of the implant extends through the trabecular mesh into Schlemm's canal. The core member may then be withdrawn from the ocular implant, leaving the implant in place to support tissue forming Schlemm's canal. Further details of ocular implant delivery systems may be found in U.S. application Ser. No. 11/943,289, filed Nov. 20, 2007, now U.S. Pat. No. 8,512,404, the disclosure of which is incorporated herein by reference.

The flexibility and bending modulus features of the ocular implant of this invention help ensure proper orientation of the implant within Schlemm's canal. FIG. 1 shows the desired orientation of opening 124 when the implant 100 is disposed in Schlemm's canal. As shown, opening 124 faces radially outward. The implant 100 is therefore designed so that it is maximally flexible when bent along a plane defined by the longitudinal axis of implant 100 as shown in FIG. 1, and less flexible when bent in other planes, thereby enabling the curved shape of Schlemm's canal to help place the implant in this orientation automatically if the implant is initially placed in Schlemm's canal in a different orientation.

FIG. 11 is a perspective view showing an ocular implant 300 in accordance with an additional embodiment in accordance with the present detailed description. With reference to FIG. 11, it will be appreciated that ocular implant 300 has a resting (i.e., unstressed) shape that is generally straight. Ocular implant 300 extends along a longitudinal axis 334 that is generally straight. In some useful embodiments, ocular implant 300 is sufficiently flexible to assume a curved shape when advanced into Schlemm's canal of an eye.

Ocular implant 300 comprises a body 302. With reference to FIG. 11, it will be appreciated that body 302 comprises a plurality of tissue supporting frames 304 and a plurality of spines 306. As shown in FIG. 11, these spines 306 and frames 304 are arranged in an alternating pattern in which one spine extends between each adjacent pair of frames 304. The frames 304 of body 302 include a first frame 336 of ocular implant 300 is disposed between a first spine 340 and a second spine 342. In the embodiment of FIG. 11, first frame 336 comprises a first strut 344 that extends between first spine 340 and second spine 342. A second strut 346 of first frame also extends between first spine 340 and second spine 342. Each strut undulates in a circumferential direction as it extends longitudinally between first spine 340 and second spine 342.

An inner surface 328 of body 302 defines a channel 326. Body 302 of ocular implant 300 includes a first edge 320 and a second edge 322 that define a first opening 324. Channel 326 of ocular implant 300 fluidly communicates with first opening 324. First strut 344 of first frame 336 comprises a first edge 325A. Second strut 346 has a first edge 325B. In FIG. 11, first opening 324 in body 302 can be seen extending between first edge 325A of first strut 344 and a first edge 325B of second strut 346.

A first axis 356, a second axis 358 and a third axis 360 are shown in FIG. 11. Second axis 358 is generally perpendicular to first axis 356. Third axis 360 is generally skewed relative to first axis 356. The flexibility of body 302 is at a maximum when body 302 is bent by a moment acting about first axis 356, and body 302 has less flexibility when bent by a moment acting about an axis other than first axis 356 (e.g., second axis 358 and third axis 360). Stated another way, in the embodiment of FIG. 11, the bending modulus of body 302 is at a minimum when body 302 is bent by a moment acting about first axis 356, and body 302 has a greater bending modulus when bent by a moment acting about an axis other than first axis 356 (e.g., second axis 358 and third axis 360).

Many of the figures illustrating embodiments of the invention show only portions of the ocular implant. It should be understood that many embodiments of the invention include an inlet portion (such as inlet 101 in FIG. 6 and inlet 201 in FIG. 10) that can be placed within the anterior chamber to provide communication of aqueous humor from the anterior chamber through the trabecular mesh into Schlemm's canal via the ocular implant. Further details of the inlet feature may be found in U.S. application Ser. No. 11/860,318.

Figure 12:
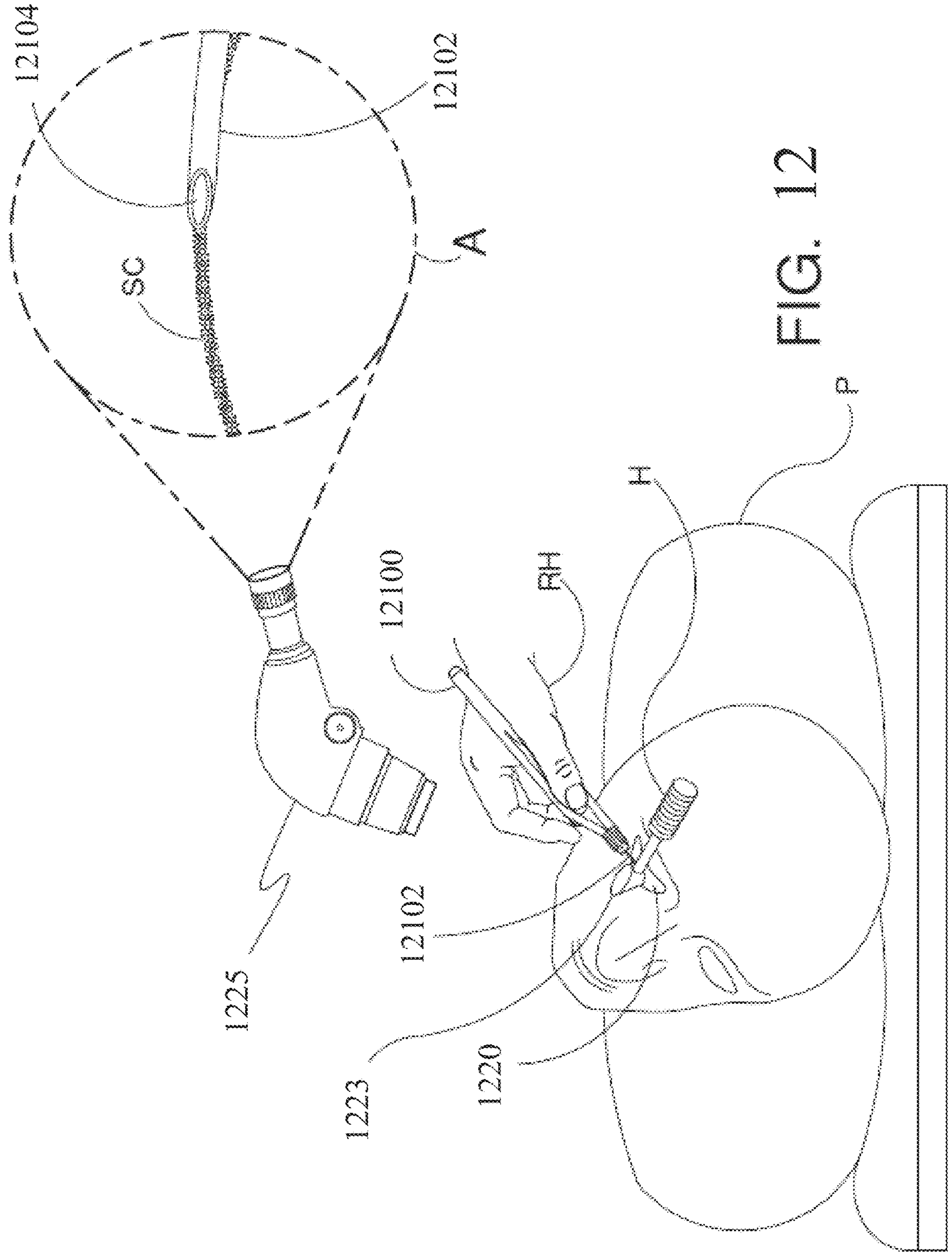
FIG. 12 is a stylized representation of a medical procedure in accordance with this detailed description.

FIG. 12 is a stylized representation of a medical procedure in accordance with this detailed description. In the procedure of FIG. 12, a physician is treating an eye 1220 of a patient P. In the procedure of FIG. 12, the physician is holding a delivery system 12100 in his or her right hand RH. The physician's left hand (not shown) may be used to hold the handle H of a gonio lens 1223. It will be appreciated that some physician's may prefer holding the delivery system handle in the left hand and the gonio lens handle H in the right hand RH.

During the procedure illustrated in FIG. 12, the physician may view the interior of the anterior chamber using gonio lens 1223 and a microscope 1225. Detail A of FIG. 12 is a stylized simulation of the image viewed by the physician. A distal portion of a cannula 12102 is visible in Detail A. A shadow-like line indicates the location of Schlemm's canal SC which is lying under various tissue (e.g., the trabecular meshwork) that surround the anterior chamber. A distal opening 12104 of cannula 12102 is positioned near Schlemm's canal SC of eye 1220. In some methods in accordance with this detailed description, distal opening 12104 of cannula 12102 is placed in fluid communication with Schlemm's canal SC. When this is the case, an ocular implant may be advanced through distal opening 12104 and into Schlemm's canal SC.

Figure 13B:
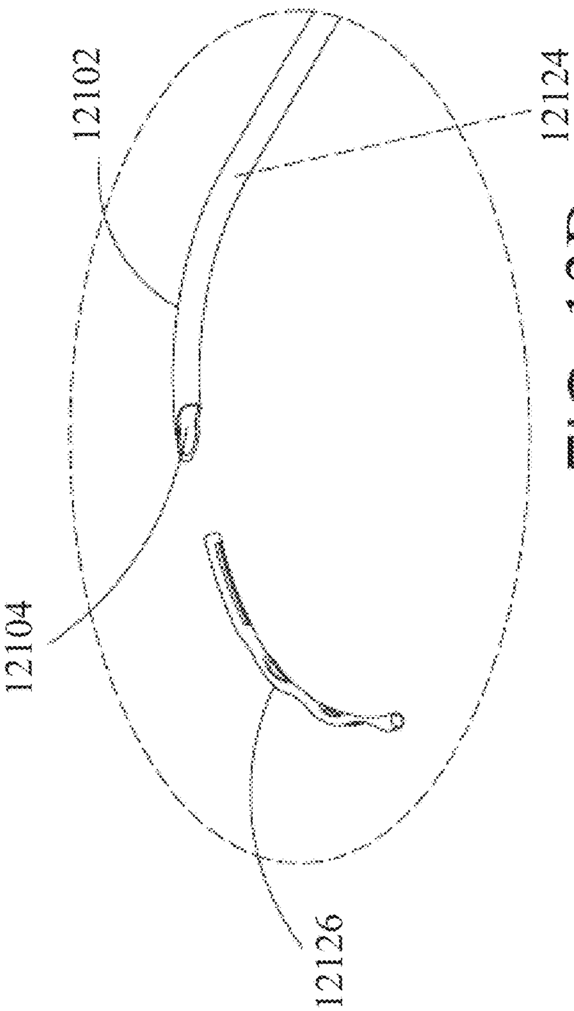
FIG. 13B is an enlarged detail view further illustrating a cannula of the delivery system shown in the previous Figure.
Figure 13A:
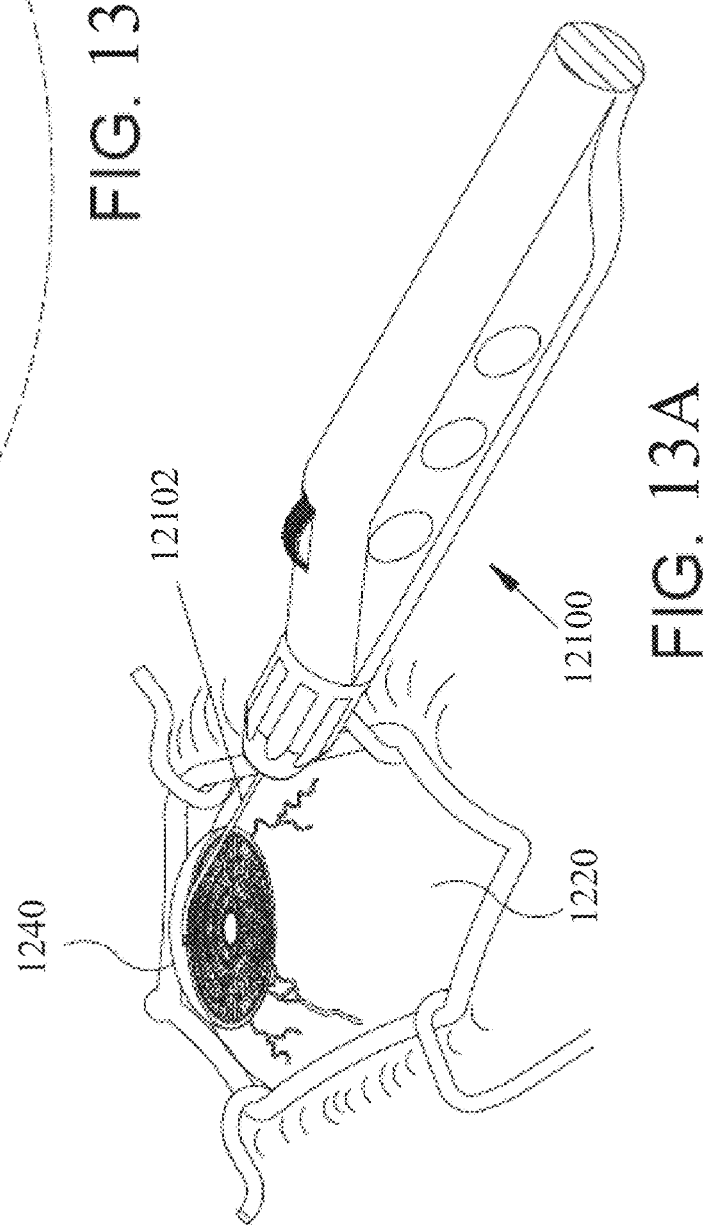
FIG. 13A is a perspective view further illustrating a delivery system 100 used in the medical procedure shown in the previous Figure.

FIG. 13A is a perspective view further illustrating delivery system 12100 and eye 1220 shown in the previous Figure. In FIG. 13A, cannula 12102 of delivery system 12100 is shown extending through a cornea 1240 of eye 1220. A distal portion of cannula 12102 is disposed inside the anterior chamber defined by cornea 1240 of eye 1220. In the embodiment of FIG. 13A, cannula 12102 is configured so that a distal opening 12104 of cannula 12102 can be placed in fluid communication with Schlemm's canal.

In the embodiment of FIG. 13A, an ocular implant is disposed in a lumen defined by cannula 12102. Delivery system 12100 includes a mechanism that is capable of advancing and retracting the ocular implant along the length of cannula 12102. The ocular implant may be placed in Schlemm's canal of eye 1220 by advancing the ocular implant through distal opening 12104 of cannula 12102 while distal opening 12104 is in fluid communication with Schlemm's canal.

FIG. 13B is an enlarged detail view further illustrating cannula 12102 of delivery system 12100. In the illustrative embodiment of FIG. 13B, an ocular implant 12126 has been advanced through distal opening 12104 of cannula 12102. Cannula 12102 of FIG. 13B defines a passageway 12124 that fluidly communicates with distal opening 12104. Ocular implant 12126 may be moved along passageway 12124 and through distal opening by delivery system 12100. Delivery system 12100 includes a mechanism capable of performing this function.

Figure 14:
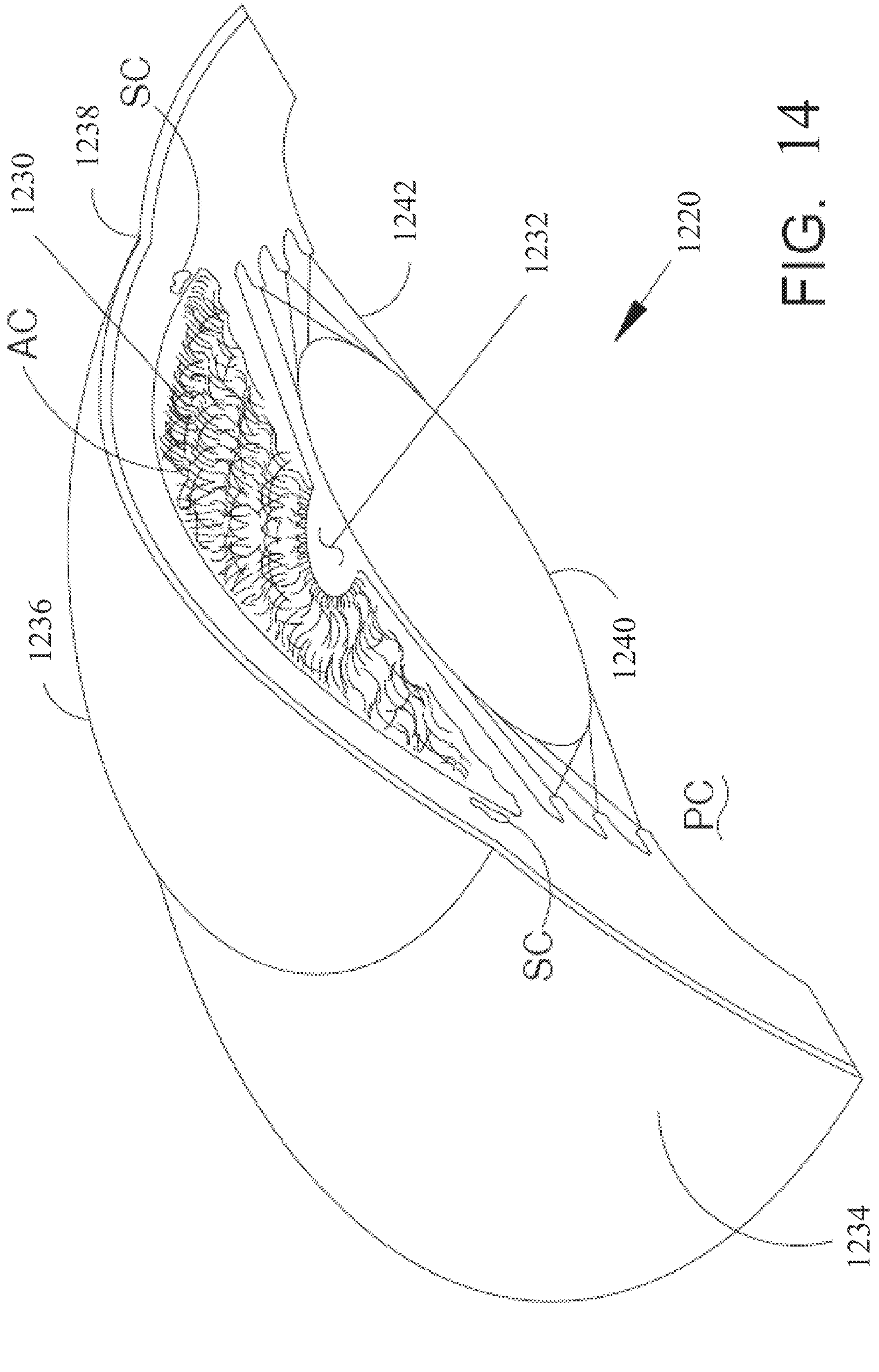
FIG. 14 is a stylized perspective view illustrating the anatomy of an eye.

FIG. 14 is a stylized perspective view illustrating a portion of eye 1220 discussed above. Eye 1220 includes an iris 1230 defining a pupil 1232. In FIG. 14, eye 1220 is shown as a cross-sectional view created by a cutting plane passing through the center of pupil 1232. Eye 1220 can be conceptualized as a fluid filled ball having two chambers. Sclera 1234 of eye 1220 surrounds a posterior chamber PC filled with a viscous fluid known as vitreous humor. Cornea 1236 of eye 1220 encloses an anterior chamber AC that is filled with a fluid known as aqueous humor. The cornea 1236 meets the sclera 1234 at a limbus 1238 of eye 1220. A lens 1240 of eye 1220 is located between anterior chamber AC and posterior chamber PC. Lens 1240 is held in place by a number of ciliary zonules 1242.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

Schlemm's canal SC is a tube-like structure that encircles iris 1230. Two laterally cut ends of Schlemm's canal SC are visible in the cross-sectional view of FIG. 14. In a healthy eye, aqueous humor flows out of anterior chamber AC and into Schlemm's canal SC. Aqueous humor exits Schlemm's canal SC and flows into a number of collector channels. After leaving Schlemm's canal SC, aqueous humor is absorbed into the venous blood stream and carried out of the eye.

Figure 15:
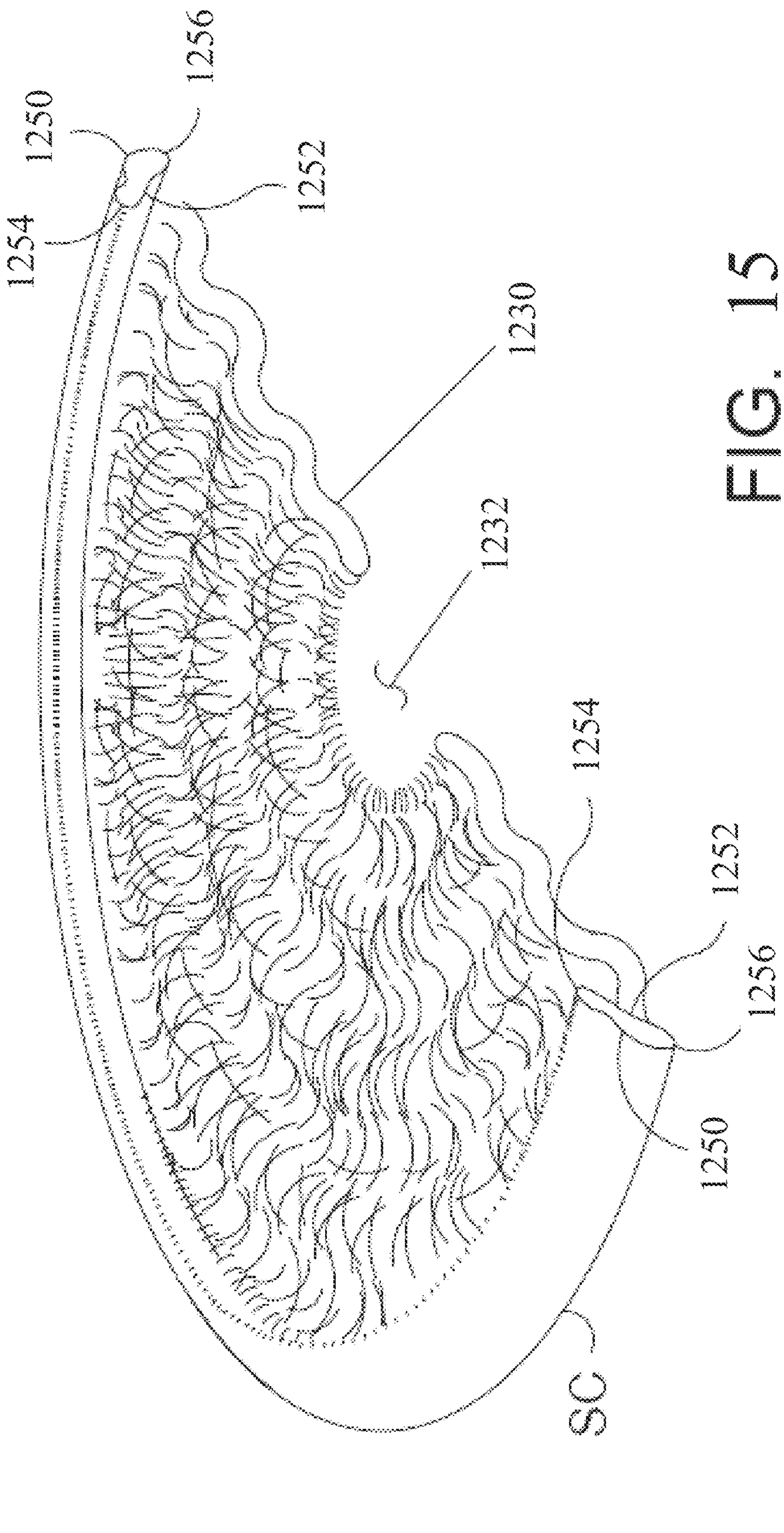
FIG. 15 is a stylized perspective view showing Schlemm's canal and an iris of the eye shown in the previous Figure.

FIG. 15 is a stylized perspective view showing Schlemm's canal SC and iris 1230 of eye 1220 shown in the previous Figure. In FIG. 15, Schlemm's canal SC is shown encircling iris 1230. With reference to FIG. 15, it will be appreciated that Schlemm's canal SC may overhang iris 1230 slightly. Iris 1230 defines a pupil 1232. In the embodiment of FIG. 15, Schlemm's canal SC and iris 1230 are shown in cross-section, with a cutting plane passing through the center of pupil 1232.

The shape of Schlemm's canal SC is somewhat irregular, and can vary from patient to patient. The shape of Schlemm's canal SC may be conceptualized as a cylindrical-tube that has been partially flattened. With reference to FIG. 15, it will be appreciated that Schlemm's canal SC has a first major side 1250, a second major side 1252, a first minor side 1254, and a second minor side 1256.

Schlemm's canal SC forms a ring around iris 1230 with pupil 1232 disposed in the center of that ring. With reference to FIG. 15, it will be appreciated that first major side 1250 is on the outside of the ring formed by Schlemm's canal SC and second major side 1252 is on the inside of the ring formed by Schlemm's canal SC. Accordingly, first major side 1250 may be referred to as an outer major side of Schlemm's canal SC and second major side 1252 may be referred to as an inner major side of Schlemm's canal SC. With reference to FIG. 15, it will be appreciated that first major side 1250 is further from pupil 1232 than second major side 1252.

Figure 16:
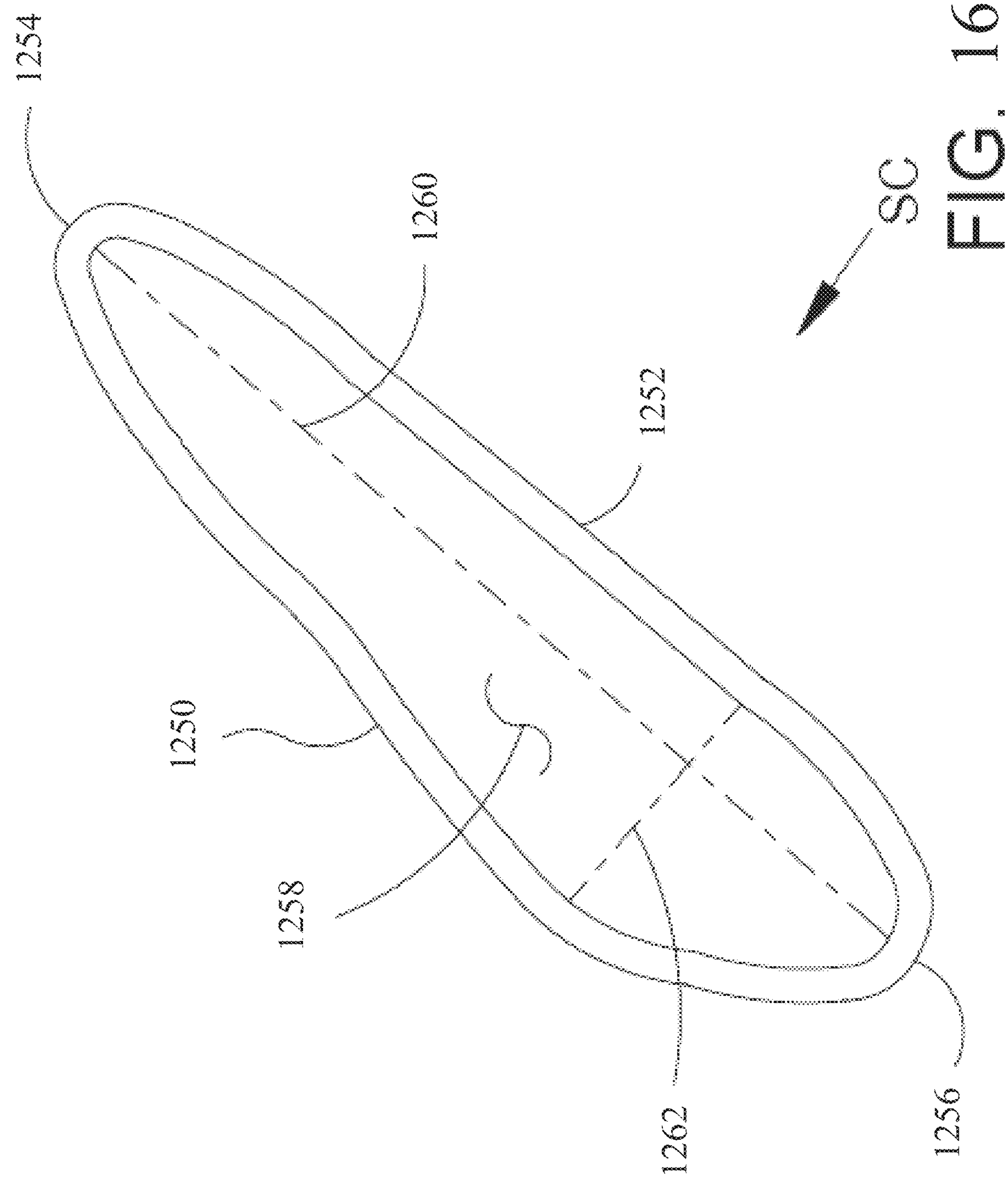
FIG. 16 is an enlarged cross-sectional view further illustrating Schlemm's canal SC shown in the previous Figure.

FIG. 16 is an enlarged cross-sectional view further illustrating Schlemm's canal SC shown in the previous Figure. With reference to FIG. 16, it will be appreciated that Schlemm's canal SC comprises a wall W defining a lumen 1258. The shape of Schlemm's canal SC is somewhat irregular, and can vary from patient to patient. The shape of Schlemm's canal SC may be conceptualized as a cylindrical-tube that has been partially flattened. The cross-sectional shape of lumen 1258 may be compared to the shape of an ellipse. A major axis 1260 and a minor axis 1262 of lumen 1258 are illustrated with dashed lines in FIG. 16.

The length of major axis 1260 and minor axis 1262 can vary from patient to patient. The length of minor axis 1262 is between one and thirty micrometers in most patients. The length of major axis 1260 is between one hundred and fifty micrometers and three hundred and fifty micrometers in most patients.

With reference to FIG. 16, it will be appreciated that Schlemm's canal SC comprises a first major side 1250, a second major side 1252, a first minor side 1254, and a second minor side 1256. In the embodiment of FIG. 16, first major side 1250 is longer than both first minor side 1254 and second minor side 1256. Also in the embodiment of FIG. 16, second major side 1252 is longer than both first minor side 1254 and second minor side 1256.

Figure 17:
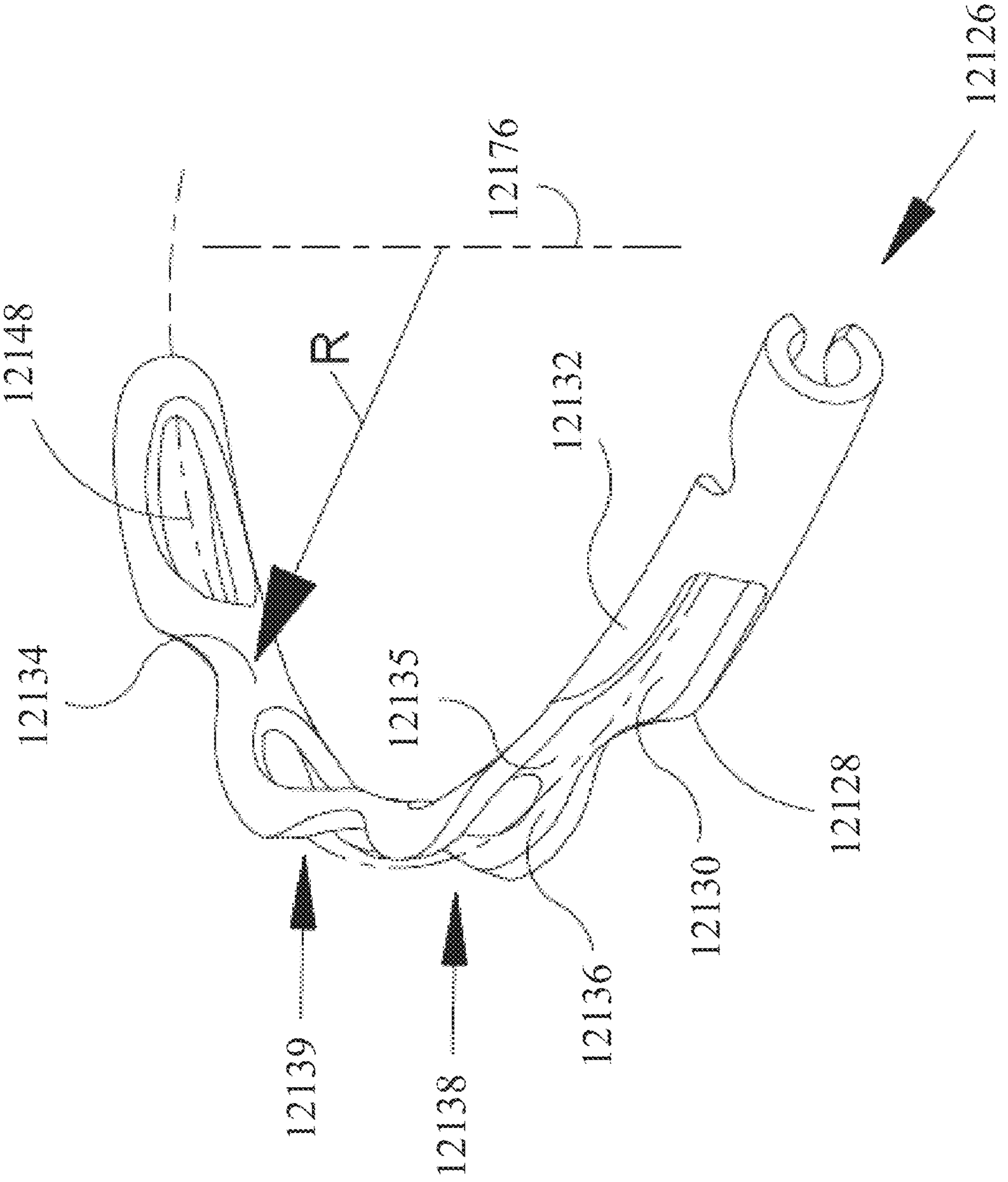
FIG. 17 is a perspective view showing an ocular implant in accordance with this detailed description.

FIG. 17 is a perspective view showing an ocular implant in accordance with this detailed description. Ocular implant 12126 of FIG. 17 comprises a body 12128 that extends along a generally curved longitudinal central axis 12148. In the embodiment of FIG. 17, body 12128 has a radius of curvature R that is represented with an arrow extending between a lateral central axis 12176 and body 12128.

Body 12128 of ocular implant 12126 has a first major surface 12130 and a second major surface 12132. With reference to FIG. 17, it will be appreciated that body 12128 is curved about longitudinal central axis 12148 so that first major surface 12130 comprises a concave surface 12136 and second major surface 12132 comprises a convex surface 12134. The curvature of body 12128 can be pre-sized and configured to align with the curvature of Schlemm's canal in a patient's eye.

A distal portion of body 12128 defines a longitudinal channel 12138 including a channel opening 12139. Channel opening 12139 is disposed diametrically opposite a central portion 12135 of concave surface 12136. Because of the curvature of the body 12128, an outer diameter of the implant defined by the channel opening 12139 will be greater than an inner diameter of the implant defined by surface 12132. In some embodiments, the body is pre-biased to assume a configuration in which the channel opening 12139 is disposed along an outer diameter of the body, ensuring that the channel opening can be positioned adjacent to the first major side 1250 of Schlemm's canal.

In the embodiment of FIG. 17, central portion 12135 of concave surface 12136 defines a plurality of apertures 12137. Each aperture 12137 fluidly communicates with channel 12138. In some useful embodiments, body 12128 is adapted and configured such that ocular implant 12126 assumes an orientation in which channel opening 12139 is adjacent a major side of Schlemm's canal when ocular implant 12126 is disposed in Schlemm's canal. Ocular implant 12126 can be made, for example, by laser cutting body 12128 from a length of metal or a shape memory material (e.g., nitinol or stainless steel) tubing.

Figure 18A:
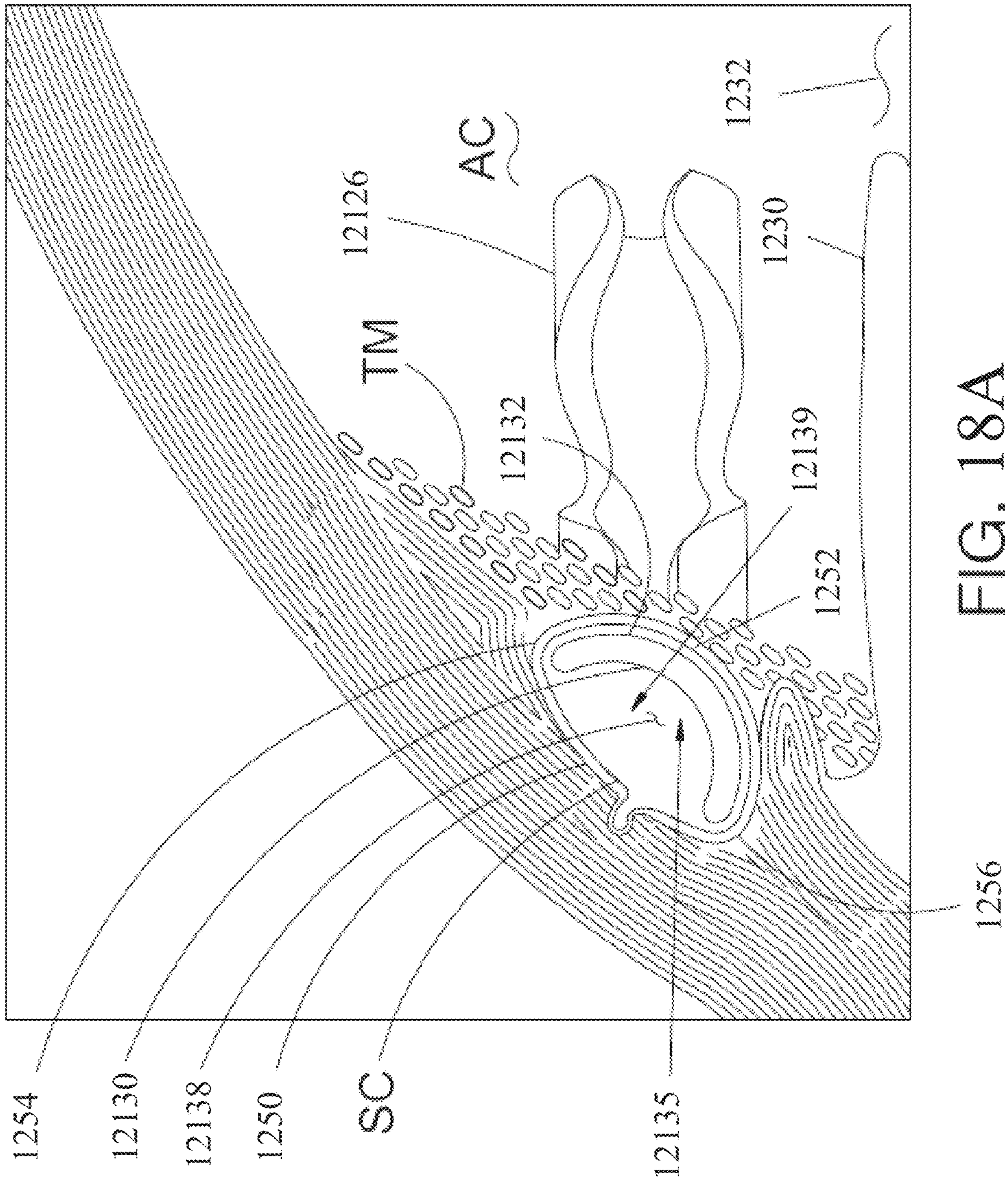
FIG. 18A and FIG. 18B are section views showing an ocular implant disposed in Schlemm's canal of an eye.
Figure 18B:
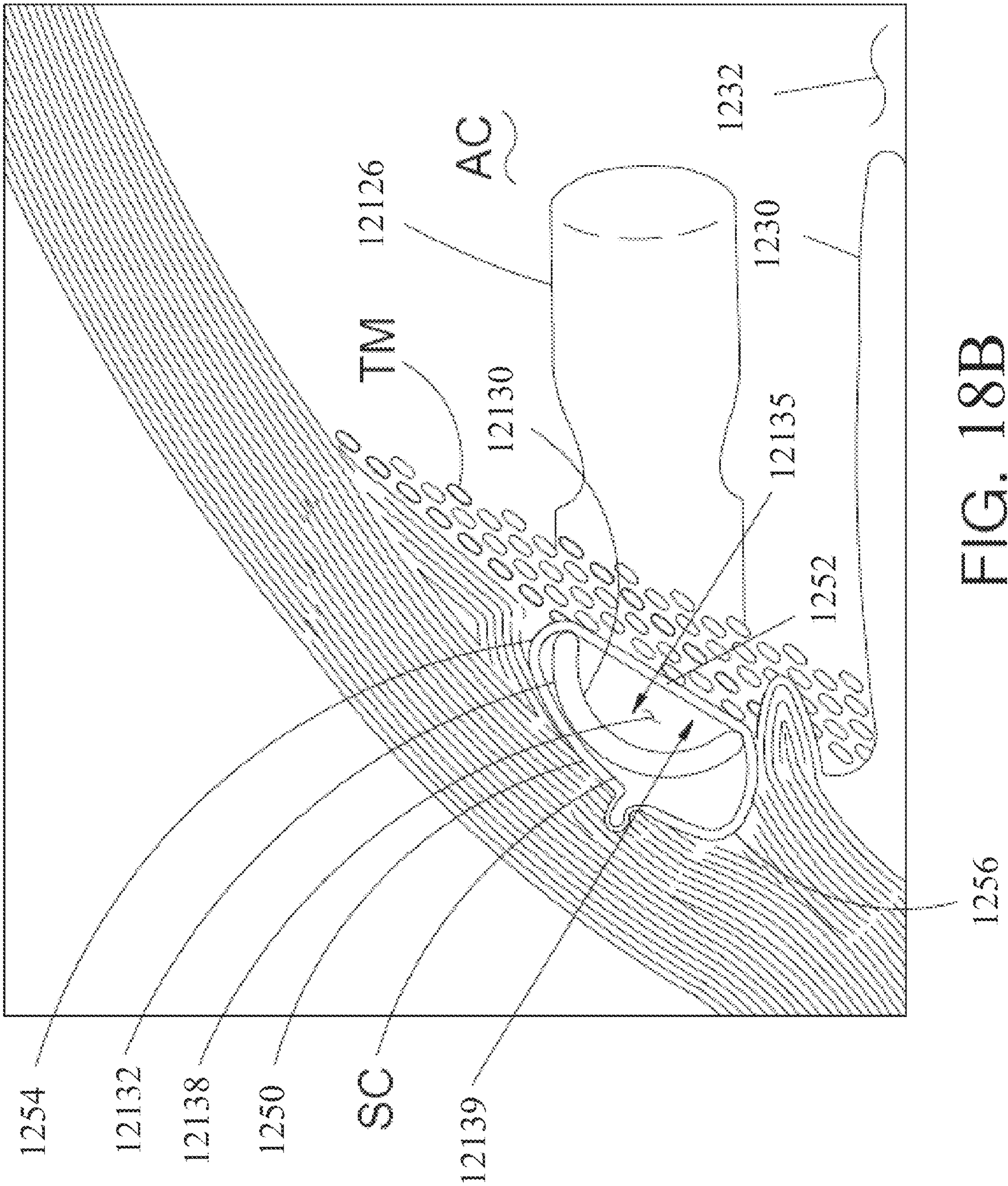

FIG. 18A and FIG. 18B are section views showing an ocular implant 12126 disposed in Schlemm's canal SC of an eye. FIG. 18A and FIG. 18B may be collectively referred to as FIG. 18. The eye of FIG. 18 includes an iris 1230. A central portion of iris 1230 defines a pupil 1232. Schlemm's canal SC is disposed near an outer edge of iris 1230. The trabecular meshwork TM extends up from the iris of overlays Schlemm's canal SC. The picture plane of FIG. 18 extends laterally across Schlemm's canal SC and the trabecular meshwork TM.

Schlemm's canal SC forms a ring around iris 1230 with pupil 1232 disposed in the center of that ring. Schlemm's canal SC has a first major side 1250, a second major side 1252, a first minor side 1254, and a second minor side 1256.

With reference to FIG. 18, it will be appreciated that first major side 1250 is further from pupil 1232 than second major side 1252. In the embodiment of FIG. 18, first major side 1250 is an outer major side of Schlemm's canal SC and second major side 1252 is an inner major side of Schlemm's canal SC.

In the embodiment of FIG. 18A, a distal portion of ocular implant 12126 is shown resting in Schlemm's canal SC. A proximal portion of ocular implant 12126 is shown extending out of Schlemm's canal SC, through trebecular meshwork TM and into anterior chamber AC. Ocular implant 12126 of FIG. 18 comprises a body having a first major surface 12130 and a second major surface 12132. With reference to FIG. 17, it will be appreciated that the body of ocular implant 126 is curved about a longitudinal central axis so that first major surface 12130 comprises a concave surface and second major surface 12132 comprises a convex surface.

A distal portion of ocular implant 12126 defines a longitudinal channel 12138 including a channel opening 12139. Channel opening 12139 is disposed diametrically opposite a central portion 12135 of first major surface 12130. In the embodiment of FIG. 18A, ocular implant 12126 is assuming an orientation in which channel opening 12139 is adjacent and open to first major side 50 of Schlemm's canal. In the embodiment of FIG. 18B, ocular implant 12126 is assuming an orientation in which channel opening 12139 is adjacent and open to second major side 1252 of Schlemm's canal.

Figures 19A, 19B, 19C:
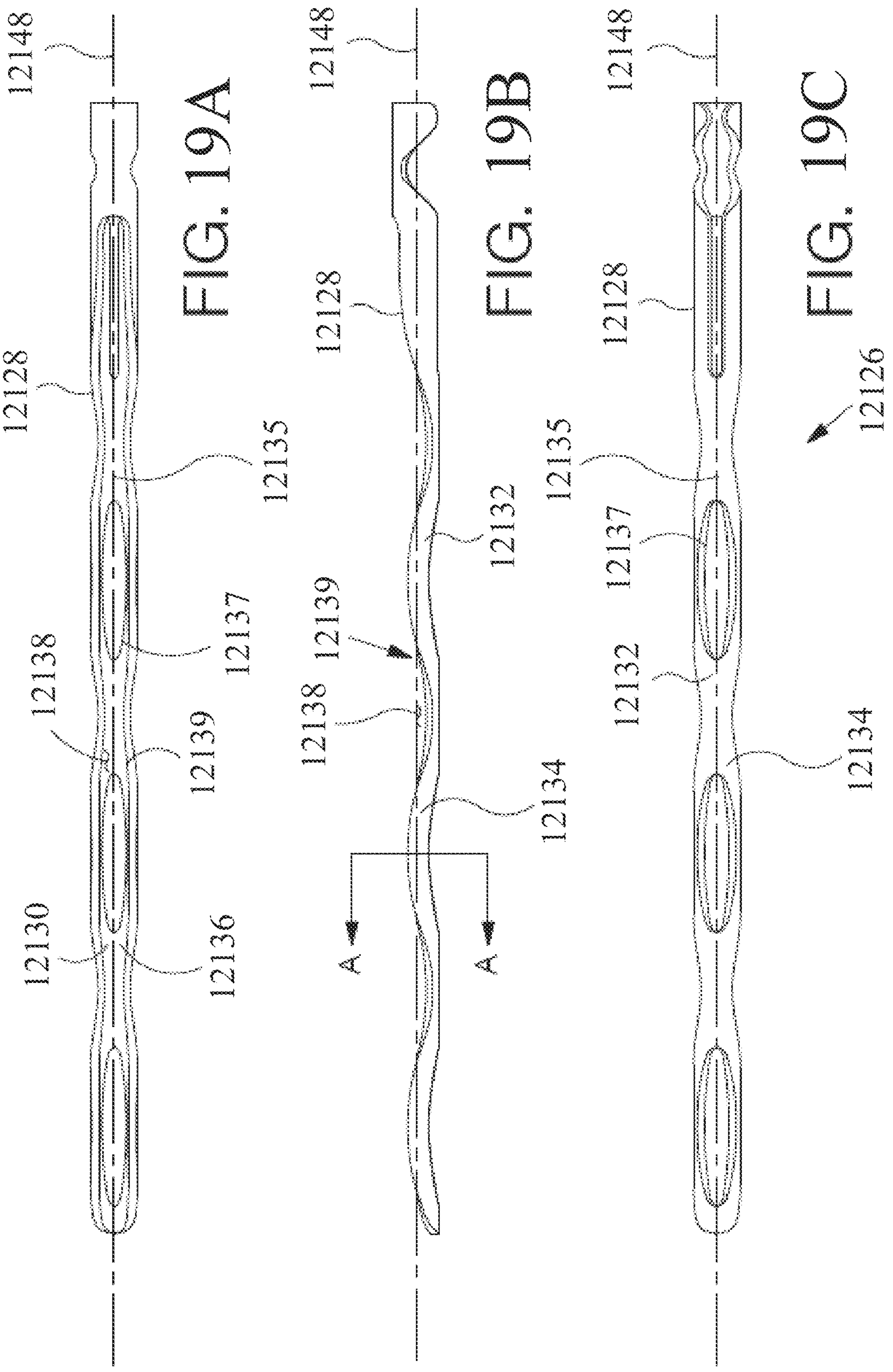
FIG. 19A, FIG. 19B and FIG. 19C are multiple plan views illustrating an implant in accordance with the present detailed description.

FIG. 19A, FIG. 19B and FIG. 19C illustrate multiple plan views of an implant 12126 in accordance with the present detailed description. FIG. 19A, FIG. 19B and FIG. 19C may be referred to collectively as FIG. 19. It is customary to refer to multi-view projections using terms such as front view, top view, and side view. In accordance with this convention, FIG. 19A may be referred to as a top view of implant 12126, FIG. 19B may be referred to as a side view of implant 12126, and FIG. 19C may be referred to as a bottom view of implant 12126. The terms top view, side view, and bottom view are used herein as a convenient method for differentiating between the views shown in FIG. 19. It will be appreciated that the implant shown in FIG. 8 may assume various orientations without deviating from the spirit and scope of this detailed description. Accordingly, the terms top view, side view, and bottom view should not be interpreted to limit the scope of the invention recited in the attached claims.

Ocular implant 12126 of FIG. 19 comprises a body 12128 that extends along a longitudinal central axis 12148. Body 12128 of ocular implant 12126 has a first major surface 12130 and a second major surface 12132. In the embodiment of FIG. 19, body 12128 is curved about longitudinal central axis 12148 so that first major surface 12130 comprises a concave surface 12136 and second major surface 12132 comprises a convex surface 12134.

A distal portion of body 12128 defines a longitudinal channel 12138 including a channel opening 12139. Channel opening 12139 is disposed diametrically opposite a central portion 12135 of concave surface 12136. In the embodiment of FIG. 19, central portion 12135 of concave surface 12136 defines a plurality of apertures 12137. Each aperture 12137 fluidly communicates with channel 12138. In some useful embodiments, body 12128 is adapted and configured such that ocular implant 12126 assumes an orientation in which channel opening 12139 is adjacent a major side of Schlemm's canal when ocular implant 12126 is disposed in Schlemm's canal.

Figure 20:
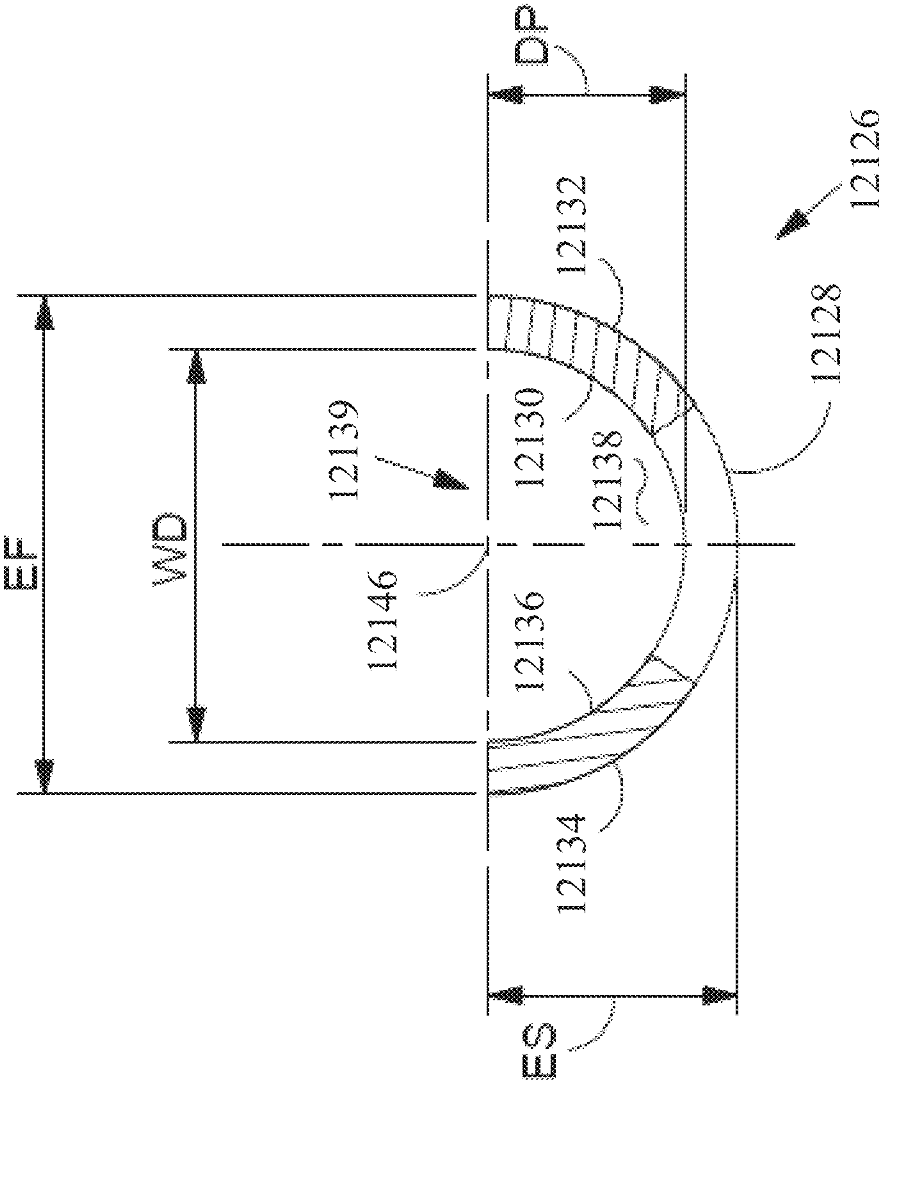
FIG. 20 is a lateral cross-sectional view of an ocular implant taken along section line A-A shown in the previous Figure.

FIG. 20 is a lateral cross-sectional view of ocular implant 12126 taken along section line A-A shown in the previous Figure. Ocular implant 12126 comprises a body 12128 having a first major surface 12130 and a second major surface 12132. With reference to FIG. 20, it will be appreciated that body 12128 curves around a longitudinal central axis 12148 so that first major surface 12130 comprises a concave surface 12136 and second major surface 12132 comprises a convex surface 12134. The concave surface 12136 of body 12128 defines a longitudinal channel 12138 having a channel opening 12139.

As shown in FIG. 20, channel 12138 has a width WD and a depth DP. Body 12128 of ocular implant 12126 has a first lateral extent EF and a second lateral extent ES. In some cases, body 12128 is adapted and configured such that ocular implant 12126 automatically assumes an orientation in which the channel opening is adjacent a major side of Schlemm's canal when ocular implant 12126 is disposed in Schlemm's canal. In some useful embodiments, an aspect ratio of first lateral extent EF to second lateral extent ES is greater than about one. In some particularly useful embodiments, the aspect ratio of first lateral extent EF to second lateral extent ES is about two. In some useful embodiments, the aspect ratio of first lateral extent EF to second lateral extent ES is greater than about two. In some useful embodiments, an aspect ratio of channel width WD to channel depth DP is greater than about one. In some particularly useful embodiments, the aspect ratio of channel width WD to channel depth DP is about two. In some useful embodiments, the aspect ratio of channel width WD to channel depth DP is greater than about two.

Figure 21A:
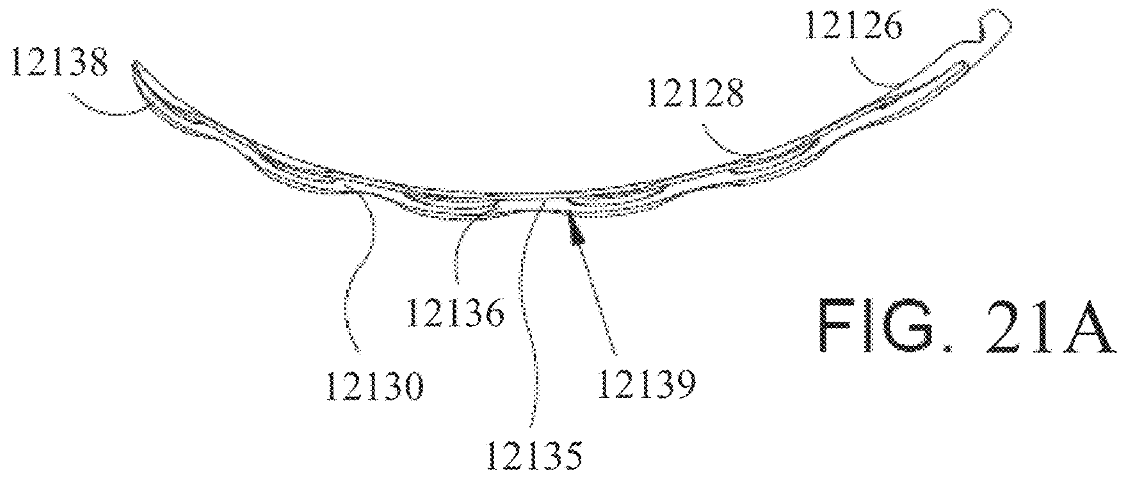
FIG. 21A is a perspective view of an ocular implant and FIG. 21B is a stylized perspective view showing Schlemm's canal SC encircling an iris.
Figure 21B:
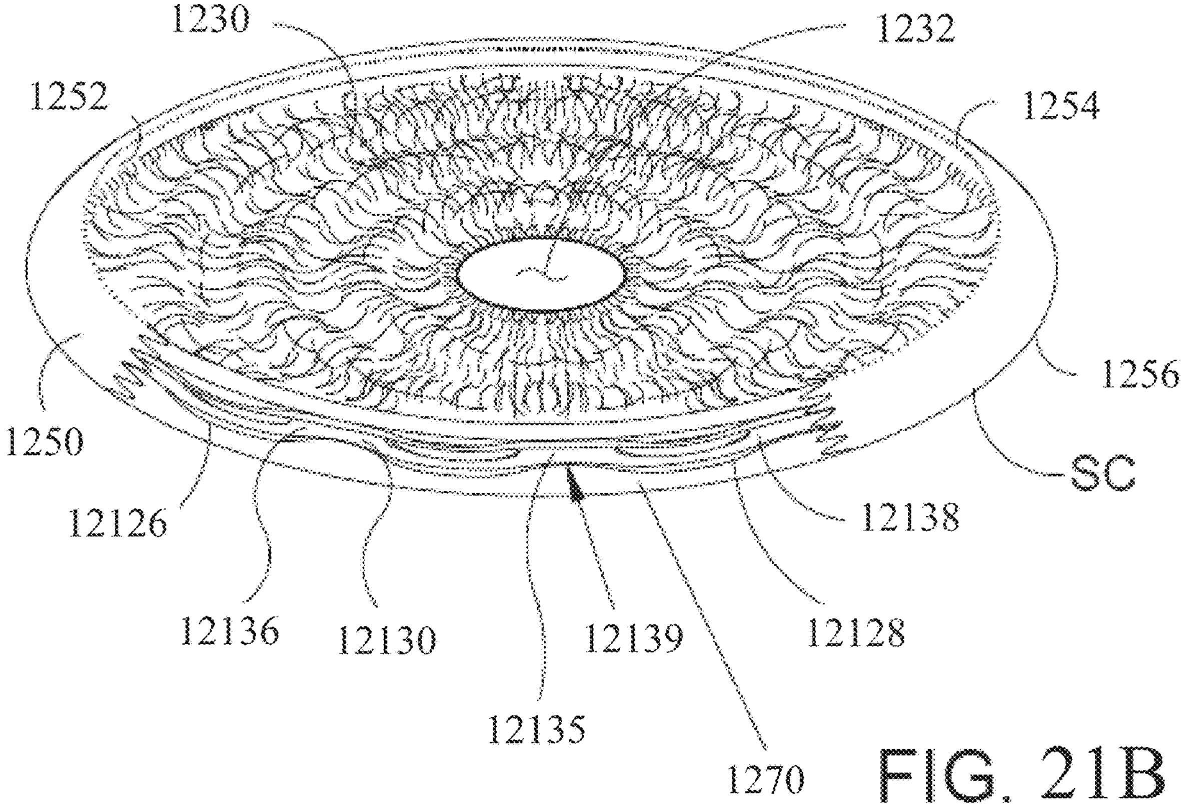

FIG. 21A is a perspective view of an ocular implant 12126 and FIG. 21B is a stylized perspective view showing Schlemm's canal SC encircling an iris 1230. FIG. 21A and FIG. 21B may be collectively referred to as FIG. 21. With reference to FIG. 21B, it will be appreciated that Schlemm's canal SC may overhang iris 1230 slightly. Iris 1230 defines a pupil 1232. Schlemm's canal SC forms a ring around iris 1230 with pupil 1232 disposed in the center of that ring. With reference to FIG. 21B, it will be appreciated that Schlemm's canal SC has a first major side 1250, a second major side 1252, a first minor side 1254, and a second minor side 1256. With reference to FIG. 21B, it will be appreciated that first major side 1250 is further from pupil 1232 than second major side 1252. In the embodiment of FIG. 21B, first major side 1250 is an outer major side of Schlemm's canal SC and second major side 1252 is an inner major side of Schlemm's canal SC.

For purposes of illustration, a window 1270 is cut through first major side 1250 of Schlemm's canal SC in FIG. 21B. Through window 1270, an ocular implant 12126 can be seen residing in a lumen defined by Schlemm's canal. Ocular implant 12126 of FIG. 21 comprises a body 12128 having a first major surface 12130. First major surface 12130 of body 12128 comprises a concave surface 12136. Body 12128 defines a longitudinal channel 12138 including a channel opening 12139. Channel opening 12139 is disposed diametrically opposite a central portion 12135 of concave surface 12136. In the embodiment of FIG. 21B, ocular implant 12126 is assuming an orientation in which channel opening 12139 is adjacent first major side 1250 of Schlemm's canal.

Figure 22B:
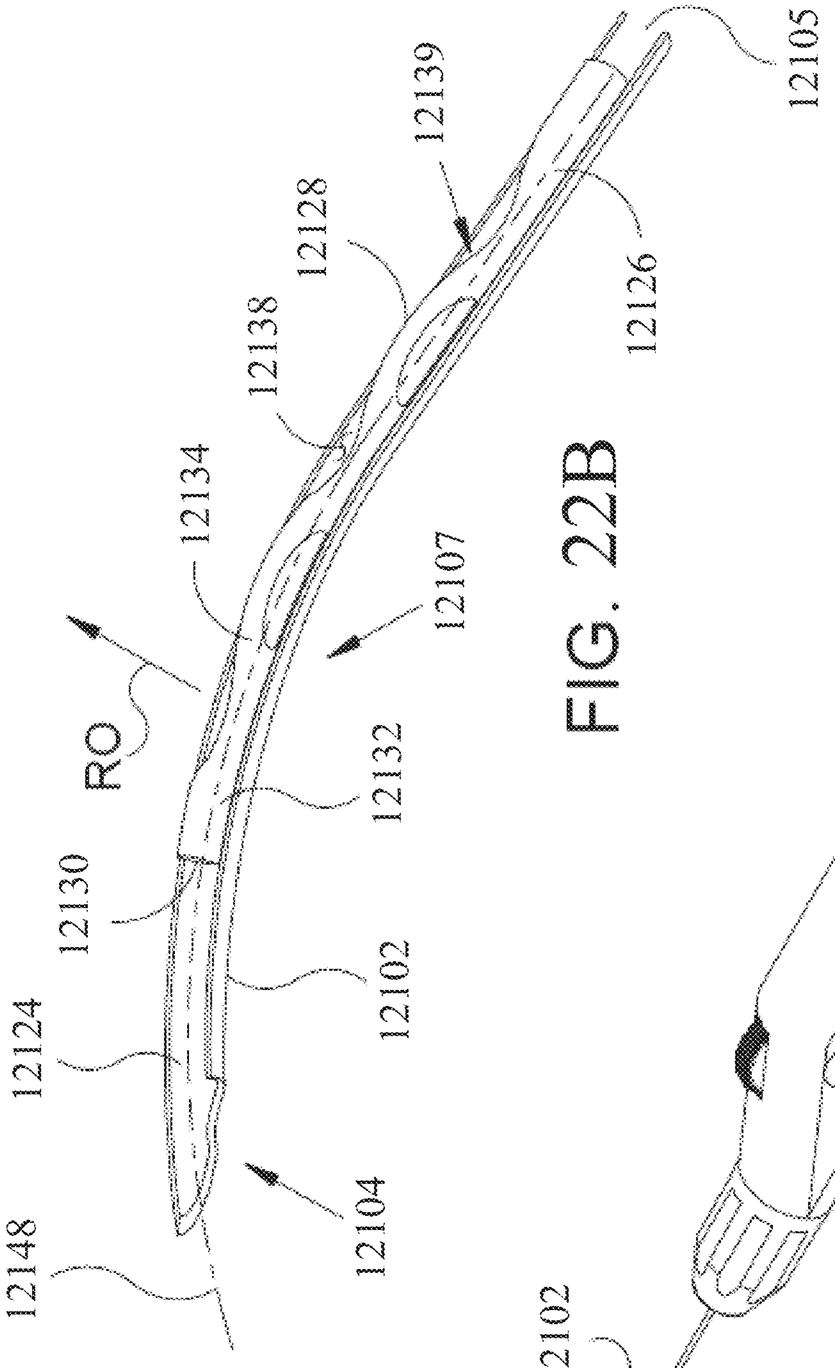
FIG. 22B is an enlarged detail view illustrating a cannula portion of the delivery system.
Figure 22A:
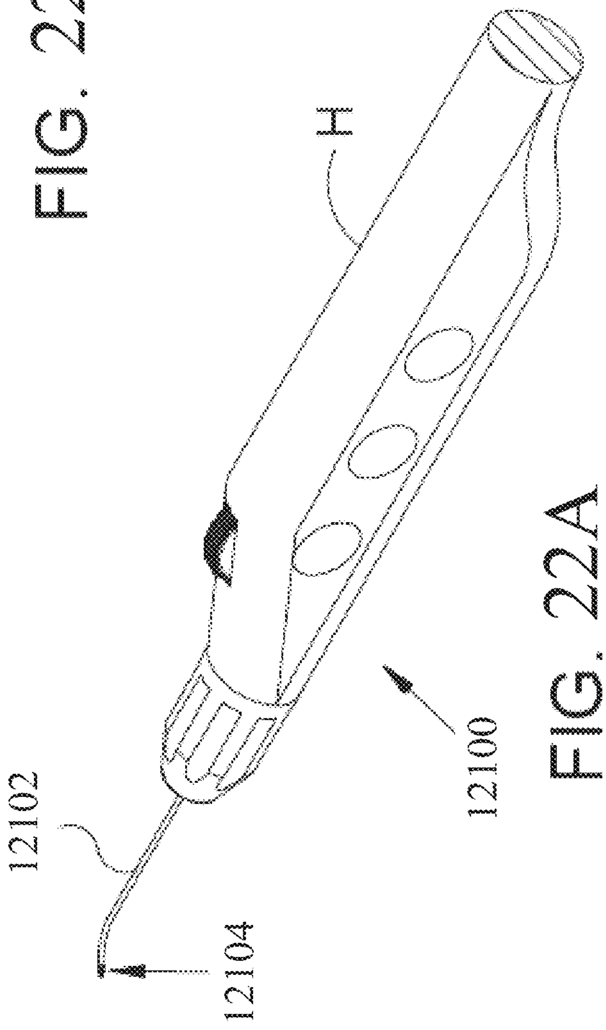
FIG. 22A is a perspective view showing a delivery system 12100 that may be used to advance an ocular implant into Schlemm's canal of an eye.

FIG. 22A is a perspective view showing a delivery system 12100 that may be used to advance an ocular implant 12126 into Schlemm's canal of an eye. Delivery system 12100 includes a cannula 12102 that is coupled to a handle H. Cannula 12102 defines a distal opening 21104. The distal portion of cannula 21102 of delivery system 12100 is configured and adapted to be inserted into the anterior chamber of a human subject's eye so that distal opening 12104 is positioned near Schlemm's canal of the eye. Cannula 12102 is sized and configured so that the distal end of cannula 21102 can be advanced through the trabecular meshwork of the eye and into Schlemm's canal. Positioning cannula 12102 in this way places distal opening 12104 in fluid communication with Schlemm's canal.

In the embodiment of FIG. 22A, an ocular implant is disposed in a passageway defined by cannula 12102. Delivery system 12100 includes a mechanism that is capable of advancing and retracting the ocular implant along the length of cannula 12102. The ocular implant may be placed in Schlemm's canal of eye 1220 by advancing the ocular implant through distal opening 12104 of cannula 12102 while distal opening 12104 is in fluid communication with Schlemm's canal.

FIG. 22B is an enlarged detail view further illustrating cannula 12102 of delivery system 12100. With reference to FIG. 22B, it will be appreciated that cannula 12102 comprises a tubular member defining a distal opening 12104, a proximal opening 12105, and a passageway 12124 extending between proximal opening 12105 and distal opening 12104. With reference to FIG. 22B, it will be appreciated that cannula 12102 includes a curved portion 12107 disposed between distal opening 12104 and proximal opening 12105.

In the embodiment of FIG. 22B, an ocular implant 12126 is disposed in passageway 12124 defined by cannula 12102. Ocular implant 12126 of FIG. 22B comprises a body 12128 that extends along a generally curved longitudinal central axis 12148. Body 12128 of ocular implant 12126 has a first major surface 12130 and a second major surface 12132. With reference to FIG. 22B, it will be appreciated that body 12128 is curved about longitudinal central axis 12148 so that first major surface 12130 defines a longitudinal channel 12138 and second major surface 12132 comprises a convex surface 12134. Longitudinal channel 12138 includes a channel opening 12139. Ocular implant 12126 is orient relative to delivery cannula 12102 such that longitudinal channel 12138 of ocular implant 12126 opens in a radially outward direction RD when ocular implant 12126 is disposed in curved portion 12107. Radially outward direction RD is illustrated using an arrow in FIG. 22B. Distal opening 12104 of cannula 12102 may be placed in fluid communication with Schlemm's canal of an eye. Implant 12126 may be advanced through distal opening 12104 and into Schlemm's canal while assuming the orientation shown in FIG. 22B. When this is the case, ocular implant 12126 may be oriented such that channel opening 12139 is adjacent an outer major side of Schlemm's canal when ocular implant 12126 is disposed in Schlemm's canal.

Figure 23:
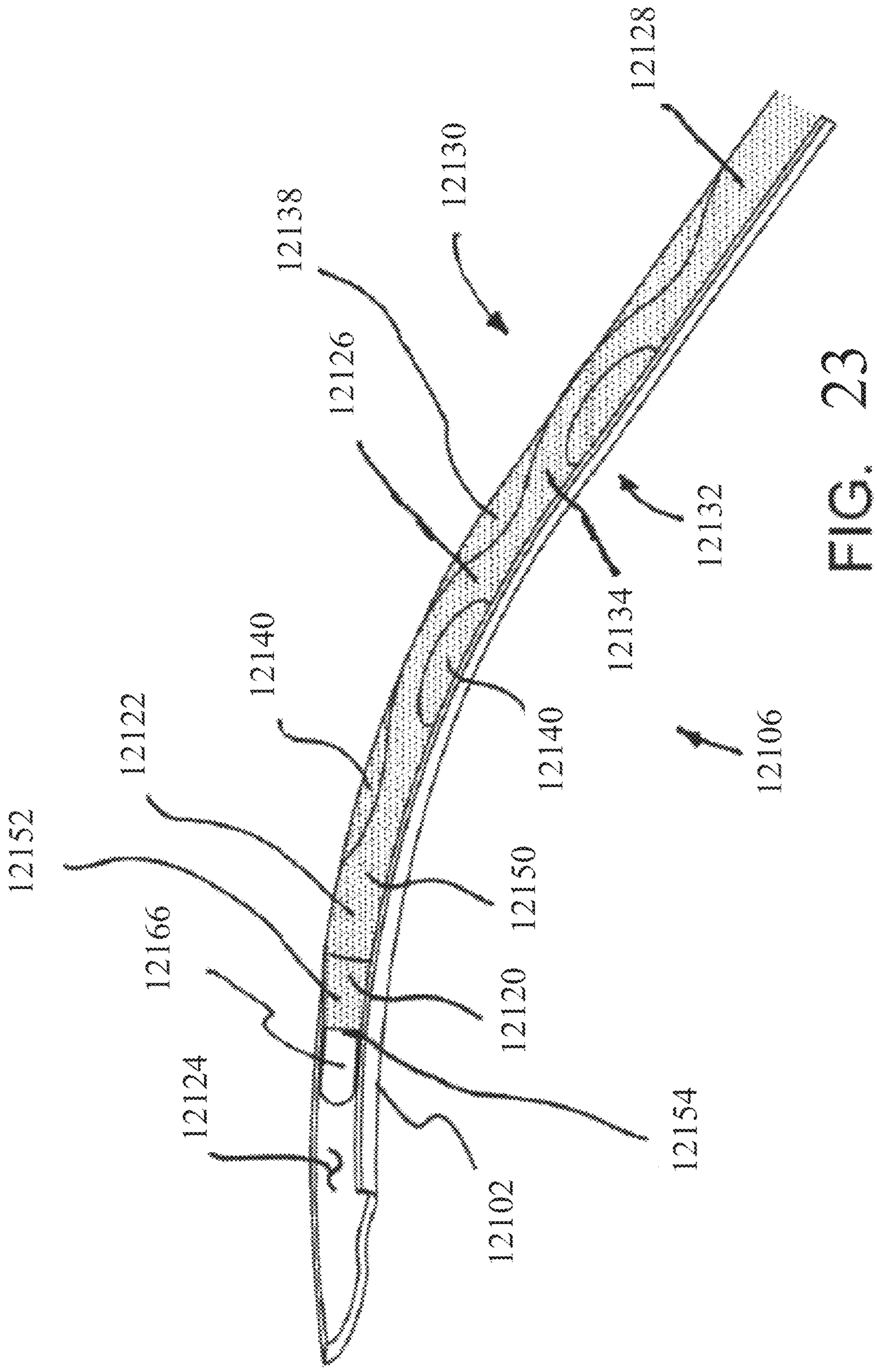
FIG. 23 is an enlarged perspective view of an assembly including a cannula, an ocular implant, and a sheath.

FIG. 23 is an enlarged perspective view of an assembly 12106 including an ocular implant 12126, a sheath 12120, and a cannula 12102. For purposes of illustration, cannula 12102 is cross-sectionally illustrated in FIG. 23. In the embodiment of FIG. 23, a sheath 12120 is shown extending into a passageway 12124 defined by cannula 12102. In FIG. 23, sheath 12120 is illustrated in a transparent manner with a pattern of dots indicating the presence of sheath 12120.

With reference to FIG. 23, it will be appreciated that an implant 12126 is disposed in a lumen 12122 defined by sheath 12120. Implant 12126 comprises a body 12128 having a first major surface 12130 and a second major surface 12132. In the embodiment of FIG. 23, body 12128 curves around a longitudinal central axis so that first major surface 12130 comprises a concave surface and second major surface 12132 comprises a convex surface 12134. The concave surface of body 12128 defines a longitudinal channel 12138. In FIG. 23, a core 12166 is shown extending through longitudinal channel 12138.

Body 12128 of ocular implant 12126 defines a plurality of openings 12140. In the embodiment of FIG. 23, sheath 12120 is covering openings 12140. With reference to FIG. 23, it will be appreciated that sheath 12120 comprises a proximal portion 12150 defining a lumen 12122 and a distal portion 12152 defining a distal aperture 12154. Core 12166 is shown extending through distal aperture 12154 in FIG. 23. In the embodiment of FIG. 23, distal portion 12152 of sheath 12120 has a generally tapered shape.

Figure 24:
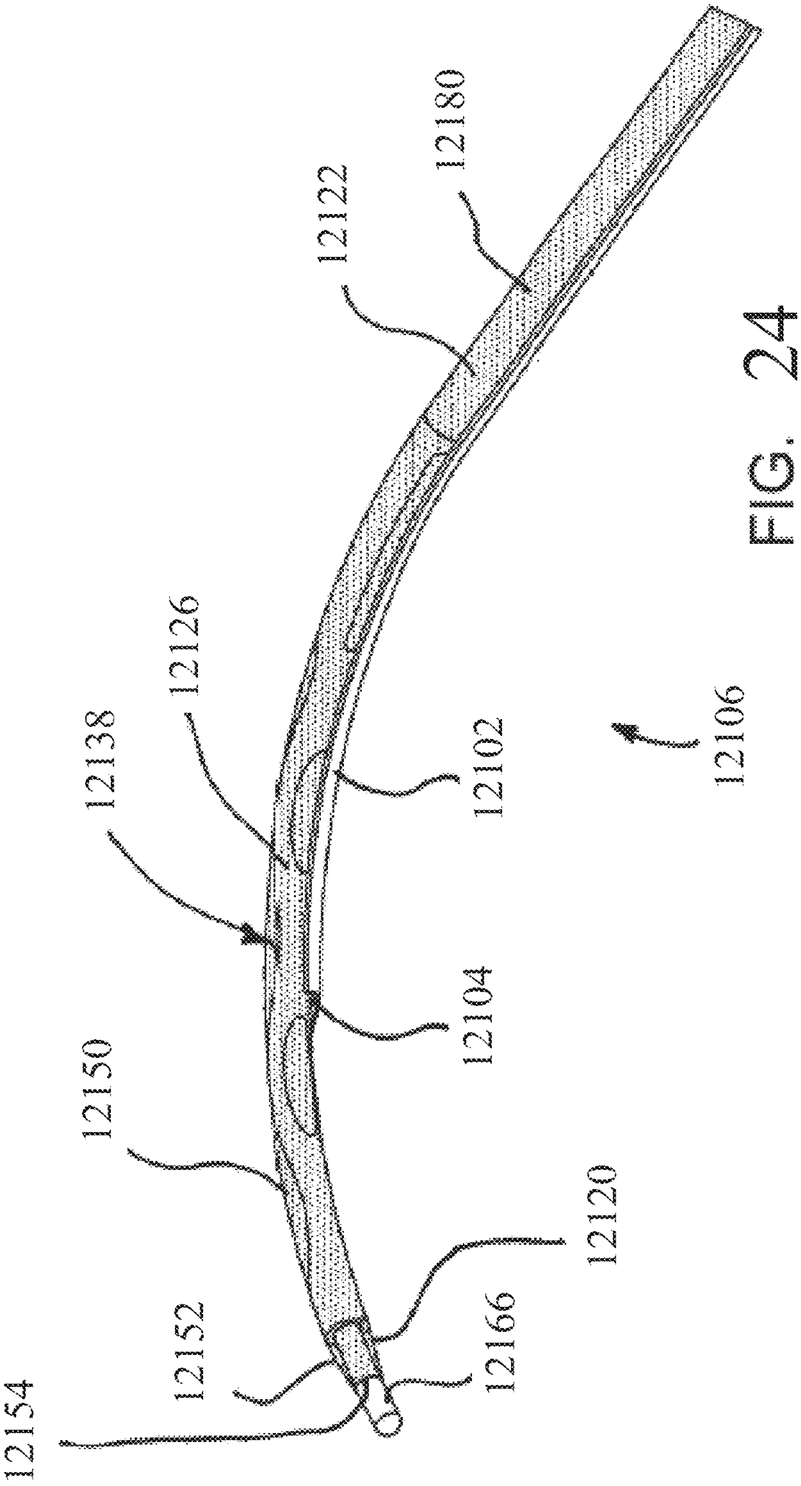
FIG. 24 is an additional perspective view of the assembly shown in the previous Figure.

FIG. 24 is an additional perspective view of assembly 12106 shown in the previous Figure. In FIG. 24, core 12166, sheath 12120, and implant 12126 are shown extending through a distal port 12104 of cannula 12102. Core 12166, sheath 12120, and implant 12126 have been moved in a distal direction relative to the position of those elements shown in the previous Figure.

A push tube 12180 is visible in FIG. 24. In FIG. 24, a distal end of push tube 12180 is shown contacting a proximal end of implant 12126. In the embodiment of FIG. 24, push tube 12180 is disposed in a lumen 12122 defined by sheath 12120. Sheath 12120 comprises a proximal portion 12150 defining a passageway 12124 and a distal portion 12152 defining a distal aperture 12154. Implant 12126 is disposed in lumen 12122 defined by sheath 12120. In FIG. 24, core 12166 is shown extending through a channel 12138 defined by implant 12126 and a distal aperture 12154 defined by distal portion 12152 of sheath 12120.

Figure 25:
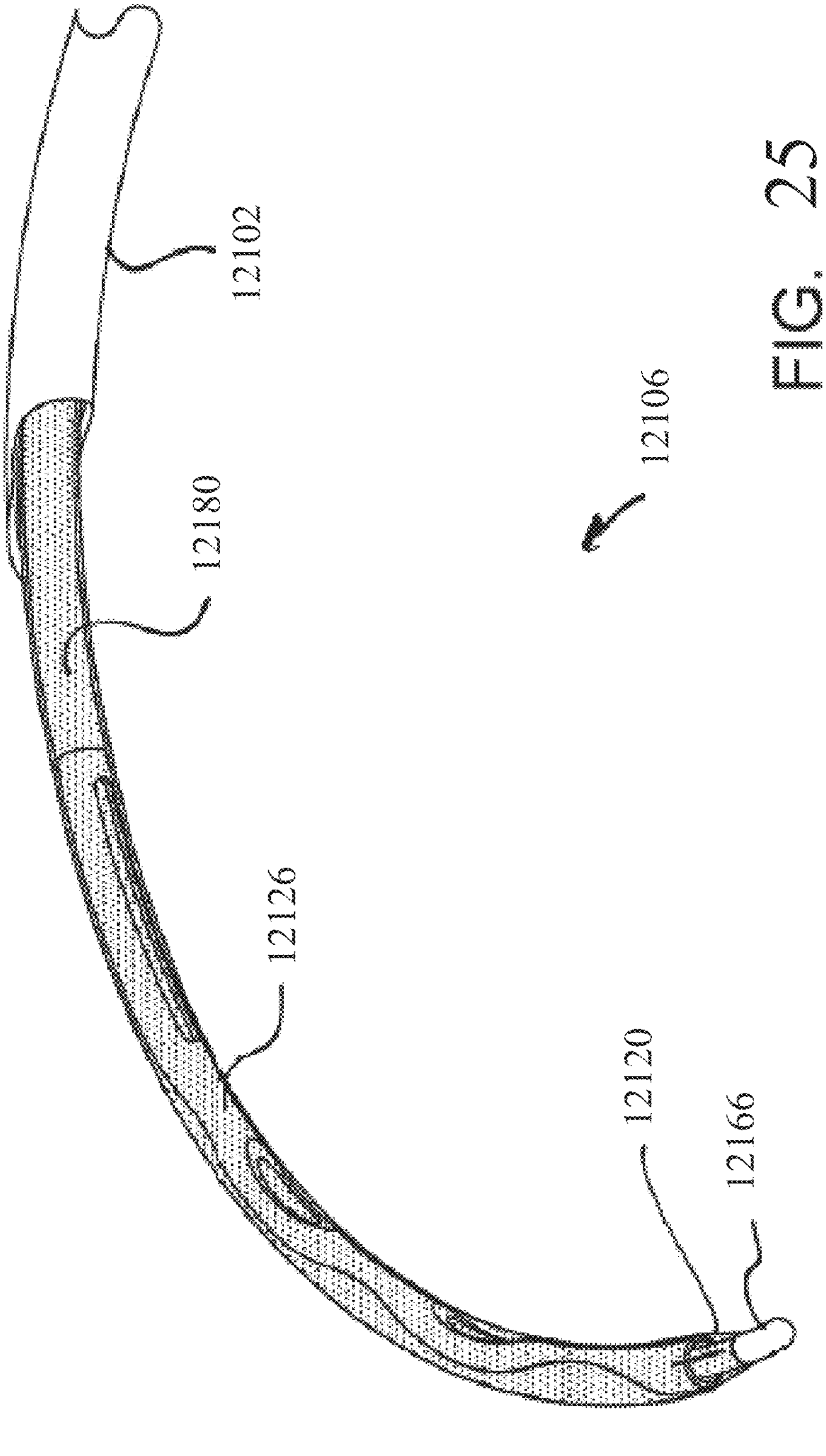
FIG. 25 is another perspective view of an assembly including a cannula, an ocular implant, and a sheath.

FIG. 25 is an additional perspective view showing assembly 12106 shown in the previous Figure. With reference to FIG. 25, it will be appreciated that implant 12126 is disposed outside of cannula 12102. In the embodiment of FIG. 25, core 12166, sheath 12120, and push tube 12180 have been advanced further so that implant 12126 is in a position outside of cannula 12102.

Methods in accordance with the present invention can be used to deliver an implant into Schlemm's canal of an eye. In these methods, a distal portion of core 12166 and sheath 12120 may be advanced out of the distal port of cannula 12102 and into Schlemm's canal. Ocular implant 12126 may be disposed inside sheath 12120 while the distal portion of the sheath 12120 is advanced into Schlemm's canal. Sheath 12120 and core 12166 may then be retracted while push tube 12180 prevents implant 12126 from being pulled proximally.

Figure 26:
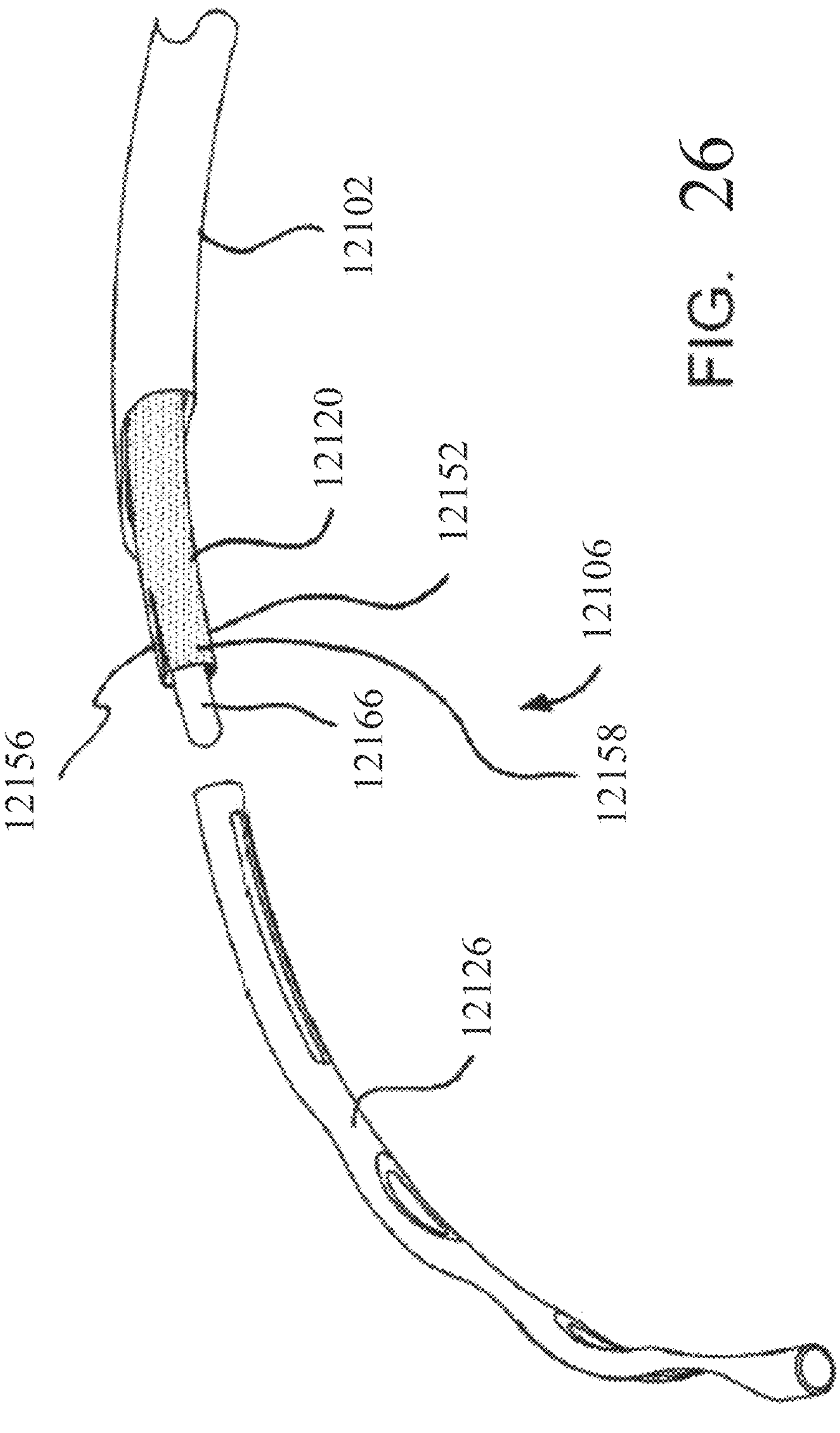
FIG. 26 is an additional perspective view of the assembly shown in the previous Figure.

FIG. 26 is an additional perspective view showing the assembly 12106 shown in the previous Figure. In the embodiment of FIG. 26, core 12166 and sheath 12120 have been moved in a proximal direction relative to implant 12126. With reference to FIG. 26, it will be appreciated that implant 12126 is now disposed outside of sheath 12120. Some methods in accordance with the present detailed description include the step of applying a proximally directed force to sheath 12120 and core 12166 while providing a distally directed reactionary force on implant 12126 to prevent implant 12126 from moving proximally. When this is the case, implant 12126 may pass through distal aperture 12154 of sheath 12120 as sheath 12120 is retracted over implant 12126.

In the embodiment of FIG. 26, distal portion 12152 of sheath 12120 comprises a first region 12156 and a second region 12158. The frangible connection between first region 12156 and second region 12158 has been broken in the embodiment of FIG. 26. This frangible connection may be selectively broken, for example, when sheath 12120 is moved in a proximal direction relative to implant 12126 due to the larger diameter of implant 12126 with respect to the diameters of distal portion 12152 and opening 12154 of sheath 12120. With reference to FIG. 26, it will be appreciated that the width of distal aperture 12154 becomes larger when the frangible connection is broken.

With reference to the Figures described above, it will be appreciated that methods in accordance with the present detailed description may be used to position a distal portion of an implant in Schlemm's canal of an eye. A method in accordance with the present detailed description may include the step of advancing a distal end of a cannula through a cornea of the eye so that a distal portion of the cannula is disposed in the anterior chamber of the eye. The cannula may be used to access Schlemm's canal, for example, by piercing the wall of Schlemm's canal with a distal portion of the cannula. A distal portion of a sheath may be advanced out of a distal port of the cannula and into Schlemm's canal. An ocular implant may be disposed inside the sheath while the distal portion of the sheath is advanced into Schlemm's canal.

In some useful methods, the ocular implant comprises a body defining a plurality of apertures and the method includes the step of covering the apertures with a sheath. When this is the case, the distal portion of the implant may be advanced into Schlemm's canal while the apertures are covered by the sheath. Covering the apertures as the implant is advanced into Schlemm's canal may reduce the trauma inflicted on Schlemm's canal by the procedure. The apertures may be uncovered, for example, after the implant has reached a desired location (e.g., inside Schlemm's canal).

The apertures of the implant may be uncovered, for example, by moving the sheath in a proximal direction relative to the implant. In some applications, this may be accomplished by applying a proximal directed force to the sheath while holding the implant stationary. The implant may be held stationary, for example, by applying a distally directed reaction force on the implant. In one embodiment, a distally directed reaction force is provided by pushing on a proximal end of the implant with a push tube.

Some methods include the step of ceasing advancement of the sheath into Schlemm's canal when a proximal portion of the implant remains in an anterior chamber of the eye and a distal portion of the implant lies in Schlemm's canal. When this is the case, only a distal portion of the implant is advanced into Schlemm's canal. The portion of the implant extending out of Schlemm's canal and into the anterior chamber may provide a path for fluid flow between the anterior chamber and Schlemm's canal.

An assembly may be created by placing a core in a channel defined by the ocular implant. A sheath may be placed around the implant and the core. For example, the core and the implant may then be inserted into the lumen of a sheath. By way of another example, the sheath may be slipped over the implant and the core. The core may be withdrawn from the channel defined by the ocular implant, for example, after the implant has been delivered to a desired location.

The core may be withdrawn from the channel, for example, by moving the core in a proximal direction relative to the implant. In some applications, this may be accomplished by applying a proximal directed force to the core while holding the implant stationary. The implant may be held stationary, for example, by applying a distally directed reaction force on the implant. In one embodiment, a distally directed reaction force is provided by pushing on a proximal end of the implant with a push tube.

The core, the implant, and the sheath may be advanced into Schlemm's canal together. Once the implant is in a desired location, the core and the sheath may be withdrawn from the Schlemm's canal leaving the implant in the desired location. In some methods, the core and the sheath are withdrawn from Schlemm's canal simultaneously.

Figure 27B:
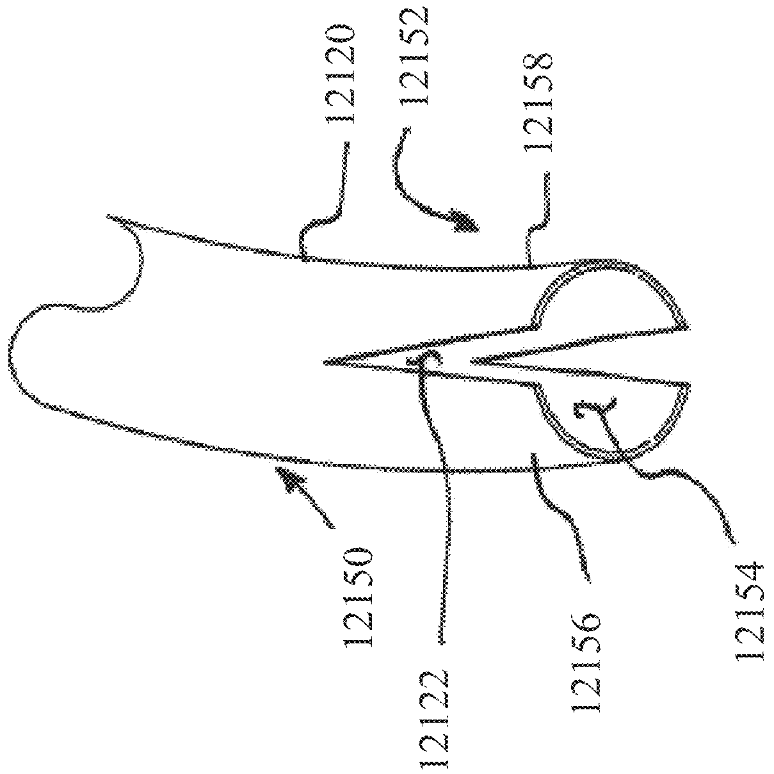
FIG. 27A and FIG. 27B are perspective views showing a sheath in accordance with the present detailed description.
Figure 27A:
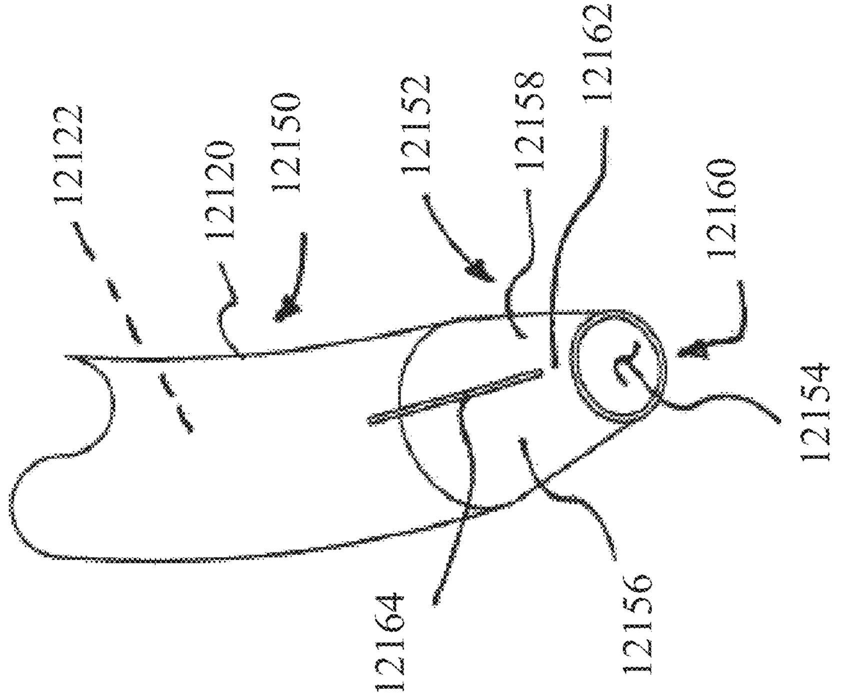

FIG. 27A and FIG. 27B are perspective views showing a sheath 12120 in accordance with the present detailed description. FIG. 27A and FIG. 27B may be referred to collectively as FIG. 27. Sheath 12120 of FIG. 27 comprises a proximal portion 12150 defining a lumen 12122 and a distal portion 12152 defining a distal aperture 12154. With reference to FIG. 27, it will be appreciated that lumen 12122 is generally larger than distal aperture 12154.

In the embodiment of FIG. 27A, distal portion 12152 of sheath 12120 comprises a first region 12156, a second region 12158, and a frangible connection 12160 between first region 12156 and second region 12158. In FIG. 27A, a slit 12164 defined by distal portion 12152 is shown disposed between first region 12156 and second region 12158. In the embodiment of FIG. 27A, frangible connection 12160 comprises a bridge 12162 extending across slit 12164.

In the embodiment of FIG. 27B, frangible connection 12160 has been broken. Frangible connection 12160 may be selectively broken, for example, by moving sheath 12120 in a proximal direction relative to an implant disposed in lumen 12122 having a diameter larger than the diameters of distal opening 12154 and distal portion 12152 of sheath 12120. With reference to FIG. 27, it will be appreciated that distal aperture 12154 becomes larger when frangible connection 12160 is broken.

In the embodiment of FIG. 27, the presence of slit 12164 creates a localized line of weakness in distal portion 12152 of sheath 12120. This localized line of weakness causes distal portion 12152 to selectively tear in the manner shown in FIG. 27. It is to be appreciated that distal portion 12152 may comprise various elements that create a localized line of weakness without deviating from the spirit and scope of the present detailed description. Examples of possible elements include: a skive cut extending partially through the wall of distal portion 12120, a series of holes extending through the wall of distal portion 12120, a perf cut, a crease, and a score cut.

Figure 28:
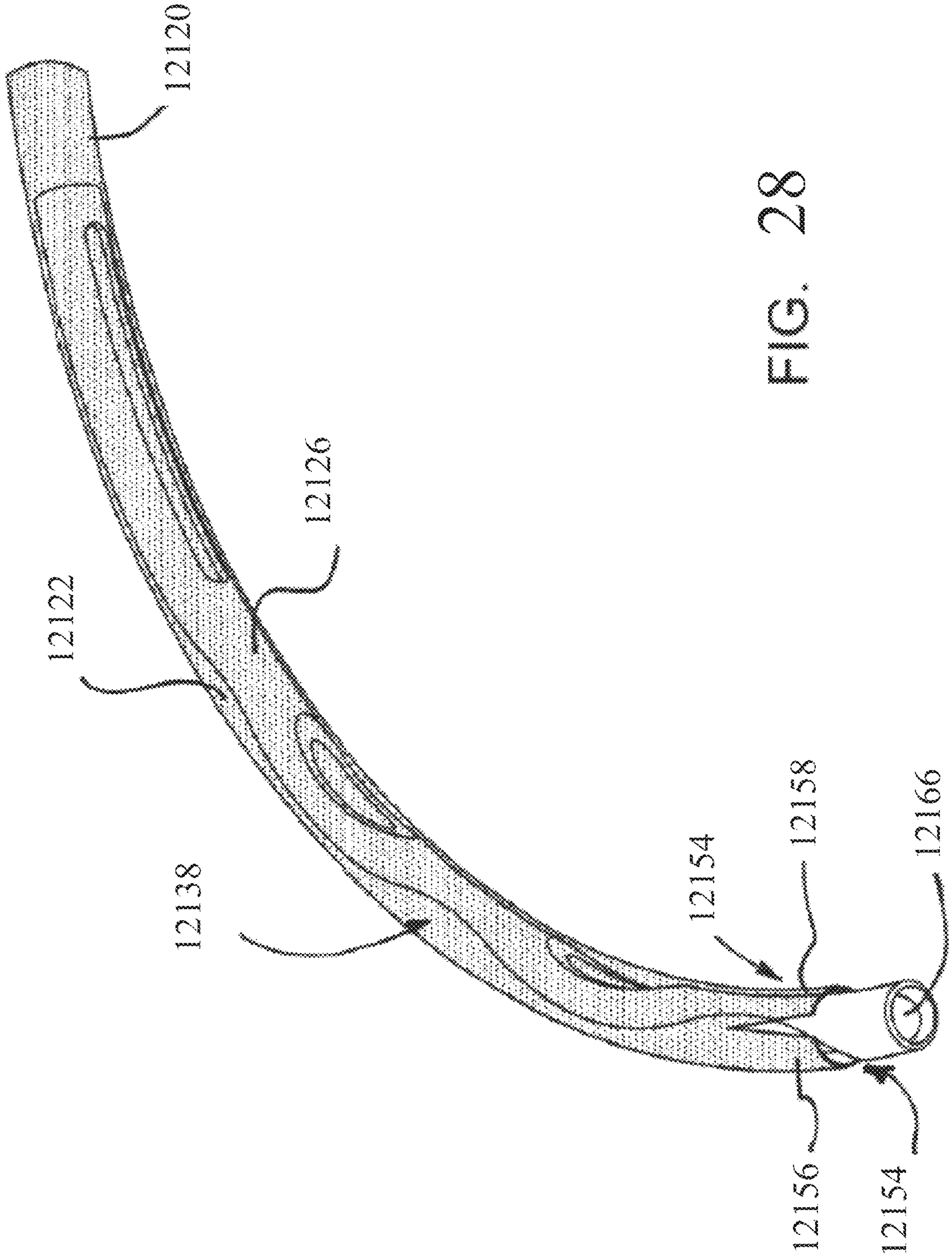
FIG. 28 is a perspective view of an assembly including the sheath shown in the previous Figure.

FIG. 28 is a perspective view of an assembly including sheath 12120 shown in the previous Figure. In the embodiment of FIG. 28, an implant 12126 is shown extending through distal aperture 12154 defined by distal portion 12152 of sheath 12120. Implant 12126 defines a channel 12138. In FIG. 28, a core 12166 can be seen resting in channel 12138. Implant 12126 and core 12166 extend proximally into lumen 12122 defined by sheath 12120. Distal portion 12152 of sheath 12120 comprises a first region 12156 and a second region 12158.

Figure 29B:
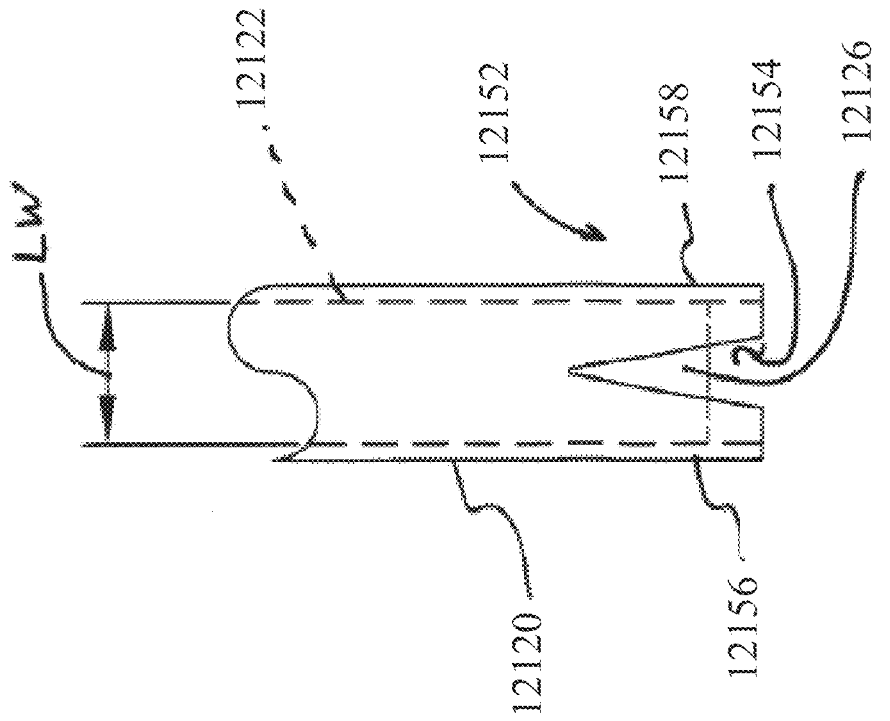
FIG. 29A and FIG. 29B are simplified plan views showing a sheath in accordance with the present detailed description.
Figure 29A:
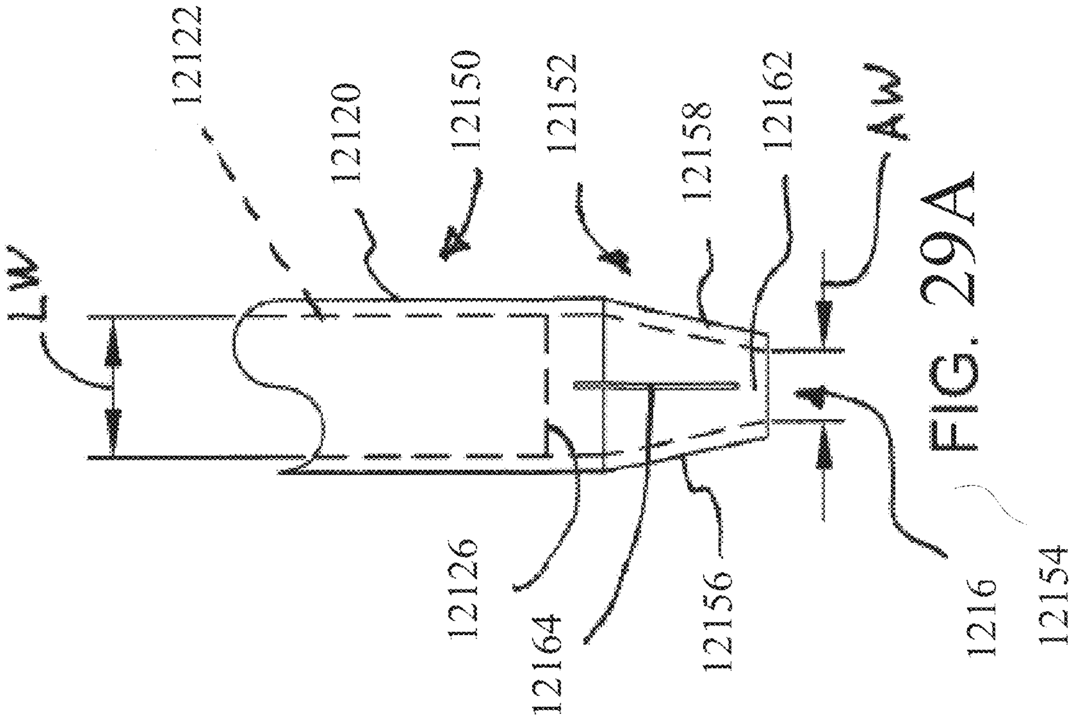

FIG. 29A and FIG. 29B are simplified plan views showing a sheath 12120 in accordance with the present detailed description. Sheath 12120 comprises a distal portion 12152 including a first region 12156, a second region 12158 and a frangible connection between first region 12156 and second region 12158. In the embodiment of FIG. 19A, frangible connection 12160 is intact. In the embodiment of FIG. 19B, frangible connection 12160 is broken. FIG. 29A and FIG. 29B may be referred to collectively as FIG. 29.

Sheath 12120 of FIG. 29 comprises a proximal portion 12150 defining a lumen 12122. In the embodiment of FIG. 29, an implant 12126 is disposed in lumen 12122. Lumen 12122 fluidly communicates with a distal aperture 12154 defined by distal portion 12152 of sheath 12120. Distal portion 12152 includes a slit 12164 disposed between first region 12156 and second region 12158. In FIG. 29A, a bridge 12162 can be seen spanning slit 12164. In some useful embodiments, distal portion 12152 of sheath 12120 has a first hoop strength and proximal portion 12150 sheath 12120 has a second hoop strength. The first hoop strength may be limited by the frangible connection in the embodiment of FIG. 29A. When this is the case, the second hoop strength is greater than the first hoop strength.

Sheath 12120 of FIG. 29 comprises a proximal portion 12150 defining a lumen 12122 and a distal portion 12152 defining a distal aperture 12154. Lumen 12122 has a lumen width LW. Distal aperture has an aperture width AW when frangible connection 12160 is intact. With reference to FIG. 29B, it will be appreciated that the distal aperture 12154 is free to open further when frangible connection 12160 is broken.

In some useful embodiments, lumen width LW of lumen 12122 is equal to or greater than the width of an implant 12126 disposed in lumen 12122. In some of these useful embodiments, aperture width AW is smaller than the width of the implant 12126. When this is the case, frangible connection 12160 can be selectively broken by moving sheath 12120 in a proximal direction relative to the implant 12126.

Figures 30A, 30B, 30C:
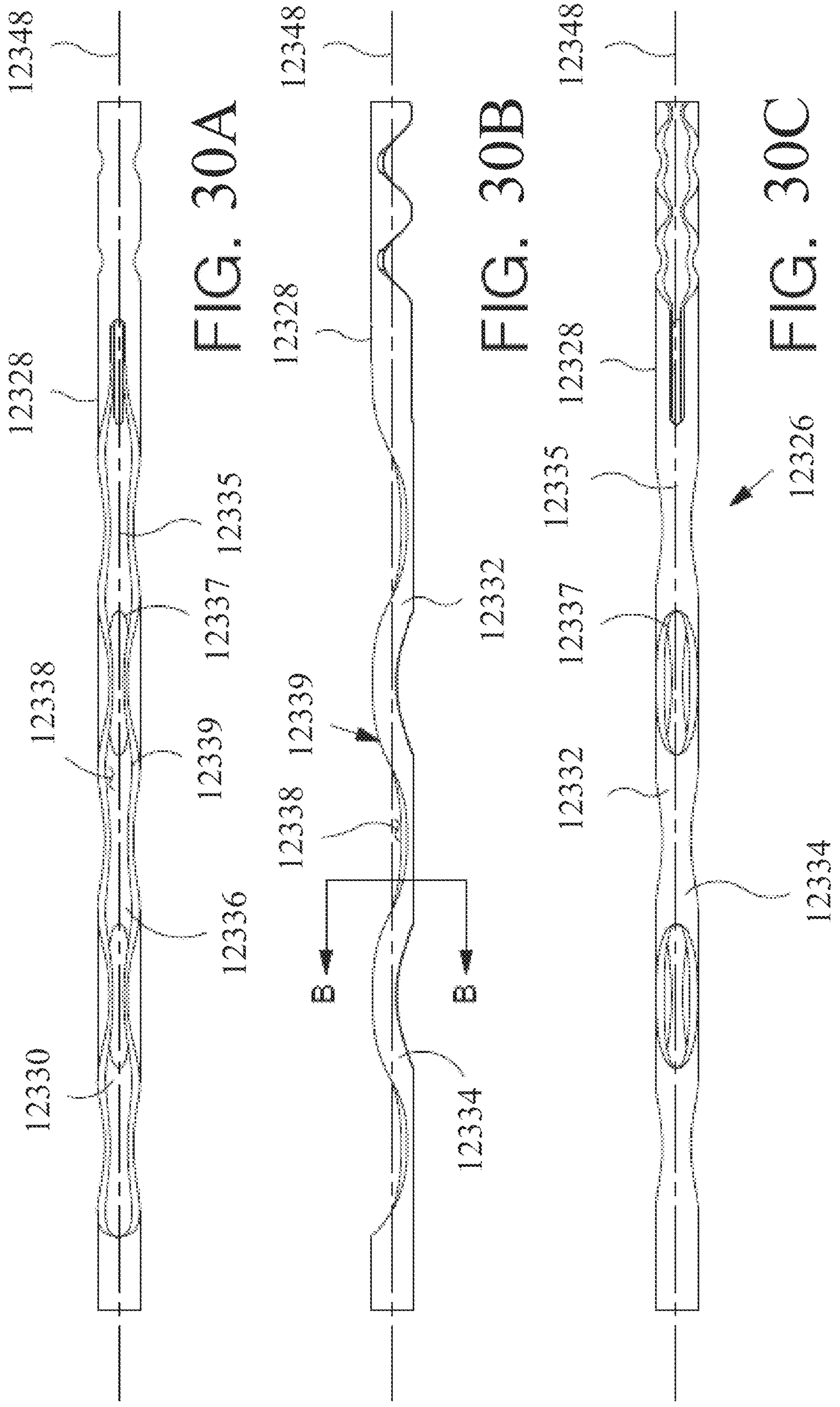
FIG. 30A, FIG. 30B and FIG. 30C are plan views showing an implant in accordance with the present detailed description.

FIG. 30A, FIG. 30B and FIG. 30C are multiple plan views of an implant 12326 in accordance with the present detailed description. FIG. 30A, FIG. 30B and FIG. 30C may be referred to collectively as FIG. 1309. FIG. 30A may be referred to as a top view of implant 12326, FIG. 30B may be referred to as a side view of implant 12326, and FIG. 30C may be referred to as a bottom view of implant 12326. The terms top view, side view, and bottom view are used herein as a convenient method for differentiating between the views shown in FIG. 30. It will be appreciated that the implant shown in FIG. 30 may assume various orientations without deviating from the spirit and scope of this detailed description. Accordingly, the terms top view, side view, and bottom view should not be interpreted to limit the scope of the invention recited in the attached claims.

Ocular implant 12326 of FIG. 30 comprises a body 12328 that extends along a longitudinal central axis 12348. Body 12328 of ocular implant 12326 has a first major surface 12330 and a second major surface 12332. In the embodiment of FIG. 30, body 12328 is curved about longitudinal central axis 12348 so that first major surface 12330 comprises a concave surface 12336 and second major surface 12332 comprises a convex surface 12334.

A distal portion of body 12328 defines a longitudinal channel 12338 including a channel opening 12339. Channel opening 12339 is disposed diametrically opposite a central portion 12335 of concave surface 12336. In the embodiment of FIG. 30, central portion 12335 of concave surface 12336 defines a plurality of apertures 12337. Each aperture 12337 fluidly communicates with channel 12338.

Figure 31:
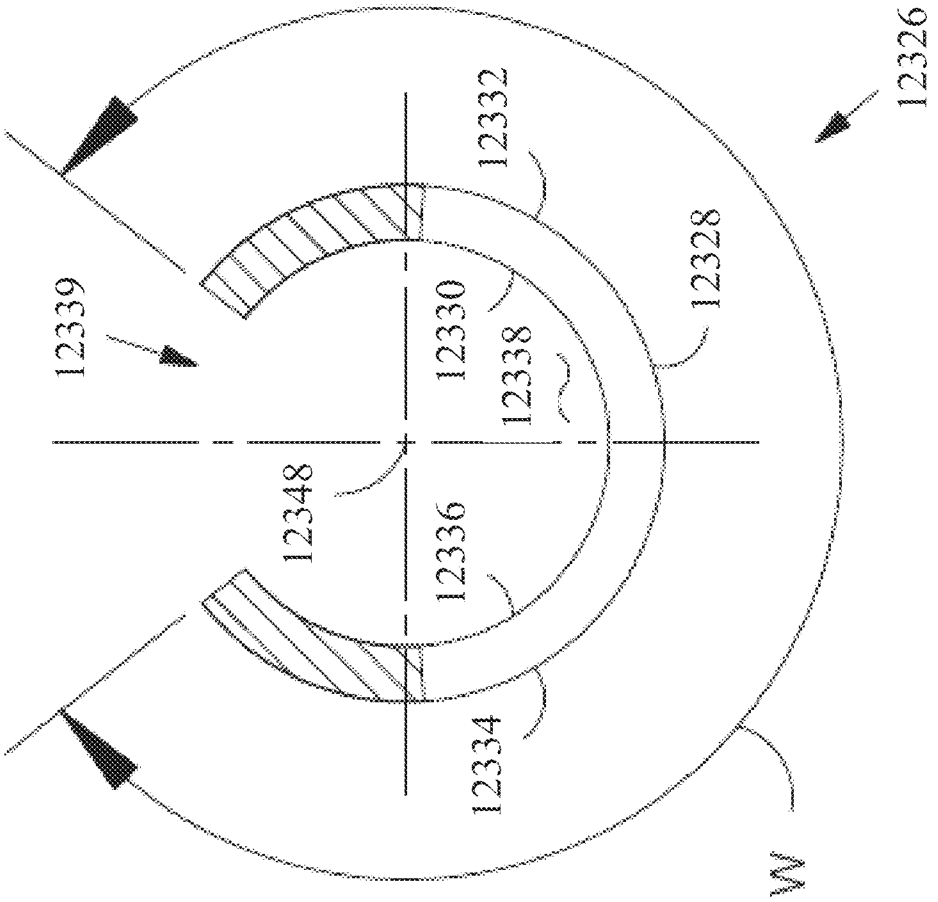
FIG. 31 is a lateral cross-sectional view of an ocular implant taken along section line A-A shown in the previous Figure.

FIG. 31 is a lateral cross-sectional view of ocular implant 12326 taken along section line B-B shown in the previous Figure. Ocular implant 12326 comprises a body 12328 having a first major surface 12330 and a second major surface 12332. With reference to FIG. 31, it will be appreciated that body 12328 curves around a longitudinal central axis 12348 so that first major surface 12330 comprises a concave surface 12336 and second major surface 12332 comprises a convex surface 12334. The concave surface 12336 of body 12328 defines a longitudinal channel 12338 having a channel opening 12339. As shown in FIG. 31, body 12328 has a circumferential extent that spans an angle W. In the embodiment of FIG. 31, angle W has a magnitude that is greater than one hundred eighty degrees.

Figure 32:
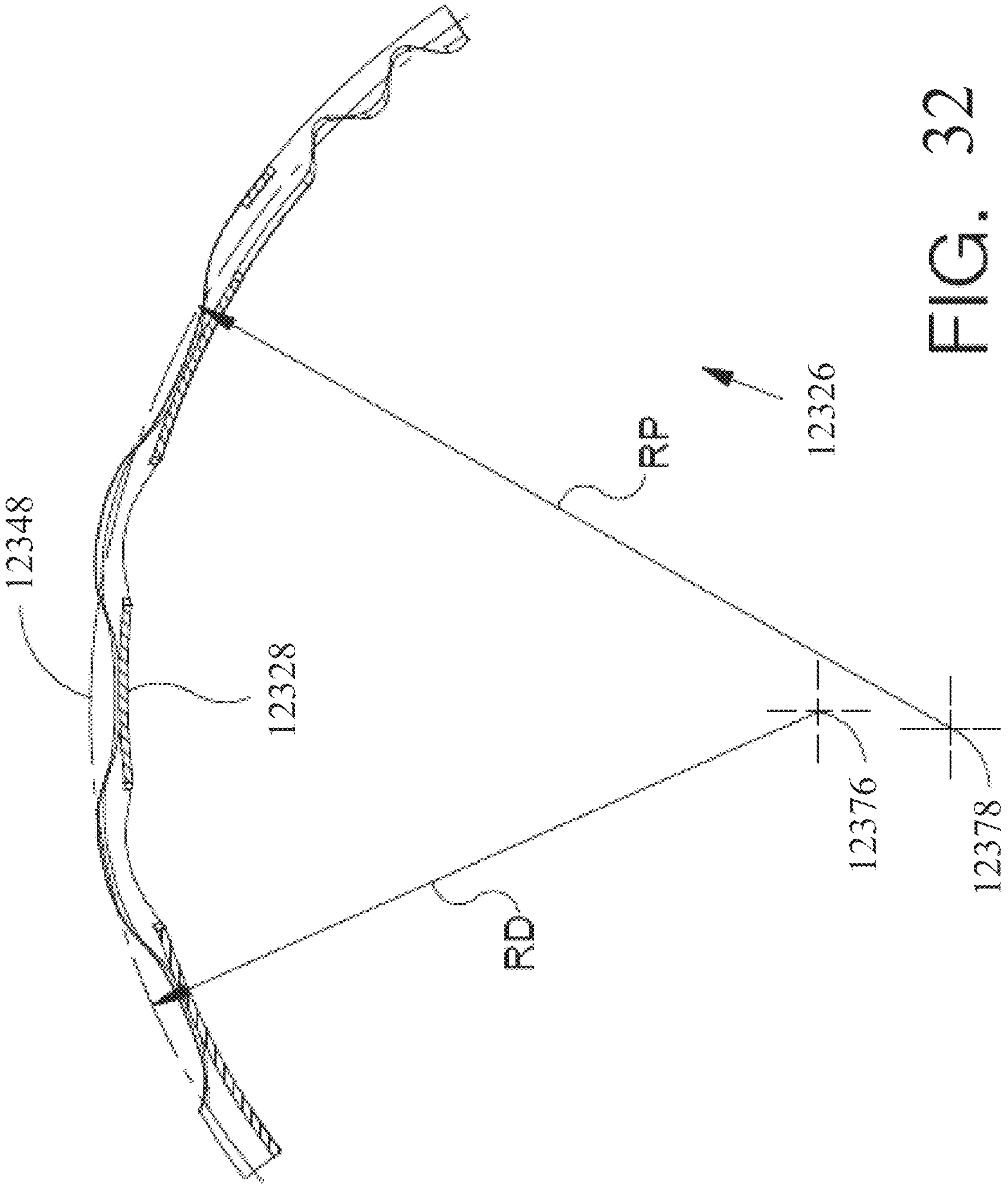
FIG. 32 is a plan view showing an implant in accordance with the present detailed description.

FIG. 32 is a cross-sectional view showing an implant 12326 in accordance with the present detailed description. Ocular implant 12326 of FIG. 32 comprises a body 12328 that extends along a generally curved longitudinal central axis 348. In the embodiment of FIG. 32, body 12328 has a distal radius of curvature RD and a proximal radius of curvature RP. Each radius of curvature is represented with an arrow in FIG. 32. Distal radius of curvature RD is represented by an arrow extending between a first lateral central axis 12376 and a distal portion of longitudinal central axis 12348. Proximal radius of curvature RP is represented by an arrow extending between a second lateral central axis 12378 and a proximal portion of longitudinal central axis 12348. In the embodiment of FIG. 32, body 12328 of ocular implant 12326 has an at rest shape that is generally curved. This at rest shape can be established, for example, using a heat-setting process. The rest shape of the implant can be generally aligned with the radius of curvature of Schlemm's canal in a human eye.

Figures 33A, 33B, 33C:
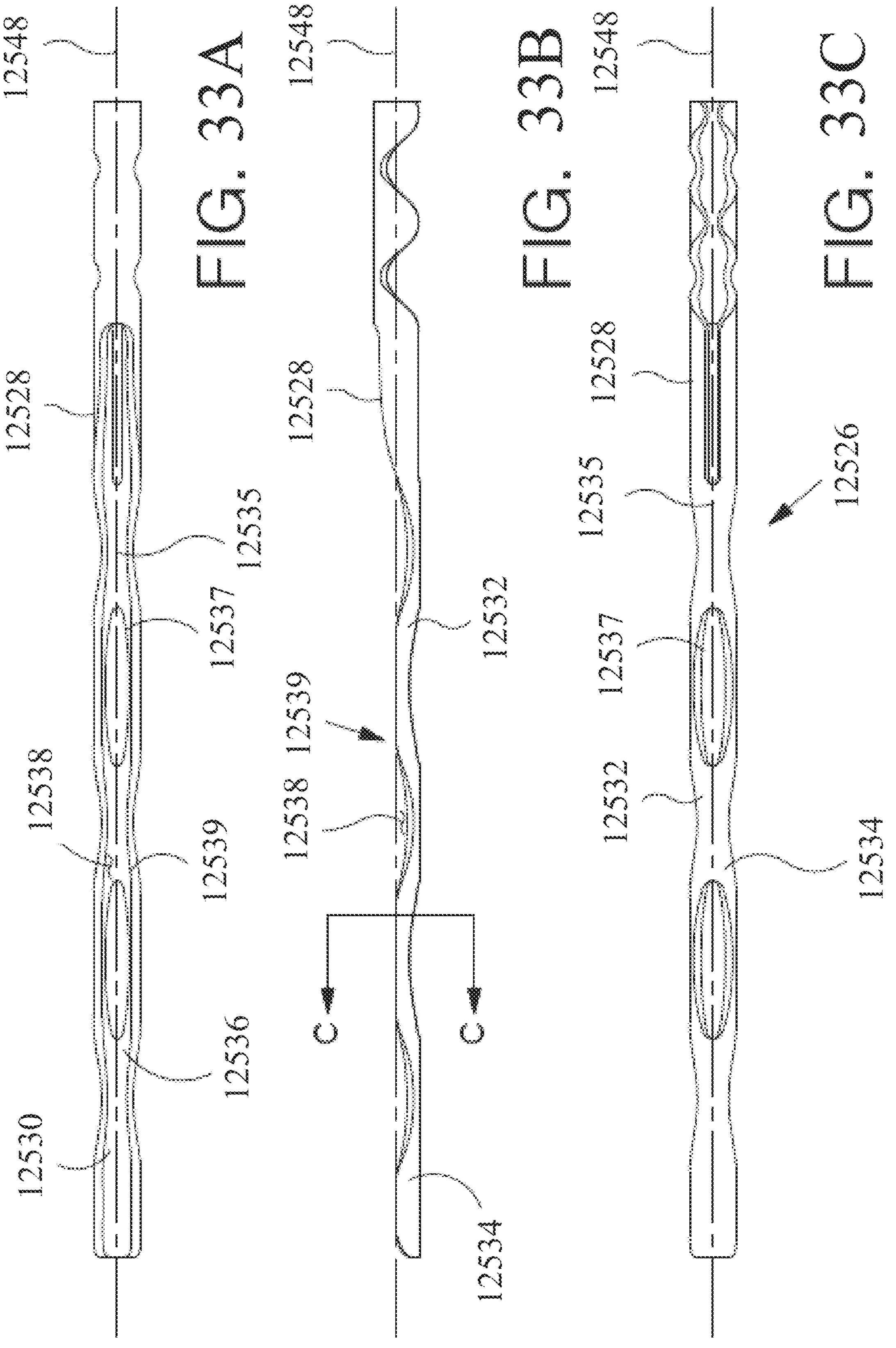
FIG. 33A, FIG. 33B and FIG. 33C are plan views showing an additional implant in accordance with the present detailed description.

FIG. 33A, FIG. 33B and FIG. 33C are multiple plan views of an implant 12526 in accordance with the present detailed description. FIG. 33A, FIG. 33B and FIG. 33C may be referred to collectively as FIG. 33. FIG. 33A may be referred to as a top view of implant 12526, FIG. 33B may be referred to as a side view of implant 12526, and FIG. 33C may be referred to as a bottom view of implant 12526. The terms top view, side view, and bottom view are used herein as a convenient method for differentiating between the views shown in FIG. 33. It will be appreciated that the implant shown in FIG. 33 may assume various orientations without deviating from the spirit and scope of this detailed description.

Accordingly, the terms top view, side view, and bottom view should not be interpreted to limit the scope of the invention recited in the attached claims.

Ocular implant 12526 of FIG. 33 comprises a body 12528 that extends along a longitudinal central axis 12548. Body 12528 of ocular implant 12526 has a first major surface 12530 and a second major surface 12532. In the embodiment of FIG. 33, body 12528 is curved about longitudinal central axis 12548 so that first major surface 12530 comprises a concave surface 12536 and second major surface 12532 comprises a convex surface 12534.

A distal portion of body 12528 defines a longitudinal channel 12538 including a channel opening 12539. Channel opening 12539 is disposed diametrically opposite a central portion 12535 of concave surface 12536. In the embodiment of FIG. 33, central portion 12535 of concave surface 12536 defines a plurality of apertures 12537. Each aperture 12537 fluidly communicates with channel 12538.

Figure 34:
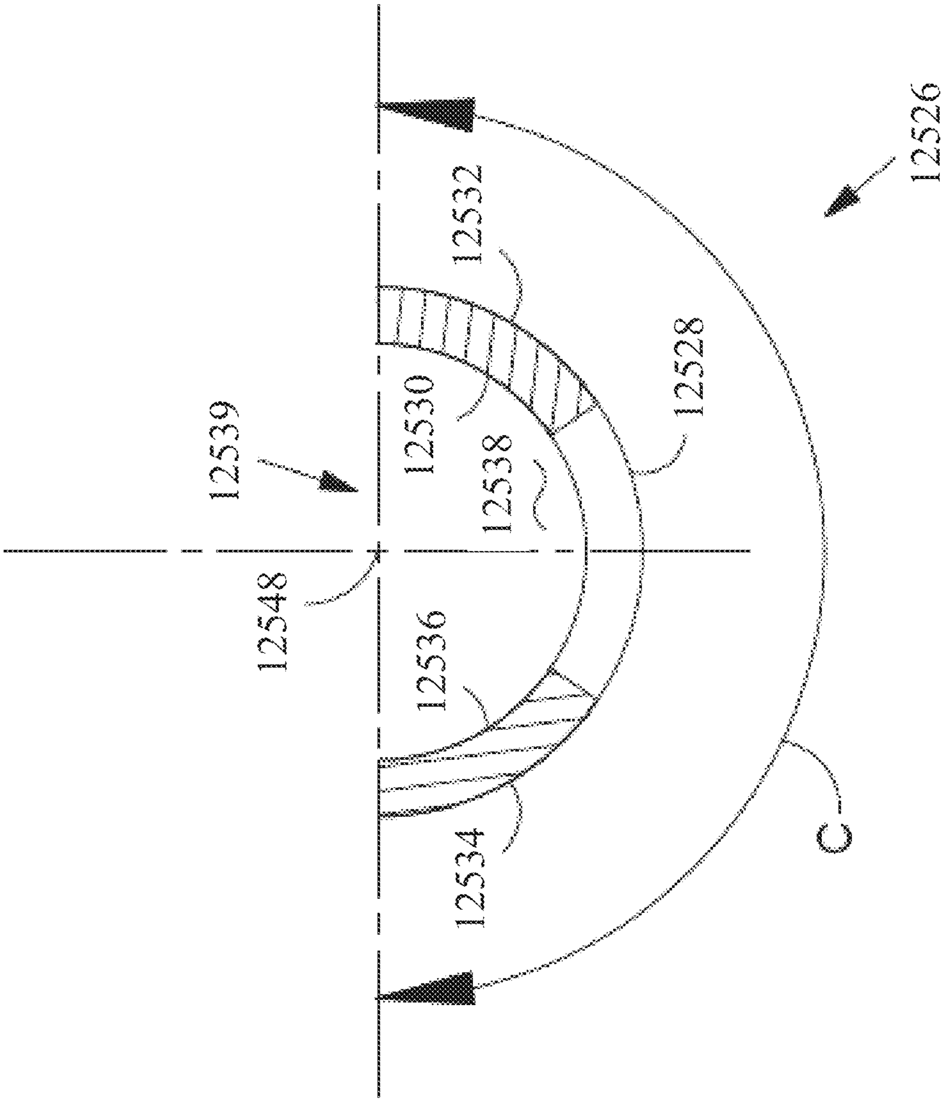
FIG. 34 is a lateral cross-sectional view of an ocular implant taken along section line B-B shown in the previous Figure.

FIG. 34 is a lateral cross-sectional view of ocular implant 12526 taken along section line C-C shown in the previous Figure. Ocular implant 12526 comprises a body having a first major side 12530 and a second major side 12532. With reference to FIG. 34, it will be appreciated that body 12528 curves around a longitudinal central axis 1248 so that first major side 12530 comprises a concave surface 12536 and second major side 12532 comprises a convex surface 12534. The concave surface 12536 of body 12528 defines a longitudinal channel 12538 having a channel opening 12539. As shown in FIG. 34, body 12528 has a circumferential extent that spans an angle C. In the embodiment of FIG. 34, angle C has a magnitude that is about one hundred eighty degrees. Some useful implants in accordance with the present detailed description comprise a body having a circumferential extend that spans an angle that is about one hundred eighty degrees. Some particularly useful implants in accordance with the present detailed description comprise a body having a circumferential extend that spans an angle that is equal to or less than one hundred eighty degrees.

Figure 35:
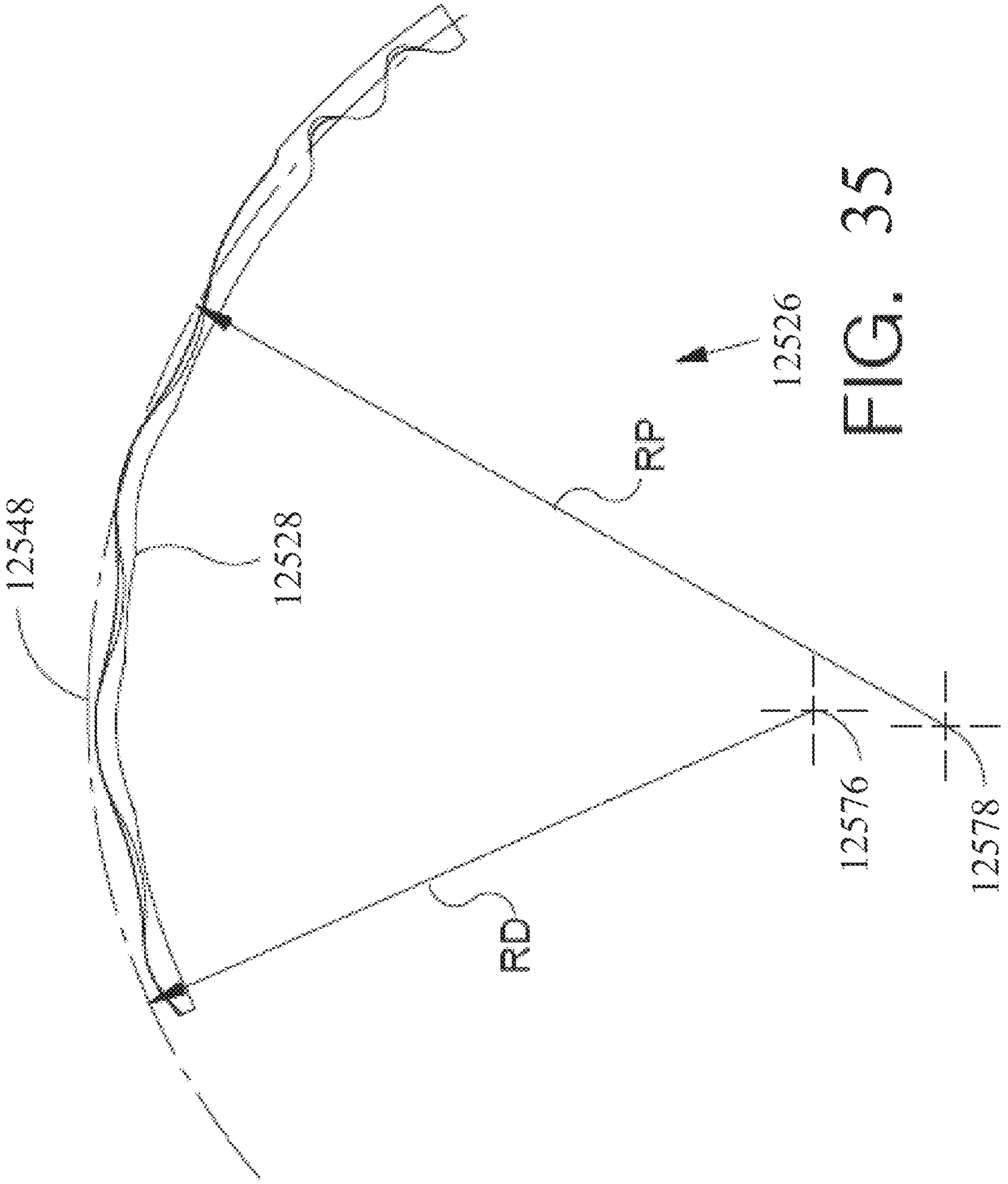
FIG. 35 is a plan view showing an implant in accordance with the present detailed description.

FIG. 35 is a plan view showing an implant 12526 in accordance with the present detailed description. Ocular implant 12526 of FIG. 35 comprises a body 12528 that extends along a generally curved longitudinal central axis 12548. In the embodiment of FIG. 35, body 12528 has a distal radius of curvature RD and a proximal radius of curvature RP. Each radius of curvature is represented with an arrow in FIG. 35. Distal radius of curvature RD is represented by an arrow extending between a first lateral central axis 12576 and a distal portion of longitudinal central axis 12548. Proximal radius of curvature RP is represented by an arrow extending between a second lateral central axis 12578 and a proximal portion of longitudinal central axis 12548. In the embodiment of FIG. 35, body 12528 of ocular implant 12526 has an at rest shape that is generally curved. This at rest shape can be established, for example, using a heat-setting process.

Figures 36A, 36B, 36C, 36D:
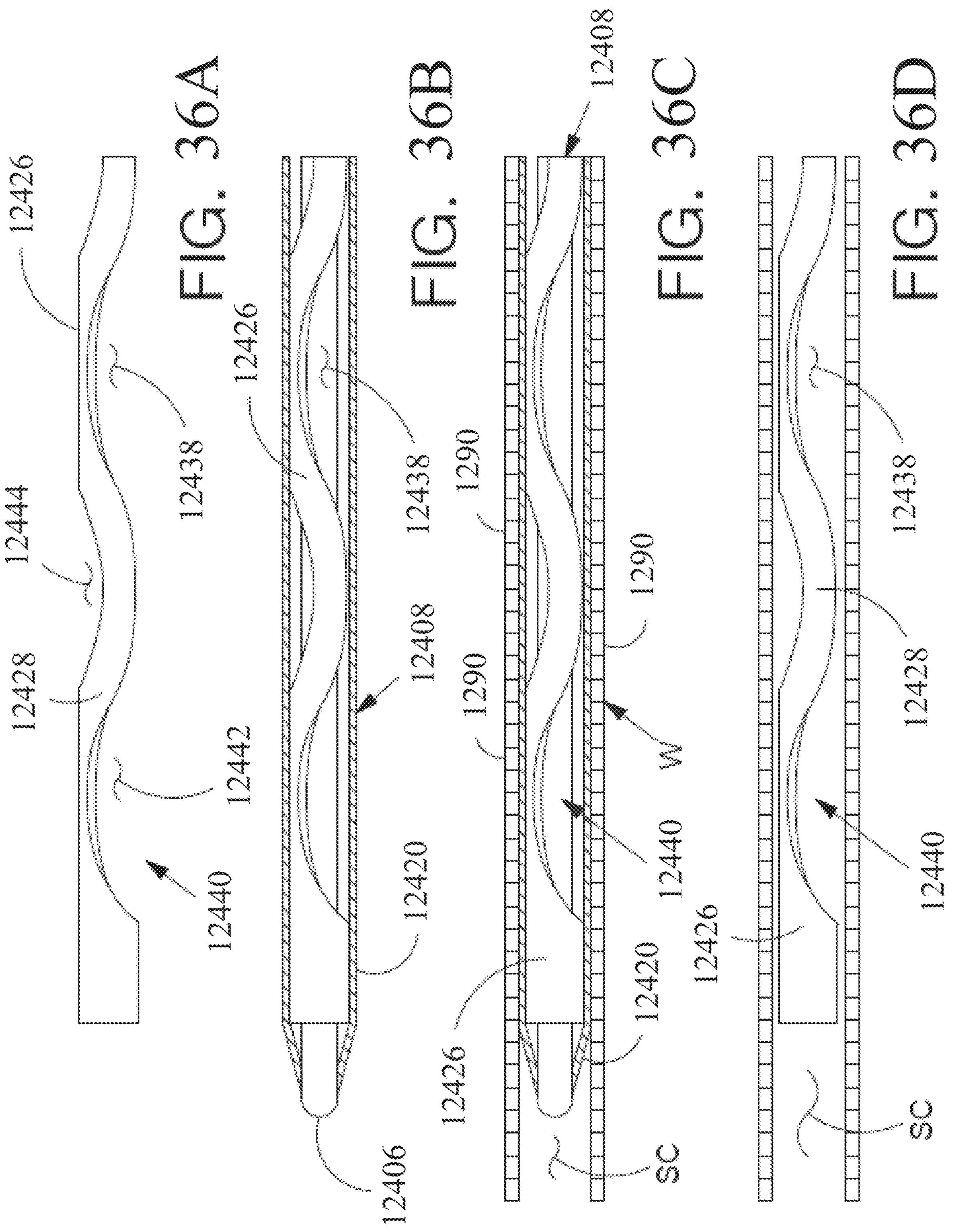
FIG. 36A through FIG. 36D are a series of plan views illustrating a method in accordance with the present detailed description.

FIG. 36A through FIG. 36D are a series of plan views illustrating a method in accordance with the present detailed description. FIG. 36A is a plan view showing an implant 12426. Implant 12426 comprises a body 12428 defining a plurality of openings 12440. Openings 12440 include a first opening 12442 and a second opening 12444.

FIG. 36B is a plan view showing an assembly 12408 including implant 12426. Assembly 12408 of FIG. 36B may be created by placing a core 12406 in a channel 12438 defined by implant 12426. A sheath 12420 may be placed around implant 12426 and core 12406. For example, core 12406 and implant 12426 may be inserted into a lumen defined by sheath 12420. By way of another example, sheath 12420 may be slipped over implant 12426 and core 12406.

FIG. 36C is a plan view showing assembly 12408 disposed in Schlemm's canal SC. The wall W of Schlemm's canal SC comprises a plurality of cells 1290. With reference to FIG. 36C, it will be appreciated that sheath 12420 is disposed between implant 12426 and cells 1290. A method in accordance with the present detailed description may include the step of advancing a distal end of a cannula through a cornea of the eye so that a distal portion of the cannula is disposed in the anterior chamber of the eye. The cannula may be used to access Schlemm's canal, for example, by piercing the wall of Schlemm's canal with a distal portion of the cannula. A distal portion of sheath 12420 may be advanced out of a distal port of the cannula and into Schlemm's canal SC. Ocular implant 12426 may be disposed inside sheath 12420 while the distal portion of sheath 12420 is advance into Schlemm's canal SC.

In the embodiment of FIG. 36C, ocular implant 12426 comprises a body defining a plurality of openings 12440. With reference to FIG. 36C, it will be appreciated that openings 12440 are covered by sheath 12420 and that a distal portion of implant 12426 may be advanced into Schlemm's canal while openings 12440 are covered by sheath 12420. Covering openings 12440 as implant 12426 is advanced into Schlemm's canal SC may reduce the trauma inflicted on cells 1290 by the procedure.

In some useful embodiments, sheath 12420 comprises a coating disposed on an outer surface thereof. The properties of the coating may be selected to further reduce the trauma inflicted on cells 1290 by the procedure. The coating may comprise, for example, a hydrophilic material. The coating may also comprise, for example, a lubricious polymer. Examples of hydrophilic materials that may be suitable in some applications include: polyalkylene glycols, alkoxy polyalkylene glycols, copolymers of methylvinyl ether and maleic acid poly(vinylpyrrolidone), poly(N-alkylacrylamide), poly(acrylic acid), poly(vinyl alcohol), poly(ethyleneimine), methyl cellulose, carboxymethyl cellulose, polyvinyl sulfonic acid, heparin, dextran, modified dextran and chondroitin sulphate.

In FIG. 36C, the distal portion of sheath 12420 is shown extending between a smaller, distal diameter and a larger, proximal diameter. In the embodiment of FIG. 36C, the distal portion of sheath 12420 has a generally tapered shape. The tapered transition of the distal portion of sheath 12420 may create a nontraumatic transition that dilates Schlemm's canal SC as sheath 12420 is advanced into Schlemm's canal SC. This arrangement may reduce the likelihood that skiving of wall W occurs as sheath 12420 is advanced into Schlemm's canal SC.

FIG. 36D is a plan view showing implant 12426 disposed in Schlemm's canal SC. In the embodiment of FIG. 36D, openings 12440 defined by body 12428 have been uncovered. Openings 12440 may be uncovered, for example, by moving sheath 12420 in a proximal direction relative to implant 12426. In some applications, this may be accomplished by applying a proximal directed force to sheath 12420 while holding implant 12426 stationary. Implant 12426 may be held stationary, for example, by applying a distally directed reaction force on implant 12426. In the embodiment of FIG. 36, a distally directed reaction force may be provided by pushing on a proximal end of implant 12426 with a push tube.

In the embodiment of FIG. 36D, core 12406 has been removed channel 12438 defined by implant 12426. Core 12406 may be withdrawn from channel 12438, for example, by moving core 12406 in a proximal direction relative to implant 12426. In some applications, this may be accomplished by applying a proximal directed force to core 12406 while holding implant 12426 stationary. Implant 12426 may be held stationary, for example, by applying a distally directed reaction force on implant 12426.

Figure 37B:
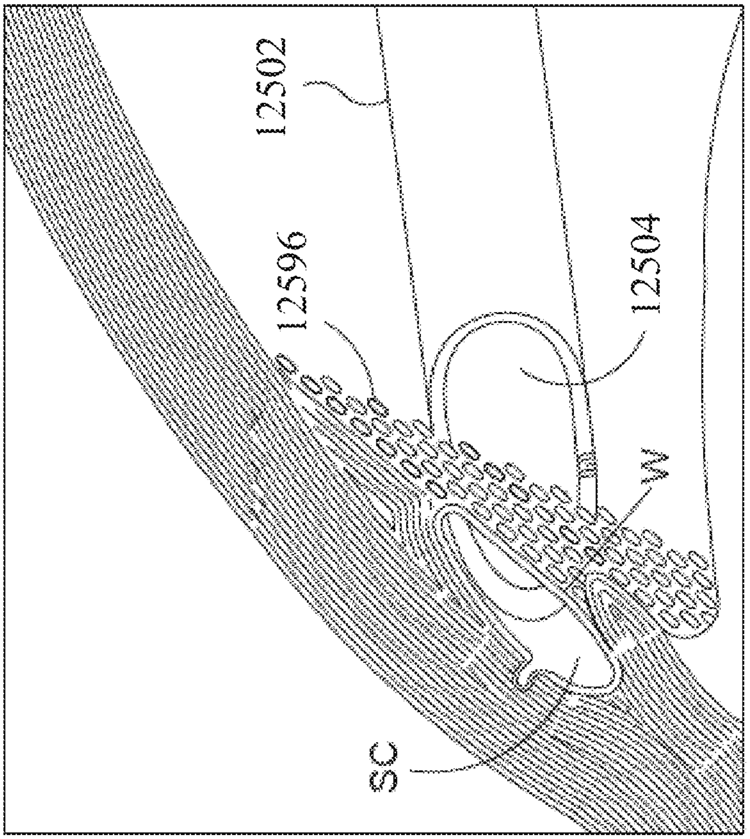
FIG. 37A through FIG. 37D are a series of section views illustrating a method in accordance with the present detailed description.
Figure 37A:
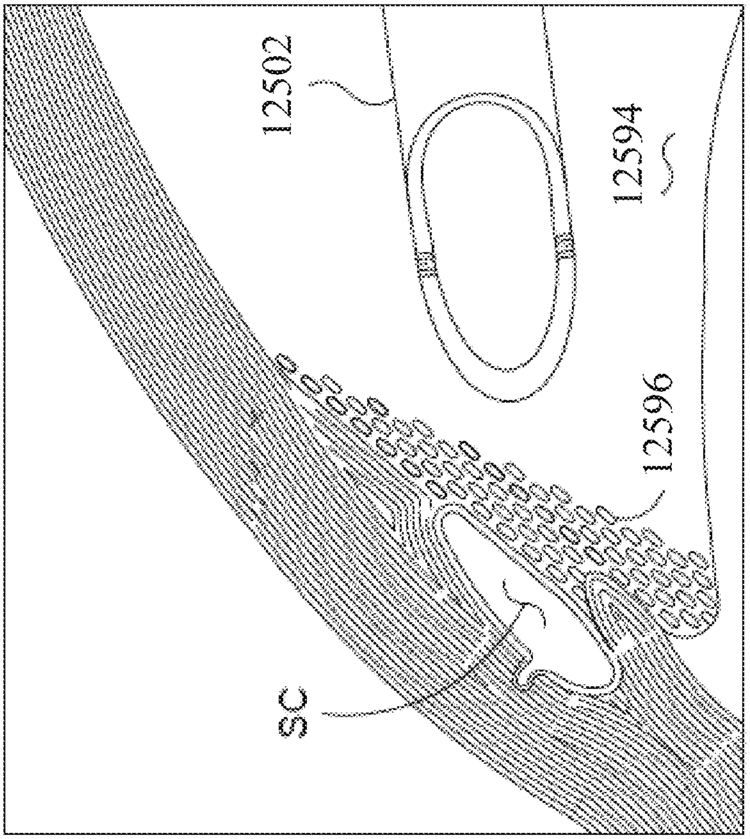

FIG. 37A through FIG. 37D are a series of section views illustrating a method in accordance with the present detailed description. The picture plane of FIG. 37A extends laterally across Schlemm's canal SC and the trabecular meshwork 12596 overlaying Schlemm's canal SC. In the embodiment of FIG. 37A, the distal end of a cannula 12502 has been positioned proximate Schlemm's canal SC. A method in accordance with the present detailed description may include the step of advancing the distal end of cannula 12502 through the cornea of an eye so that a distal portion of cannula 12502 is disposed in the anterior chamber 12594 of the eye.

FIG. 37B is an additional section view showing Schlemm's canal SC shown in the previous Figure. In FIG. 37B, a distal portion of cannula 502 is shown extending through a wall W of Schlemm's canal SC and trabecular meshwork 12596. A distal port 12504 of cannula 12502 fluidly communicates with Schlemm's canal in the embodiment of FIG. 37B.

Figure 37D:
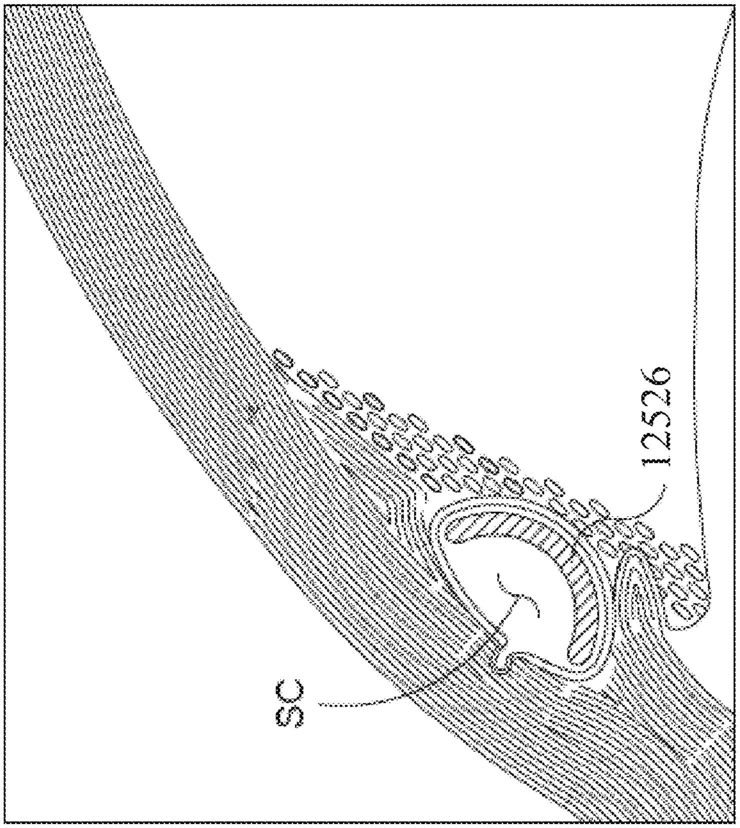
Figure 37C:
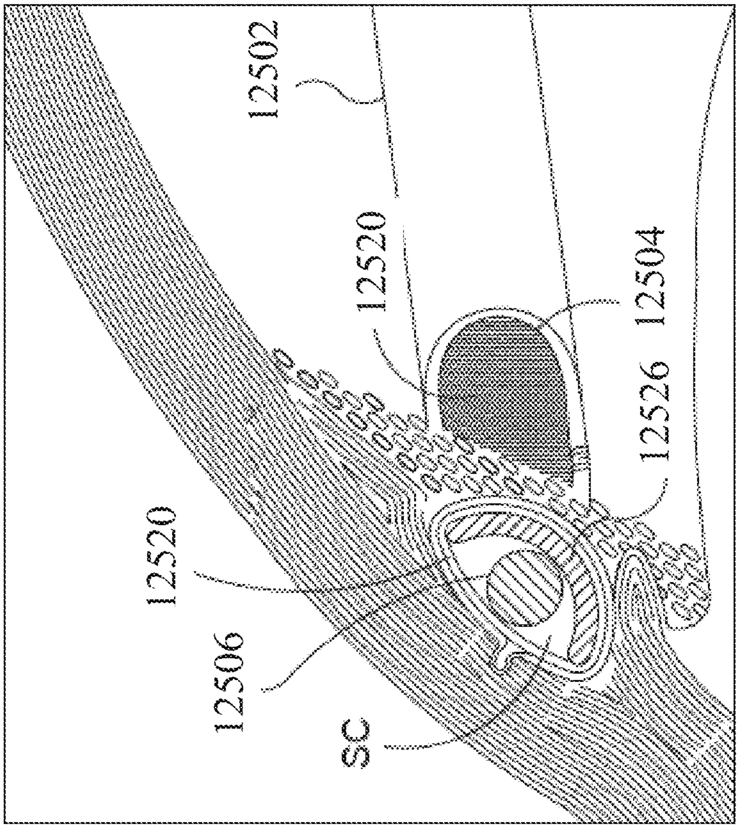

FIG. 37C is an additional section view showing Schlemm's canal SC shown in the previous Figure. In the embodiment of FIG. 37C, a distal portion of a sheath 12520 is shown extending through distal port 12504 of cannula 12502 and into Schlemm's canal SC. Methods in accordance with the present invention can be used to deliver an implant 12526 into Schlemm's canal SC. In these methods, a distal portion of sheath 12520 and a core 12506 may be advanced out of distal port 12504 of cannula 12502 and into Schlemm's canal SC. Ocular implant 12526 may be disposed inside sheath 12520 while the distal portion of sheath 12520 is advanced into Schlemm's canal SC.

FIG. 37D is an additional section view showing implant 12526 shown in the previous Figure. In the embodiment of FIG. 37D, sheath 12520, core 12506, and cannula 12502 have all been withdrawn from the eye. Implant 12526 is shown resting in Schlemm's canal SC in FIG. 37D.

Figure 38B:
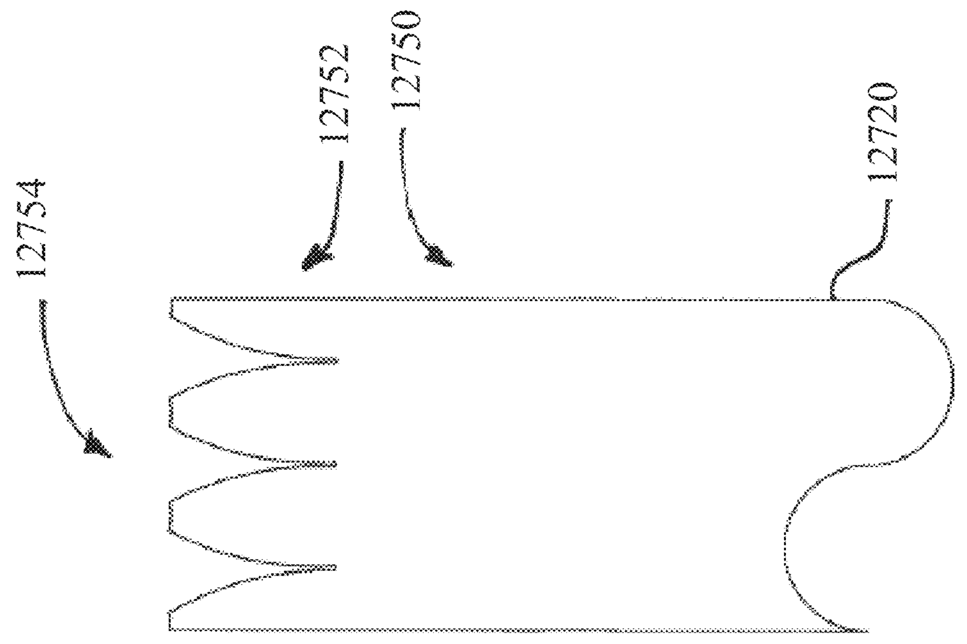
FIG. 38A and FIG. 38B are simplified plan views showing a sheath in accordance with the present detailed description.
Figure 38A:
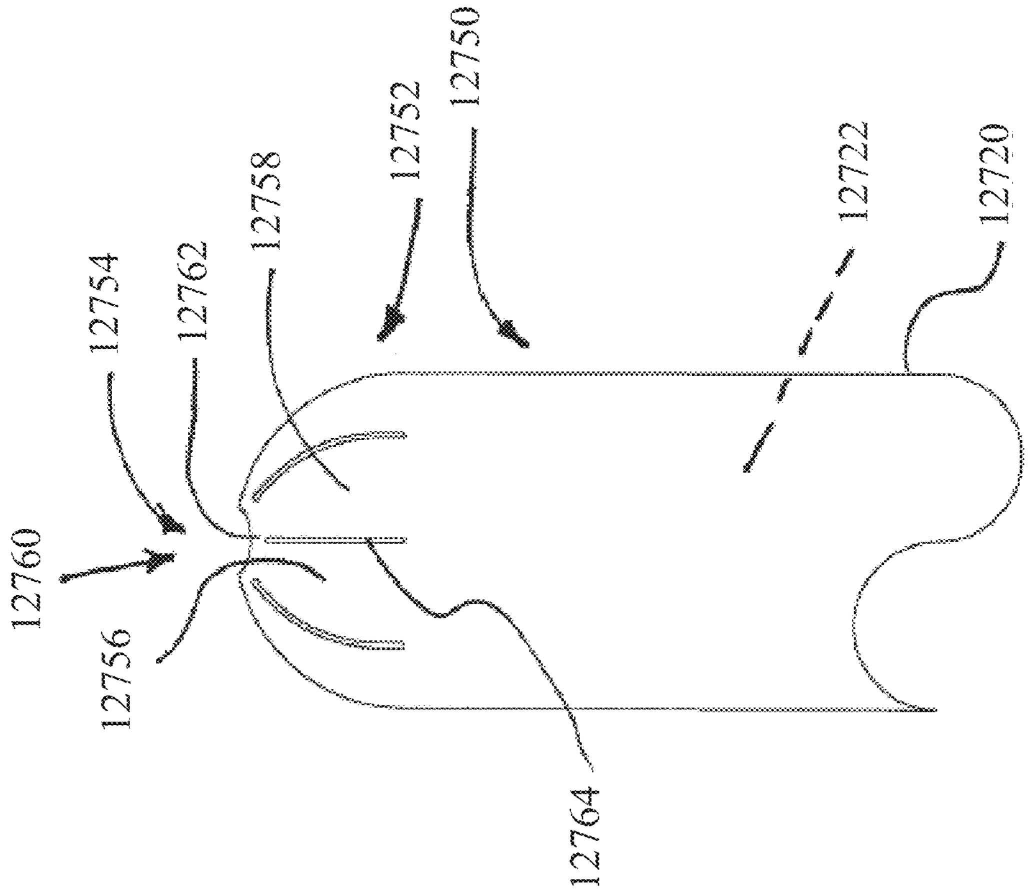

FIG. 38A and FIG. 38B are simplified plan views showing a sheath 12720 in accordance with the present detailed description. FIG. 38A and FIG. 38B may be referred to collectively as FIG. 38. Sheath 12720 of FIG. 38 comprises a proximal portion 12750 defining a lumen 12722 and a distal portion 12752 defining a distal aperture 12754. With reference to FIG. 38, it will be appreciated that lumen 12722 is generally larger than distal aperture 12754.

In the embodiment of FIG. 38A, distal portion 12752 of sheath 12720 comprises a first region 12756, a second region 12758, and a frangible connection 12760 between first region 12756 and second region 12758. In FIG. 38A, a first slit 12764 defined by distal portion 12752 is shown disposed between first region 12756 and second region 12758. In the embodiment of FIG. 38A, frangible connection 12760 comprises a bridge 12762 extending across first slit 12764. With reference to FIG. 38A, it will be appreciated that distal portion 12752 defines a number of slits in addition to first slit 12764.

In the embodiment of FIG. 38B, frangible connection 12760 has been broken. Frangible connection 12760 may be selectively broken, for example, by moving sheath 12720 in a proximal direction relative to an implant disposed in lumen 12722 having a diameter larger than the diameters of distal opening 12754 and distal portion 12752 of sheath 12720. With reference to FIG. 38, it will be appreciated that distal aperture 12754 becomes larger when frangible connection 12760 is broken.

In the embodiment of FIG. 38, the presence of slit 12764 creates a localized line of weakness in distal portion 12752 of sheath 12720. This localized line of weakness causes distal portion 12752 to selectively tear in the manner shown in FIG. 38. It is to be appreciated that distal portion 12752 may comprise various elements that create a localized line of weakness without deviating from the spirit and scope of the present detailed description. Examples of possible elements include: a skive cut extending partially through the wall of distal portion 12720, a series of holes extending through the wall of distal portion 12720, a perf cut, a crease, and a score cut.

In FIG. 38, distal portion 12752 of sheath 12720 is shown extending between distal opening 12754 and lumen 12722. In the embodiment of FIG. 38, distal portion 12752 of sheath 12720 has a blunt shape. The blunt shape of distal portion 12752 of sheath 12720 may create a nontraumatic transition that dilates Schlemm's canal as sheath 12720 is advanced into Schlemm's canal. This arrangement may reduce the likelihood that skiving of the canal wall occurs as sheath 12720 is advanced into Schlemm's canal.

Various fabrication techniques may be used to fabricate the ocular implant. For example, the ocular implant can be fabricated by providing a generally flat sheet of material, cutting the sheet of material, and forming the material into a desired shape. By way of a second example, the ocular implant may be fabricated by providing a tube and laser cutting openings in the tube to form the ocular implant.

The ocular implant of this invention can be fabricated from various biocompatible materials possessing the necessary structural and mechanical attributes. Both metallic and non-metallic materials may be suitable. Examples of metallic materials include stainless steel, tantalum, gold, titanium, and nickel-titanium alloys known in the art as Nitinol. Nitinol is commercially available from Memry Technologies (Brookfield, Conn.), TiNi Alloy Company (San Leandro, Calif.), and Shape Memory Applications (Sunnyvale, Calif.).

The ocular implant may include one or more therapeutic agents. One or more therapeutic agents may, for example, be incorporated into a polymeric coating that is deposited onto the outer surfaces of the struts and spines of the ocular implant. The therapeutic agent may comprise, for example, an anti-glaucoma drug. Examples of anti-glaucoma drugs include prostaglandin analogs. Examples of prostaglandin analogs include latanprost.

The implants of the present disclosure provide a treatment for glaucoma by combining the mechanism of trabecular meshwork (TM) bypass and Schlemm's canal (SC) dilation. The trabecular meshwork bypass is achieved through the openings, the longitudinal channel, and channel opening of the implants above, and Schlemm's canal dilation is achieved by supporting Schlemm's canal with the body of the implant itself.

A comprehensive mathematical model was developed in this disclosure to evaluate changes in fluid dynamics of aqueous humor outflow induced by combinations of trabecular mesh bypass and/or Schlemm's canal dilation, and to predict how the changes would affect outflow facility. First, a control eye was modeled after an ex vivo human anterior segment perfusion model using typical dimensions for the eye and Schlemm's canal. This was done in order to validate the model parameters with experimental data. Next, two combinations of bypass and dilation were modeled using the dimensional parameters of implants with 8 mm and 16 mm lengths. The mathematical model was used to predict outflow facilities in control and experimental simulations.

The mathematical model was developed to numerically simulate aqueous humor outflow based on the assumptions and physical principles that govern fluid flow. Schlemm's canal is modeled as a rectangular channel with width (w) and height (h), where h varies with the location (x) along the canal due to trabecular mesh deformation. The trabecular mesh is treated as an elastic membrane in the model. The ostia of collector channels (CC) are distributed uniformly along the outer wall of Schlemm's canal with the first collector channel located at x=0.6 mm or θ=6°. Collector channels are treated as individual sinks with flow rate, $J_{CC}$ (see the governing equation below). Schlemm's canal in the experimental simulations is modeled after either an 8 mm implant or 16 mm implant. The region of Schlemm's canal with an implant is also modeled as a rectangular channel but with width ($w_d$) and height ($h_d$) corresponding to the implant cross-sectional area.

The height of Schlemm's canal (h) is intra-ocular pressure (IOP) dependent. The dependence is assumed to be linear:

$$h=h_0*(1-\text{IOP}-\text{PSCE}) \quad (1)$$

Across the trabecular meshwork, the aqueous humor flux ($J_{TM}$) is dependent on the trabecular mesh resistance ($R_{TM}$) and is governed by:

$$J_{TM}=\frac{IOP-P_{SC}}{R_{TM}} \quad (2)$$

-continued $$\frac{dP}{dx} = \frac{12\mu}{wh^3}Q \quad (3)$$

$$\frac{dQ}{dx} = -J_{CC}(x - x_{CC}) \quad (4)$$

$$J_{CC} = \frac{P_{SC} - P_{epi}}{R_{CC}(x_{cc})} \quad (5)$$

In these equations, $P_{sc}$ is the fluid pressure in the Schlemm's canal, E is the Young's modulus of the trabecular meshwork, $h_0$ is the value of h when intra-ocular pressure=$P_{sc}$, $R_{TM}$ is the trabecular meshwork's resistance to fluid flow, Q is the flow rate along the SC, g is the viscosity of aqueous humor, $x_{cc}$ indicates locations of collector channel ostia in the Schlemm's canal, $J_{CC}$ is the flow rate in the collector channels, $P_{epi}$ is the pressure in the episcleral veins, and $R_{CC}$ is the flow resistance of collector channels that may depend on $x_{cc}$. Since Schlemm's canal is a ring-like channel, the boundary conditions at x=0 for $P_{sc}$ and Q are the same as those at x=L, where L is the circumferential length of Schlemm's canal.

In simulations with an implant such as those described herein, a portion of Schlemm's canal is stretched open. The implant inlet is assumed to be a uni-directional fluid source with zero flow resistance $P_{sc}$=IOP. The implant is modeled as a channel with three side walls, leaving the side facing the outer wall of Schlemm's canal open. For example, FIGS. 7A-7B show an implant having three "walls" comprising first strut 144, second strut 146, and spine 140 which leaves opening or channel 124 open and facing Schlemm's canal when implanted. The wall of the implant facing the inner wall of Schlemm's canal (spine 140) contains several windows (or openings), which allow the aqueous humor to enter SC through the TM.

Two scaffold designs are investigated in this disclosure. One has a total length of 8 mm with 3 windows and 3 spines (shown in FIGS. 2, 4, 11, 17, 19A-C, 30A-C, 32, 33A-C, 35); and another has a total length of 16 mm with 5 windows and 6 spines (shown in FIG. 6, 10, 21A). Individual dimensions of 8 mm and 16 mm implants are shown in Table 2A and 2B, respectively. The governing equations for the region of SC without the scaffold and RTM in window regions are equal to control parameters listed in Section (a). In the spine regions, Equations 1 and 2 are replaced by h=hs and JTM=0, respectively. Equations 3 through 5 are unchanged, excepted that w and h are replaced with hd and wd, respectively. The boundary conditions are given as IOP=Psc at x=0 and Q=0 at x=L. Additionally, Psc and Q are continuous at the distal end of the scaffold.

The baseline values of the constants are given in Table 1.

TABLE 1

Universal Parameters

| Parameter | Description | Value |
|---|---|---|
| $h_0$ | Intrinsic Height of SC | 20 μm |
| w | Width of SC | 230 μm |
| L | Length of SC | 36 mm |
| E | Young's modulus of TM | 30 mmHg |
| ΔP | IOP - $P_{epi}$ | 5 ≤ ΔP ≤ 30 mmHg |
| $N_{CC}$ | Number of CCs | 30 |
| $R_{TM}$ | TM Resistance to Flow | 9 cm mmHg/(μl/min) |
| $R_{CC}$ | Resistance to flow in CC | 2.5*$N_{CC}$ mmHg/(μl/min) |
| β | Ratio of RCC in control SC vs. SC with TM bypass | 3 |
| μ | Viscosity of AH | 7.5 × $10^{-4}$ kg/(m sec) or 0.75 cP |

Dimensions of the implants shown in Tables 2A-2B are estimated based on the actual sizes except width.

TABLE 2A

Geometric Parameters of 8 mm implant

| Parameter | Description | Value |
|---|---|---|
| $A_w$ | Area of window region | 17553 μm² |
| $A_s$ | Area of spine region | 22955 μm² |
| $A_{in}$ | Area of inlet region | 29841 μm² |
| $h_w$ | Height of window region | 76.3 μm |
| $h_s$ | Height of spine region | 99.8 μm |
| $h_{in}$ | Height of inlet region | 129.7 μm |
| $L_w$ | Length of window region | 1.1 mm |
| $N_w$ | Number of windows | 3 |
| $w_d$ | Width of device | 230 μm |
| $L_{in}$ | Length of inlet spine region | 1.1 mm |
| $L_{dev}$ | Length of device in SC | 7.2 mm |
| $L_s$ | Length of spine region | 0.9 mm |

TABLE 2B

Geometric Parameters of 16 mm implant

| Parameter | Description | Value |
|---|---|---|
| $A_w$ | Area of window region | 20994 μm² |
| $A_s$ | Area of spine region | 32092 μm² |
| $A_{in}$ | Area of inlet region | 29841 μm² |
| $h_w$ | Height of window region | 91.3 μm |
| $h_s$ | Height of spine region | 139.5 μm |
| $h_{in}$ | Height of inlet region | 129.7 μm |
| $L_w$ | Length of window region | 1 mm |
| $N_w$ | Number of windows | 5 |
| $w_d$ | Width of device | 230 μm |
| $L_{in}$ | Length of inlet spine region | 1.1 mm |
| $L_{dev}$ | Length of device in SC | 15 mm |
| $L_s$ | Length of spine region | 1.5 mm |

For simplicity, the width of all implants are assumed to be the same as that of the intact Schlemm's canal; and the height of each implant is calculated from the cross-sectional areas estimated for that device divided by $w_d$. In Table 1, the viscosity of aqueous humor (μ) at 37° C. is assumed to be the same as that measured at 34° C., because j is close to the viscosity of water which changes only slightly (~6%) when the temperature is increased from 34° C. to 37° C. The pressure in the episcleral vein ($P_{epi}$) is close to zero in experiments involving ex vivo perfusion of whole eye or anterior segment, but approximately equal to 8 mmHg in live eyes. In order to apply conclusions obtained from this mathematical model to both types of studies, ΔP was varied between 5 and 30 mmHg, where ΔP=IOP−$P_{epi}$, instead of changing the absolute value of IOP. Implantation of a bypass causes a significant increase in the pressure in this region of Schlemm's canal and can lead to an increase in the diameter of collector channel ostia in the region. To account for diameter increase-induced decrease in outflow resistance in collector channels, a parameter, β, can be defined as the ratio of $R_{CC}$ with ostia in control Schlemm's canal versus that in dilated Schlemm's canal. The value of β, which is >1, depends on how the three-dimensional shape of the collector channel is changed due to Schlemm's canal dilation and pressure increase, which is unknown at present. If the collector channel is considered as a circular channel, and its diameter is uniformly increased by a factor of two, then β equals 16 for Newtonian fluid. However, it is likely that only the portion of the collector channel near its ostium is be dilated after device implantation. Thus, a baseline value of β is assumed to be three.

In control simulations, with the frequent and uniform distribution of collector channel ostia in Schlemm's canal, the pressure difference between Schlemm's canal and episcleral venous pressure ($Psc-P_{epi}$) showed negligible variation. This resulted in negligible circumferential flow along Schlemm's canal. When the pressure drop between the anterior chamber and episcleral veins (ΔP) was fixed at different pressures, ranging from 5 to 30 mmHg, the shapes of these profiles varied only slightly although their magnitudes were increased significantly. Therefore, only the profiles at 10 mmHg are shown in this disclosure. The total sum of the flow rates through the collector channels per unit ΔP is defined as the outflow facility (C). The average C of the control eye was 0.198 μl/min/mmHg (Table 3). When ΔP is increased from 5 to 30 mmHg, C decreased slightly in the control simulation with TM intact, which falls within the range of experimental data of human eyes reported in the literature.

TABLE 3

Simulated Outflow Facility

| Simulation | Average Outflow Facility |
|---|---|
| Control | 0.198 |
| 8 mm implant | 0.438 |
| 16 mm implant | 0.638 |

Figure 39:
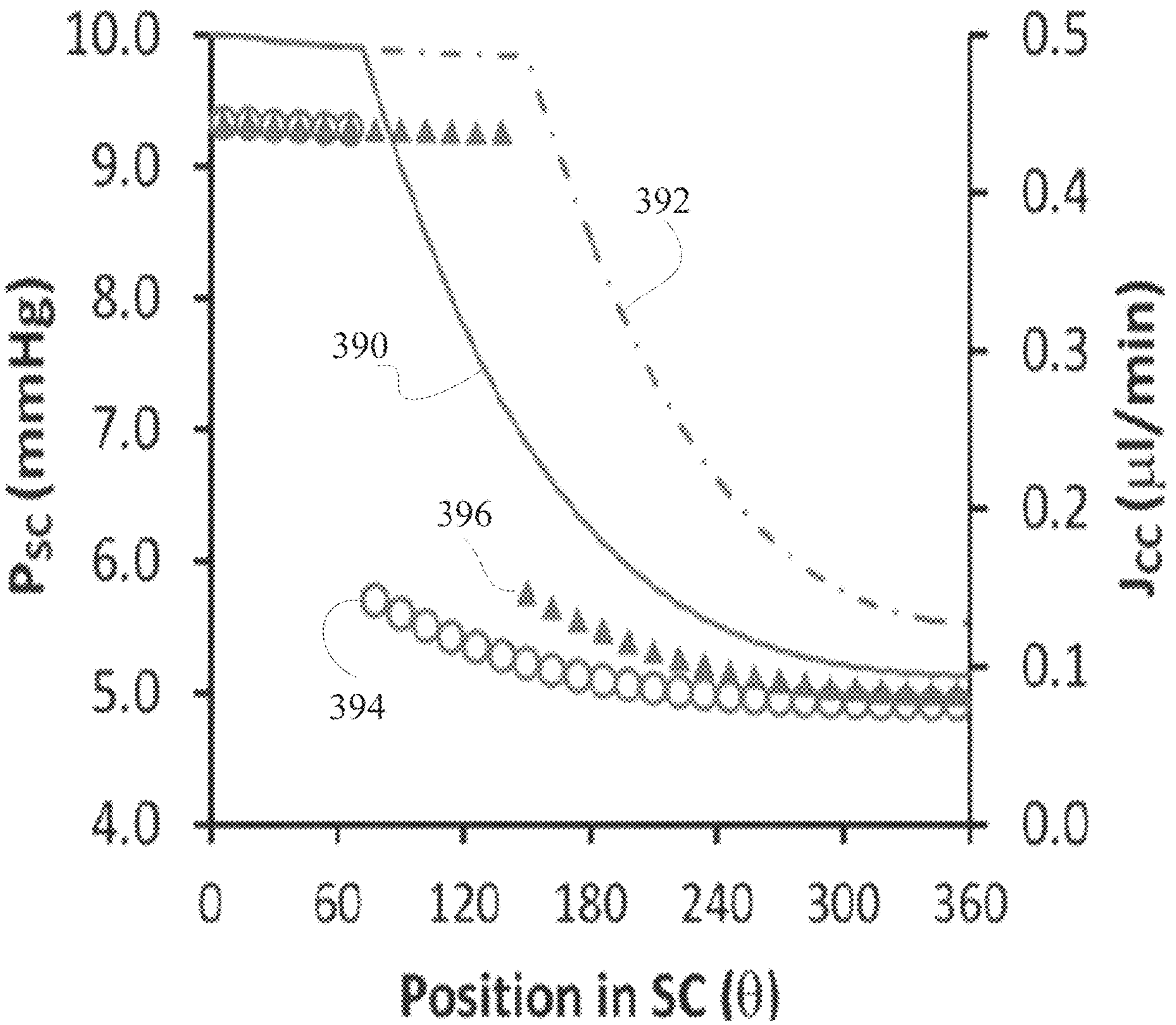
FIG. 39 is a diagram showing the results of mathematical simulations of 8 mm and 16 mm ocular implants.

FIG. 39 illustrates the results of mathematical simulations of the 8 mm and 16 mm implants with frequent and uniform circumferential distribution of collector channels and an IOP of 10 mmHg. In FIG. 39, solid line 390 represents the $P_{sc}$ in Schlemm's canal of the eye with the 8 mm implant, and dashed-line 392 represents the $P_{sc}$ in Schlemm's canal of the eye with the 16 mm implant. Circles 394 illustrate the flow in the collector channels of the eye with the 8 mm implant, and triangles 396 show the flow in the collector channels of the eye with the 16 mm implant. In the simulations, the pressure in the region of Schlemm's canal ($P_{sc}$) with the implants was similar to IOP. Outside this region, $P_{sc}$ decreased exponentially, starting at the distal end of the implants, with the smallest level of $P_{sc}$ slightly greater than controls.

Consequently, the outflow rate through the collector channels ($J_{cc}$) was highest in the implant regions due to the high $P_{sc}$ and Schlemm's canal dilation-induced reduction in outflow resistance in these collector channels. Outside this region, the profile of Jcc matched the Psc profile and was similar for both implants. The collector channels in the scaffold regions contributed to a majority of the overall difference in flow rate through collector channels when compared to controls. The average C value for the 8 mm implant was 121% greater than controls with a C value of 0.438 μl/min/mmHg and the 16 mm implant was 46% greater than the 8 mm implant (222% greater than controls) with a C value of 0.638 μl/min/mmHg (Table 3 above). However, the 16 mm implant reached twice as many collector channels as the 8 mm implant but only gained 46% greater outflow despite the addition of 6 collector channels. This indicates that as the distance from the collector channels to the inlet increases, the benefit to outflow facility diminishes.

Figure 40:
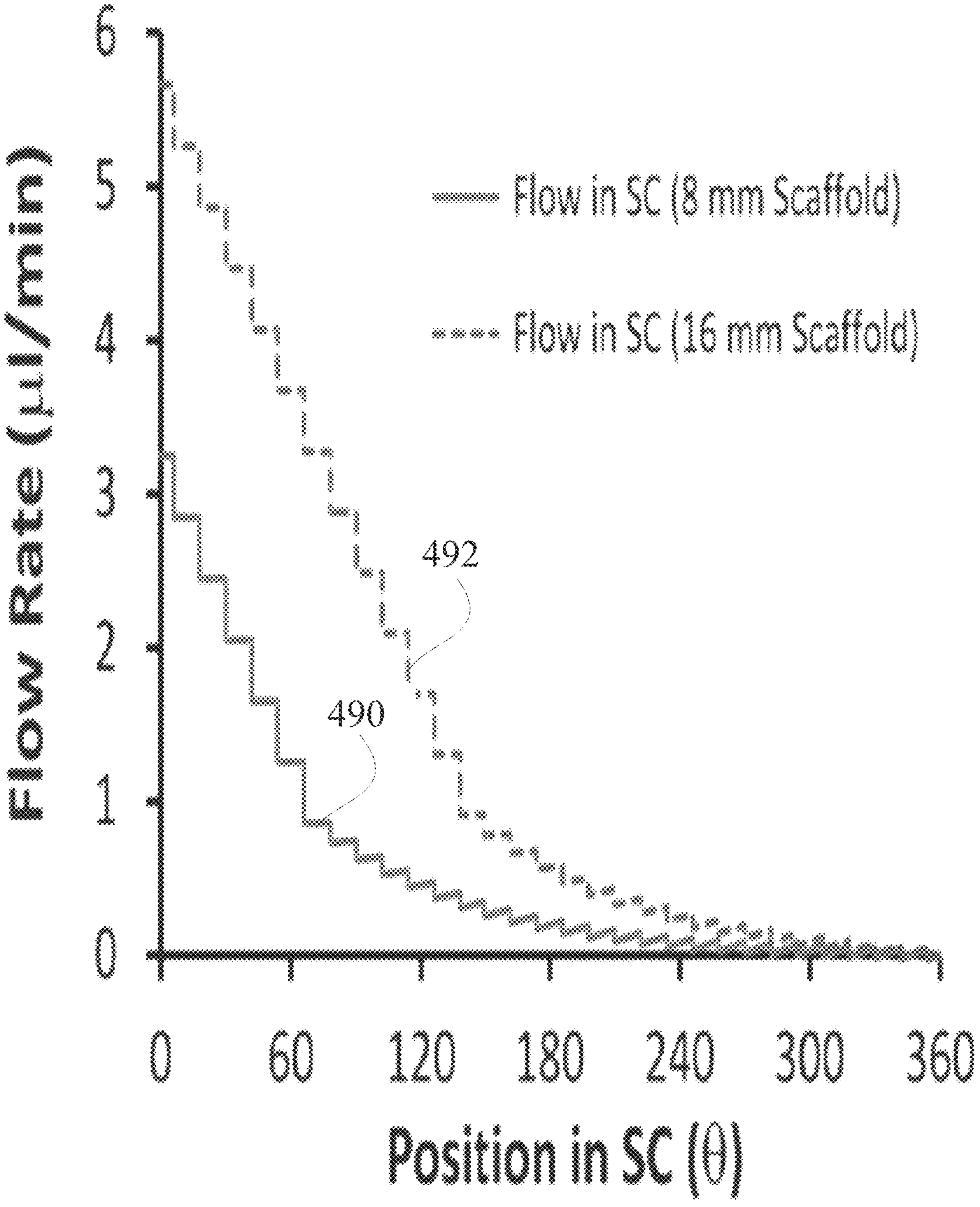
FIG. 40 is a diagram showing circumferential flow rates for 8 mm and 16 mm ocular implants.

Significant circumferential flow was observed adjacent to the trabecular meshwork bypass not seen in control simulations. The peak circumferential flow rate was 3.2 μl/min with the 8 mm implant and 5.7 μl/min with the 16 mm implant. The magnitude of the circumferential flow indicates a significant portion of the total outflow passed through the trabecular mesh bypass inlet. The circumferential flow rate peaked at the position of the bypass and decreased with a linear step pattern in the implant region. At the distal end of the scaffold, the circumferential flow rate decreased exponentially until it reached zero, as shown in FIG. 40, in which line 490 illustrates flow in Schlemm's canal in the 8 mm implant and line 492 illustrates flow in Schlemm's canal in the 16 mm implant. The circumferential flow region correlates to the regions of increased $P_{sc}$ and $J_{cc}$ for both the 8 mm and 16 mm implant. Throughout the first 90 degrees of Schlemm's canal, the 16 mm implant maintained a 2.415 μl/min flow difference versus the 8 mm implant. But when 150 degrees of Schlemm's canal is reached, the difference is reduced to only 0.526 μl/min, indicating a diminishing advantage with a longer length device.

Calculations of the percentage of total aqueous humor outflow through collector channels within an implant region indicate that the longer the implanted region the greater the percentage of total outflow (Table 4).

TABLE 4

Percent of Total Outflow Through Collector Channels in Schlemm's Canal regions with Implants

| Type of Implant | Percent of Schlemm's Canal Occupied | Average Percent of Total Outflow in Implant Region |
|---|---|---|
| 8 mm implant | 20% | 54.5% |
| 16 mm implant | 40% | 74.6% |

The 8 mm implant occupied three clock-hours of Schlemm's canal (20% of Schlemm's canal length), however the collector channels in that region accounted for 54.5% of the total outflow in the eye. The 16 mm implant occupied five clock-hours of Schlemm's canal (42% of Schlemm's canal length) which accounted for 74.6% of the total outflow. These results indicate that a significant portion of total outflow is diverted into the implant area and drains out collector channels adjacent to the implant. The more collector channels adjacent to the implant the larger a percentage of total outflow. Likewise, a segmental variation of the collector channel patency would make the outflow facility results dependent on implant location.

Theoretical in vivo glaucoma scenarios were designed to simulate how different ocular implants could improve outflow in eyes with increased trabecular meshwork resistance (RTM) and reduced collector channel outflow capacity in the hemisphere of the implant. Three scenarios were simulated in Table 5, with fixed conventional outflow rate of 1.5 μL/min 27, 28 and Pepi of 10 mmHg.

TABLE 5

Theoretical Glaucoma Scenarios

| Theoretical Scenario | $R_{TM}$ (mmHg/μl/min) | Collector Channels in Implant Hemisphere |
|---|---|---|
| Normal | 2.12 | Zero Blocked |
| Glaucoma Case #1 | 6.34 | 50% Blocked |
| Glaucoma Case #2 | 8.78 | 75% Blocked |

The first scenario was a normal eye, which assumed $R_{TM}$ to be 2.12 mmHg/μL/min and no blocked collector channels. The second scenario assumed $R_{TM}$ to be 6.34 mmHg/μL/min and 50% of the collector channels in the implanted hemisphere to be uniformly blocked including the collector channels at the trabecular mesh bypass. The third scenario assumed $R_{TM}$ to be 8.78 mmHg/μL/min and 75% of the collector channels in the implanted hemisphere to be uniformly blocked including the collector channel at the trabecular meshwork bypass. Simulation results showed that in the control eye without implant, the intra-ocular pressures under these scenarios were 17, 25 and 30 mmHg, respectively, and based on the Goldmann equation, the corresponding outflow facilities were 0.214, 0.100 and 0.075 μL/min/mmHg, respectively. Implantation of the 8 mm implant would improve the simulated outflow facility to 0.450, 0.240 and 0.171 μL/min/mmHg, or reduce IOPs to 13.3, 16.3 and 18.8 mmHg, respectively. When compared to the control simulations, the 8 mm implant resulted in IOP reductions of 22%, 35% and 37%, respectively.

The model shows the effects of trabecular meshwork bypass and Schlemm's canal dilation on outflow facility and subsequent IOP reduction. In analysis of the dilation length, increasing the dilated portion of Schlemm's canal from the bypass improved outflow facility. But, at a certain distance from the bypass there was diminished improvement. This indicates that dilation near the bypass creates circumferential flow from the bypass which allows more collector channels to be utilized.

Fluid dynamic mathematical modeling of scaffolding ocular implants as described herein shows that bypassing the trabecular meshwork increases the pressure within Schlemm's canal, and increases circumferential flow rate, and the flow rate into collector channels adjacent to the trabecular meshwork bypass. The larger bypass size creates a larger increase in the circumferential flow when compared with controls. Dilation of Schlemm's canal adjacent to the trabecular meshwork bypass increases the pressure in Schlemm's canal in the area of dilation which further increases the circumferential flow. Increasing the length of dilation increases the number of collector channels accessed by the implant, however, there was diminishing improvement in circumferential flow and flow rate into collector channels over a distance of approximately one quadrant in the eye beyond the region with the implant. When trabecular meshwork resistance was increased and collector channels were closed segmentally to simulate glaucoma, the dependence on the location of trabecular meshwork bypass to collector channels and the dilation length of Schlemm's canal was more pronounced.

Figure 41:
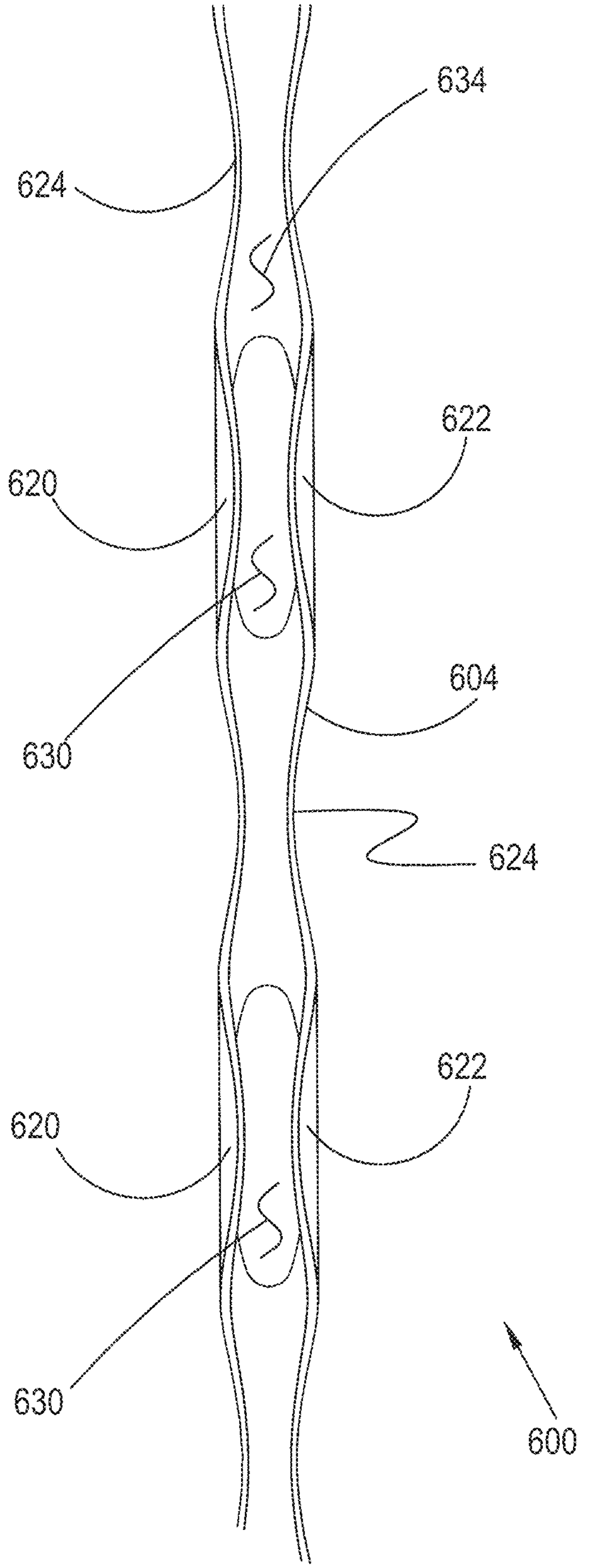
FIG. 41 is a top plan view showing an intermediate portion of an exemplary ocular implant.
Figure 42:
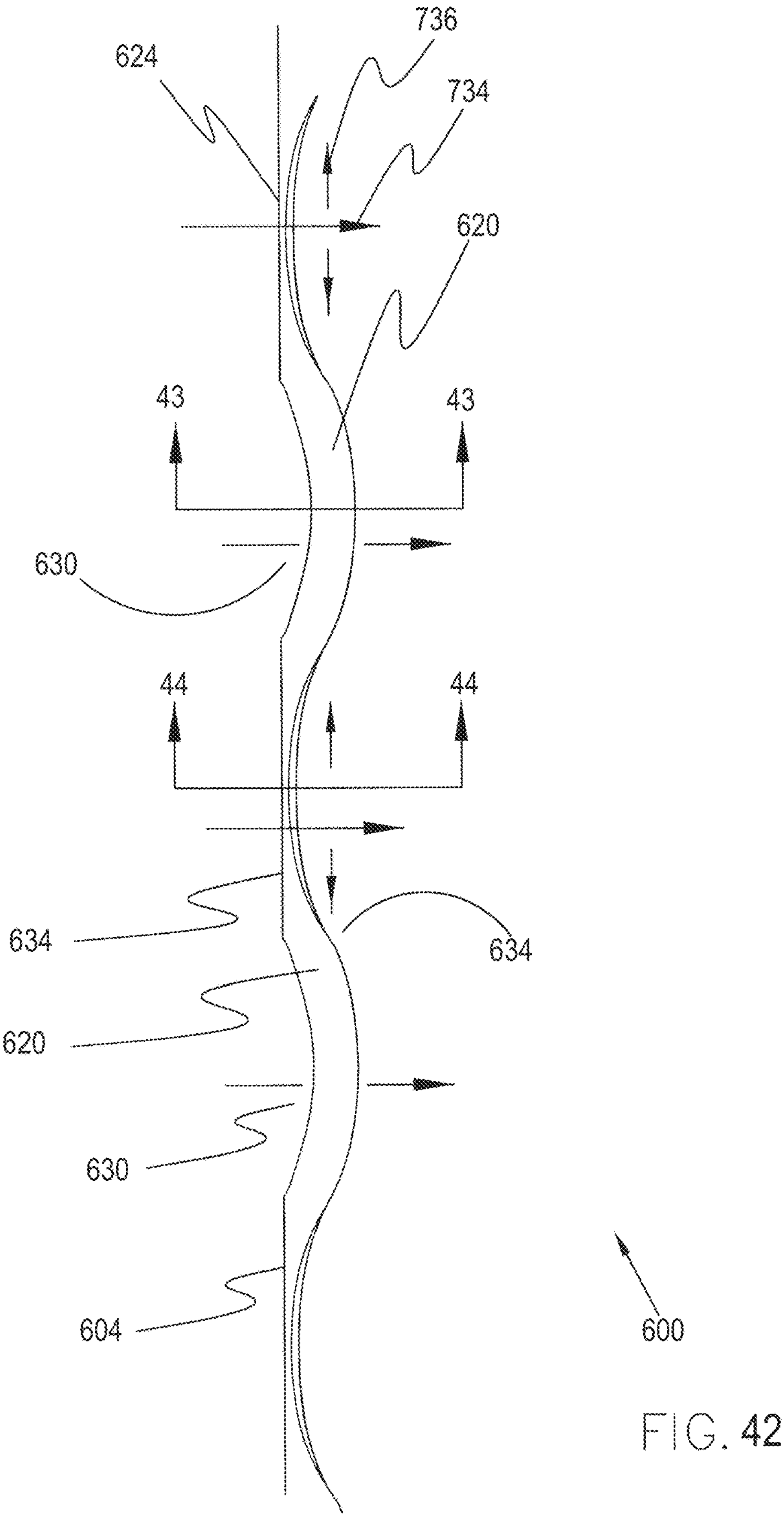
FIG. 42 is a side plan view of the ocular implant shown in the previous figure.

FIGS. 41 and 42 are top and side views showing an intermediate portion of an exemplary ocular implant 600. Ocular implant 600 may be inserted into Schlemm's canal, the trabecular meshwork and the anterior chamber to facilitate the outflow of aqueous humor from the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 600 will support trabecular mesh tissue and Schlemm's canal tissue and will provide for improved communication between the anterior chamber and Schlemm's canal (via the trabecular meshwork) and between pockets or compartments along Schlemm's canal.

Ocular implant 600 of FIGS. 41 and 42 comprises a body 604 having an outer surface 606. Body 604 of ocular implant 600 has a plurality of pairs of struts 620 and 622 separated by spine sections 624. The struts and spines define an open channel 634 whose open side lies along one longitudinal section of the implant body. A plurality of openings 630 are formed between the struts 620 and 622 on a longitudinal section of the implant opposite to the open side of channel 634. While in this embodiment the openings 130 are 180° from the open side of channel 134, in other embodiments openings 130 may be disposed 140°-150° the open side of channel 134. The diameter of body 604 is selected to support the tissue of Schlemm's canal without stretching it and is preferably in the range of 0.005 inches to 0.04 inches, most preferably in the range of 0.005 inches to 0.02 inches.

As shown in these figures, aqueous humor may flow axially down open channel 634 (as shown by arrows 736 in FIG. 42) or out of the implant through the opening of open channel 634 (first passing, e.g., through openings 630 and/or along the channel 634) as represented by lateral flow arrows 734. When implanted, body 604 of implant 600 preferably extends 60°, 90°, 150° or 180° around the circle formed by Schlemm's canal. The arrangement of struts, open areas and spine areas along implant 100 supports the tissue of Schlemm's canal with a minimum amount of material. In the embodiment shown in FIGS. 41 and 42, for example, the open areas extend over more than 50% of a hypothetical surface covering the volume of the portion of the implant lying within Schlemm's canal. This combination of features helps aqueous humor flow between any pockets or compartments formed within Schlemm's canal and, therefore, between the anterior chamber and the outlets from Schlemm's canal to the venous system.

Figure 43:
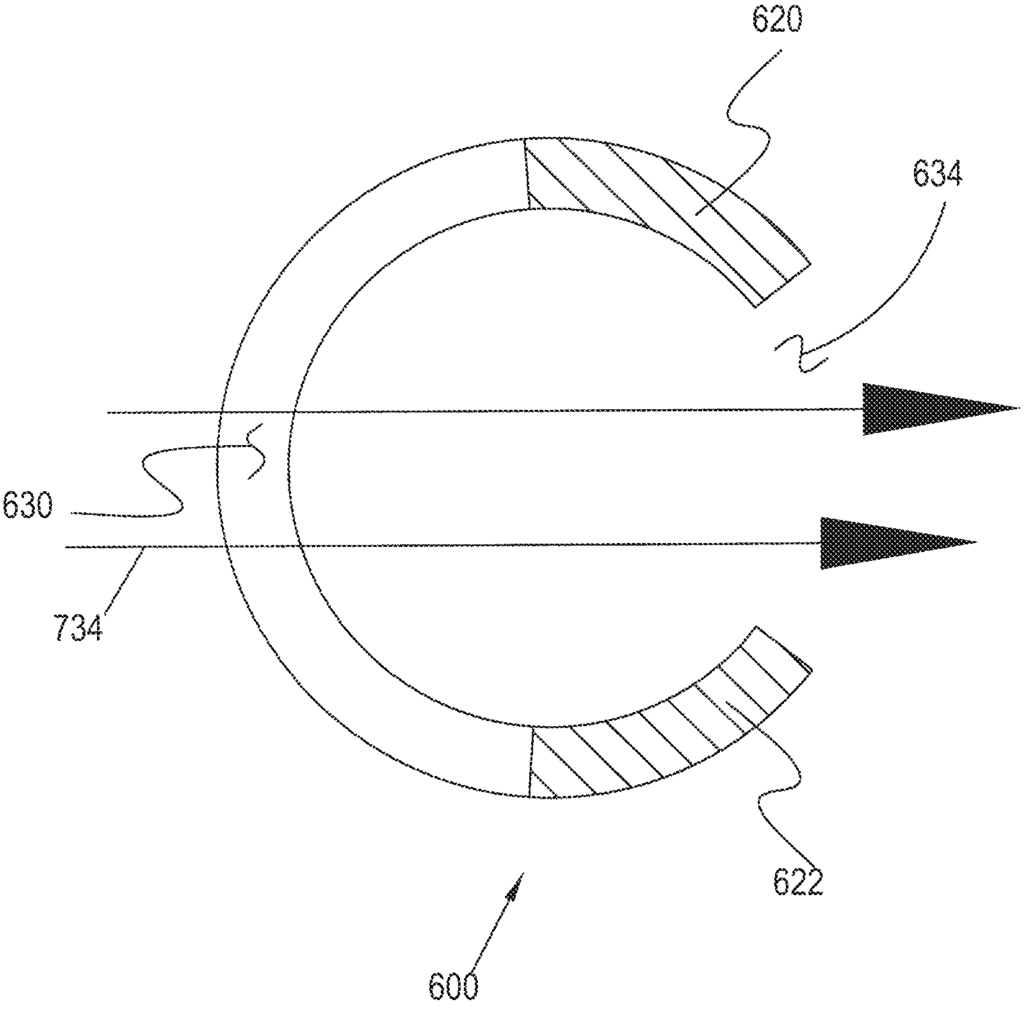
FIG. 43 is a lateral cross-sectional view of the ocular implant shown the previous figure.
Figure 44:
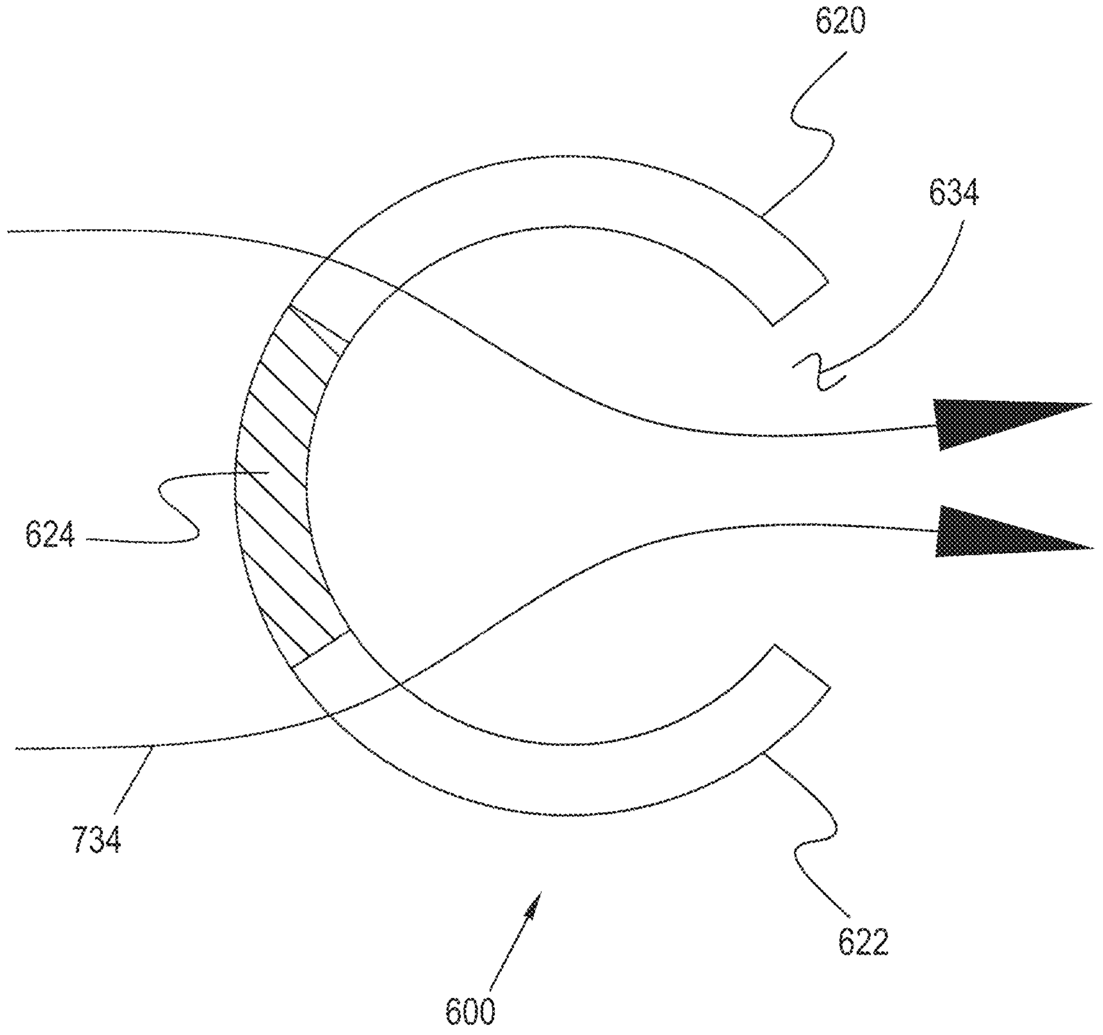
FIG. 44 is an additional lateral cross-sectional view of the ocular implant shown the previous figure.

FIG. 43 is a lateral cross-sectional view of ocular implant 600 taken along line 43-43 shown in FIG. 42, and FIG. 44 is a lateral cross-sectional view of ocular implant 600 taken along line 44-44 shown in FIG. 42. There are normally many flow paths from the anterior chamber through the trabecular meshwork into Schlemm's canal. Aqueous humor may therefore flow into channel 634 in body portion 604 of implant 600 from the trabecular meshwork through one or more openings 630 and/or around the struts 620/622 and spines 624. Thus, in FIG. 43, aqueous humor flowing past a spine area 624 is illustrated with lateral flow arrows 734, and in FIG. 44, aqueous humor flowing between first strut area 620 and second strut area 622 is illustrated using lateral flow arrows 34.

FIGS. 43 and 44 also illustrate another unique feature of implant 600: The arrangement of struts, openings and spine areas ensures that material coverage of Schlemm's canal in virtually any cross-section of the implant and canal is less than 50%. This material coverage relationship hold true for over 90% of the implant's length.

Figure 45B:
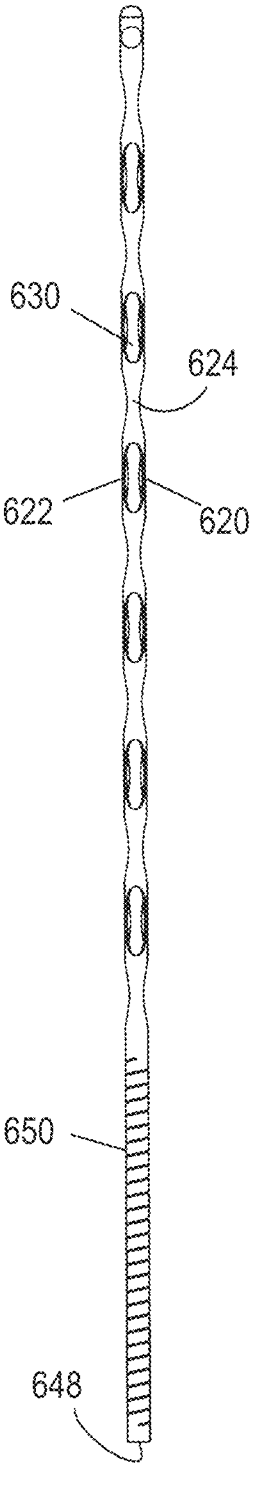
FIGS. 45A, 45B, and 45C are side, bottom and top plan views (respectively) illustrating an exemplary ocular implant.
Figure 45A:
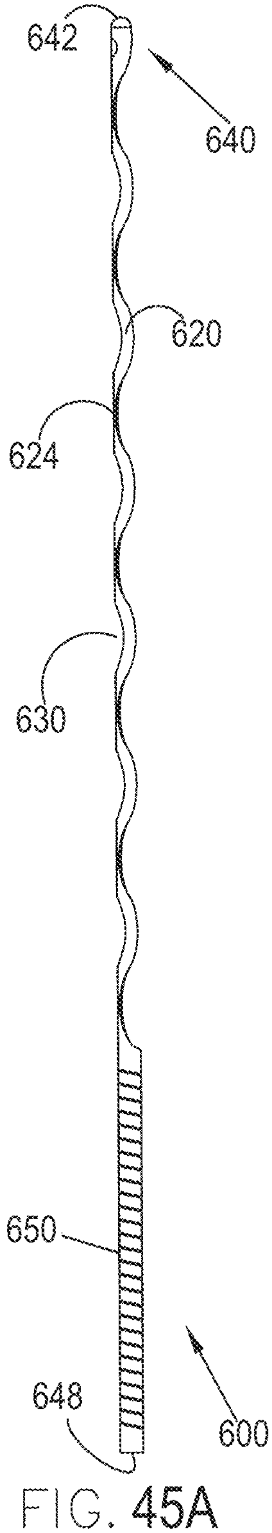
Figure 45C:
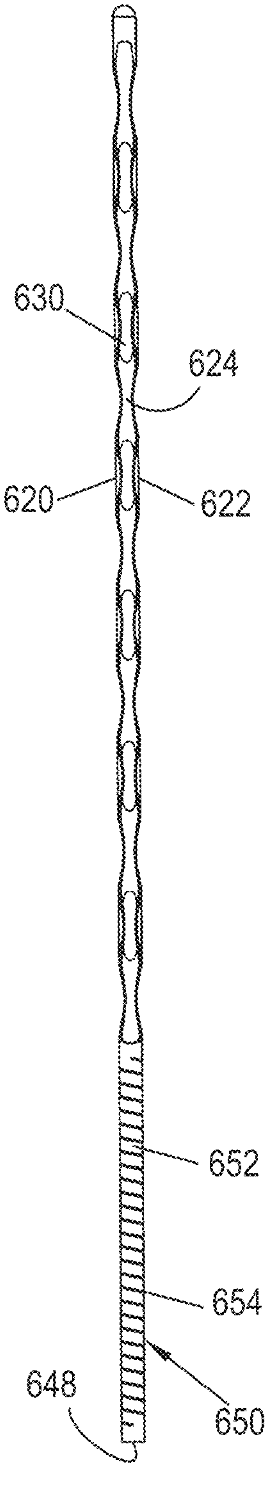
Figures 46A, 46B, 46C:
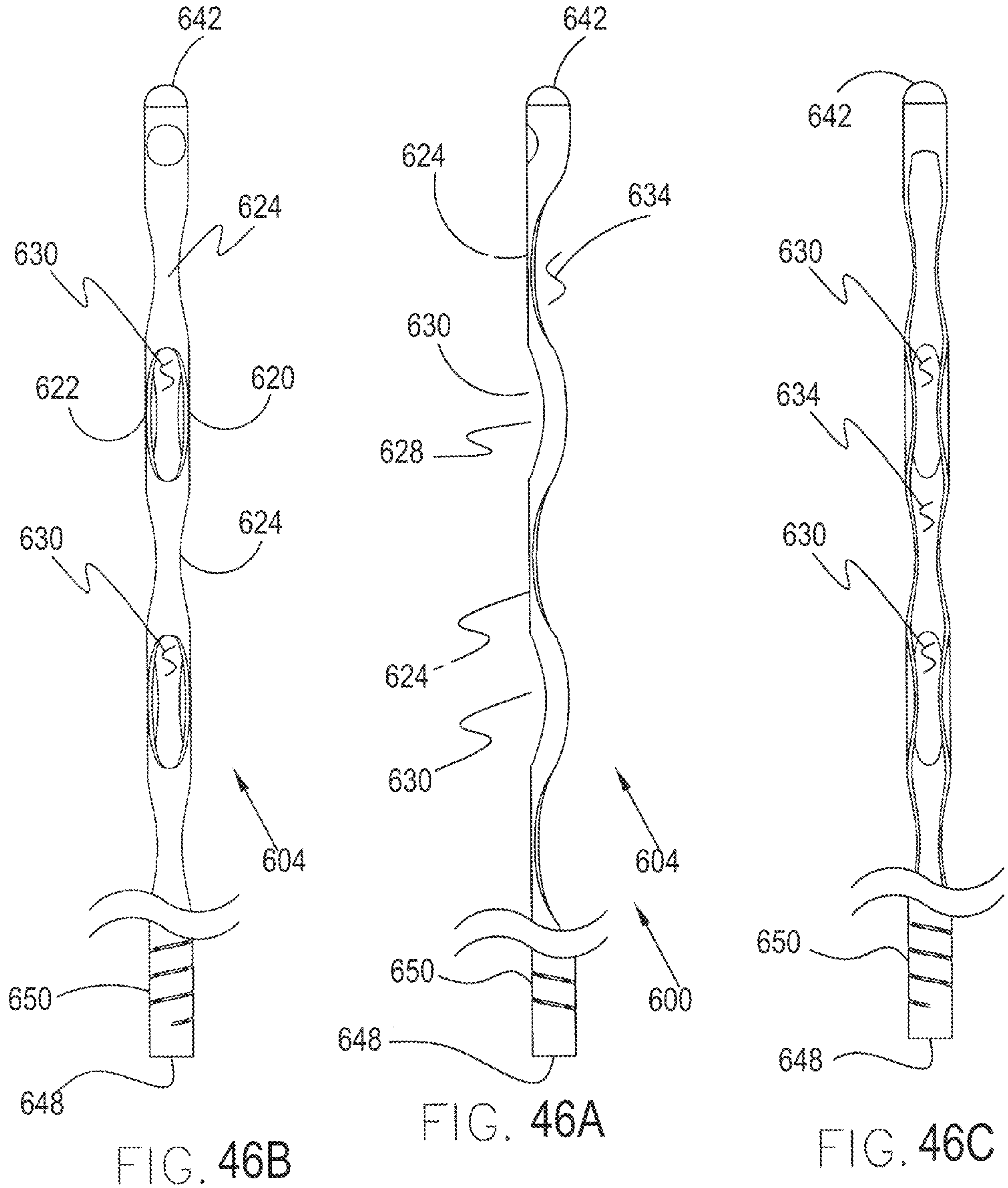
FIGS. 46A, 46B, and 46C are additional, larger side, bottom and top plan views (respectively) of the exemplary ocular implant shown in FIGS. 45A, 45B, and 45C.

In some embodiments, in addition to a Schlemm's canal portion as described above, the ocular implant also includes at least one optional inlet portion adapted to be disposed in the anterior chamber of the eye. The inlet portion is configured to support trabecular mesh tissue and to permit aqueous humor to flow from the anterior chamber into the open channel of the implant within Schlemm's canal. FIGS. 45A-C and 46A-C illustrate an exemplary ocular implant 600 with an optional inlet region 650 in addition to a plurality of struts 620, 622, openings 630 and spine areas 624 substantially the same as the previous embodiment. In the embodiment of FIGS. 45 and 46, inlet region 650 of ocular implant 600 comprises a coil. Coil 650 comprises a plurality of turns 652 that are defined by a generally helical slot 654. Coil 650 may be bent so as to project through the trabecular mesh into the anterior chamber while the remainder of the device lies within Schlemm's canal. Aqueous humor can flow into the inlet region through an open end 648 and through slot 654.

In some embodiments, the ocular implant may have an optional blunt tip for use in facilitating atraumatic delivery of the device into Schlemm's canal. As shown in FIGS. 45 and 46, distal portion 640 of ocular implant 600 comprises a blunt tip 642. In some useful embodiments of ocular implant 600, blunt tip 642 has a generally rounded shape. In the embodiment shown in FIGS. 45 and 46, blunt tip 642 has a generally hemispherical shape.

In the embodiment of FIGS. 45 and 46, body 604 of ocular implant 600 is pictured assuming a generally straight shape. Embodiments of ocular implant 600 are possible in which body 604 has a generally curved resting shape.

Ocular implant 600 can be fabricated, for example, by providing a tube and laser cutting openings in the tube to form the shape shown in FIGS. 45 and 46. Body 604 of ocular implant 600 can be fabricated from various biocompatible material possessing the necessary structural and mechanical attributes. Both metallic and non-metallic materials may be suitable. Examples of metallic materials include stainless steel, tantalum, gold, titanium, and nickel-titanium alloys known in the art as Nitinol. Nitinol is commercially available from Memry Technologies (Brookfield, Conn.), TiNi Alloy Company (San Leandro, Calif.), and Shape Memory Applications (Sunnyvale, Calif.).

Ocular implant 600 may include a therapeutic agent deposited on body 604. The therapeutic agent may, for example, be incorporated into a polymeric coating that is deposited out the outer surface 606 of body 604. The therapeutic agent may comprise an anti-glaucoma drug. Examples of anti-glaucoma drugs include prostaglandin analogs. Examples of prostaglandin analogs include latanprost.

Ocular implant 600 may be used in conjunction with a method of treating a patient. Some such methods may include the step of inserting a core member into a lumen defined by ocular implant 600. The core member may comprise, for example, a wire or tube. The distal end of the ocular implant may be inserted into Schlemm's canal. The ocular implant and the core member may then be advanced into Schlemm's canal until the ocular implant has reached a desired position. The core member may then be withdrawn from the ocular implant.

Figure 47:
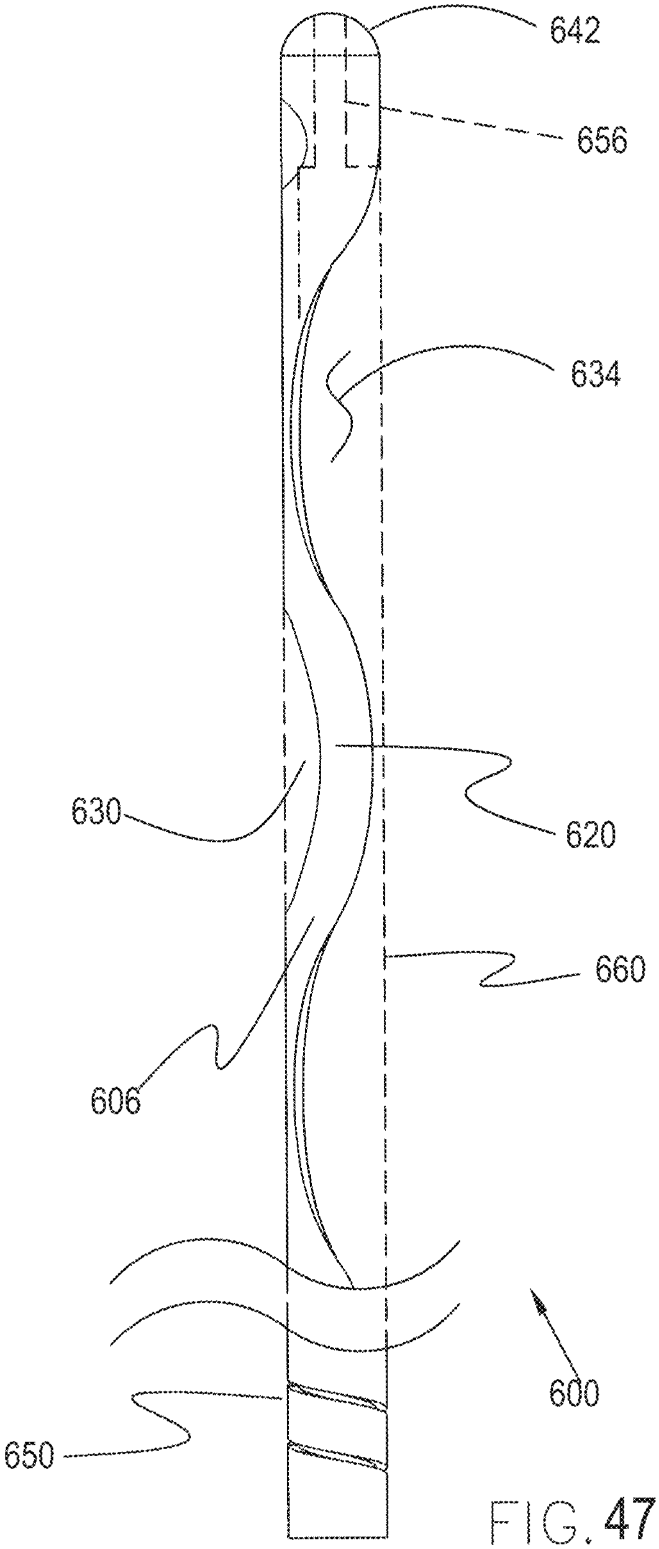
FIG. 47 is an additional side plan view illustrating the ocular implant shown in the previous figure.
Figure 48:
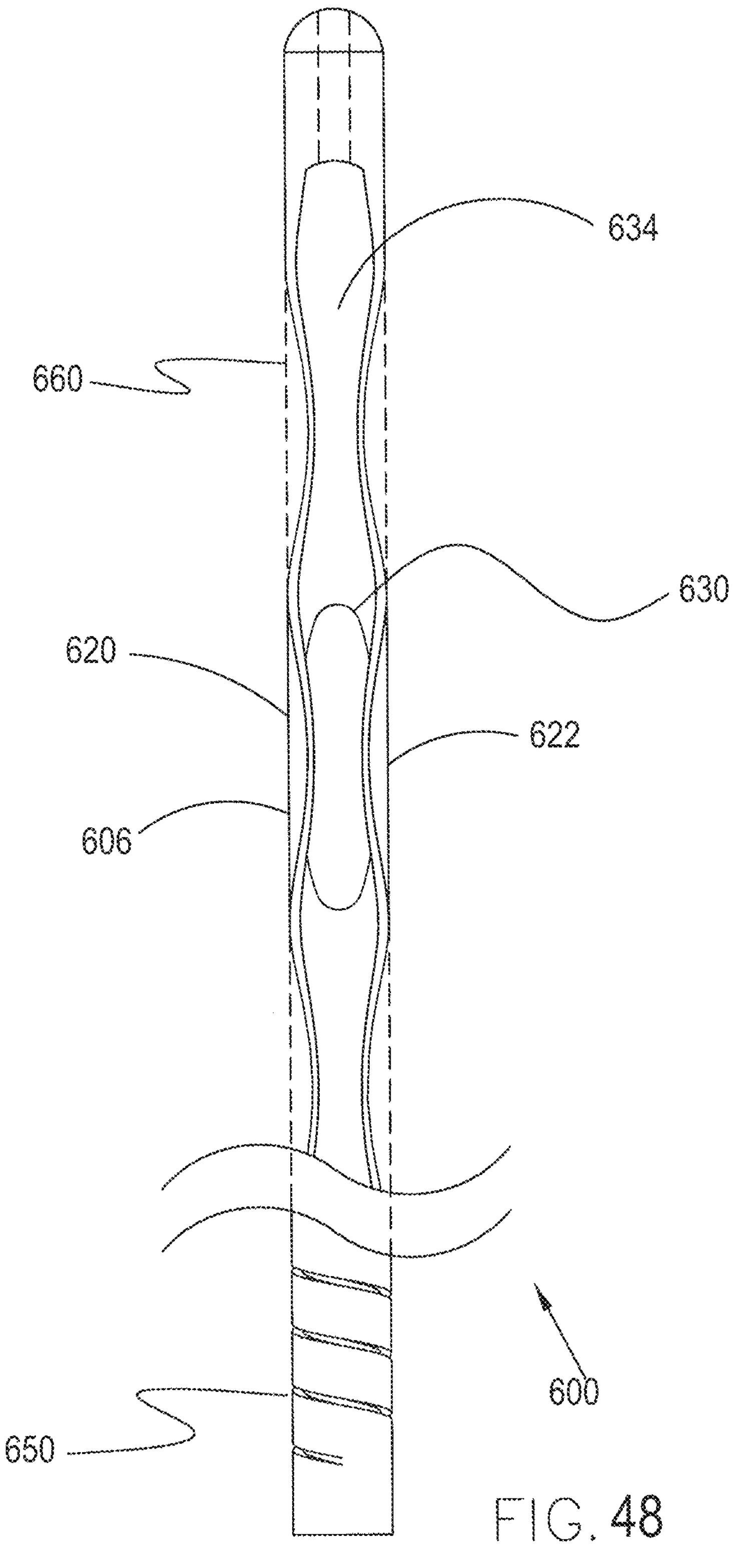
FIG. 48 is a top plan view illustrating the ocular implant shown in the previous figure.

FIGS. 47 and 48 show another embodiment of an ocular implant 600 similar to that of FIGS. 45 and 46. With reference to FIGS. 47 and 48, a lumen 656 is formed in blunt tip 642. This lumen may be used to inject a contrast medium through the blunt tip during implantation of the implant into the patient's eye. Lumen 656 may also be used to inject a visco-elastic medium in front of the implant to part tissue as the implant moves into Schlemm's canal.

A dotted line 660 in FIGS. 47 and 48 indicates a cylindrical envelope surrounding implant 600. In some embodiments, the open areas of ocular implant 600 (made up of openings 630 and the open portion of open channel 634) extend over more than 50% of cylindrical surface 660.

While exemplary embodiments of the present invention have been shown and described, modifications may be made, and it is therefore intended in the appended claims to cover all such changes and modifications which fall within the true spirit and scope of the invention.

What is claimed is:

1. A method of inserting an ocular implant into Schlemm's canal, the method comprising:
moving the ocular implant into Schlemm's canal while injecting a visco-elastic medium in front of the implant through a lumen of the implant, wherein the lumen is positioned distal to a channel defined through at least part of the implant, and wherein the lumen is in fluid communication with the channel.

2. The method of claim 1 wherein injecting comprises injecting the visco-elastic medium through a distal tip of the implant.

3. The method of claim 2 wherein injecting further comprises injecting the visco-elastic medium through a lumen extending to the distal tip.

4. The method of claim 3, further comprising injecting the visco-elastic medium in front of the implant by injecting the visco-elastic medium through the lumen extending to the distal tip and out of the distal tip.

5. The method of claim 2, wherein the distal tip of the implant is a blunt tip.

6. The method of claim 2, wherein the distal tip comprises a rounded distal end, wherein the lumen extends through the distal tip to the rounded distal end.

7. The method of claim 1, wherein the implant comprises a body comprising a plurality of struts separated by spine sections, and wherein the struts surround open areas defined along the body.

8. The method of claim 7, wherein the open areas extend over more than 50% of a hypothetical surface covering the implant.

9. The method of claim 7, wherein the channel is defined by the plurality of struts and spine sections.

10. The method of claim 1, further comprising injecting the visco-elastic medium in front of the implant to part tissue as the implant moves into Schlemm's canal.

11. The method of claim 1, further comprising injecting a contrast medium through the lumen.

* * * * *